(12) United States Patent
McConnell et al.

(10) Patent No.: US 8,304,556 B2
(45) Date of Patent: *Nov. 6, 2012

(54) THIAZOLYL-DIHYDRO-INDAZOLES

(75) Inventors: Darryl McConnell, Vienna (AU); Maria Impagnatiello, Vienna (AU); Dirk Kessler, Vienna (AU); Oliver Kraemer, Vienna (AU); Siegfried Schneider, Vienna (AU); Lars Van Der Veen, Alsbach-Hähnlein (AU); Ulrike Weyer-Czernilofsky, Baden (AU); Tobias Wunberg, Hinterbruehl (AU)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/347,797

(22) Filed: Jan. 11, 2012

(65) Prior Publication Data

US 2012/0108567 A1    May 3, 2012

Related U.S. Application Data

(63) Continuation of application No. 12/921,588, filed as application No. PCT/EP2009/052959 on Mar. 13, 2009, now abandoned.

(30) Foreign Application Priority Data

Mar. 13, 2008 (EP) ................... 08152721

(51) Int. Cl.
*A61K 31/429* (2006.01)
*C07D 513/04* (2006.01)

(52) U.S. Cl. .............. 548/151; 514/366; 514/232.8; 514/254.02; 514/318; 514/322; 544/133; 544/367; 544/364; 546/13; 546/193; 546/209; 546/256; 546/270.1

(58) Field of Classification Search .......... 548/151
See application file for complete search history.

(56) References Cited

U.S. PATENT DOCUMENTS

| | | | |
|---|---|---|---|
| 7,691,888 B2 | 4/2010 | Betzemeier et al. | |
| 7,893,049 B2 | 2/2011 | McConnell et al. | |
| 7,902,183 B2 | 3/2011 | Steurer et al. | |
| 2006/0100254 A1 | 5/2006 | Betzemeier et al. | |
| 2007/0259855 A1 | 11/2007 | Maier et al. | |
| 2007/0270401 A1 | 11/2007 | Steurer et al. | |
| 2008/0081802 A1 | 4/2008 | McConnell et al. | |
| 2009/0093474 A1 | 4/2009 | Grauert et al. | |

FOREIGN PATENT DOCUMENTS

| | | |
|---|---|---|
| CA | 2579288 A1 | 4/2006 |
| CA | 2646536 A1 | 10/2007 |
| CA | 2647278 A1 | 10/2007 |
| DE | 102004048877 A1 | 4/2006 |
| WO | 2006/040279 A1 | 4/2006 |
| WO | 2006/040281 A1 | 4/2006 |
| WO | 2007/113245 A1 | 10/2007 |
| WO | 2007/113246 A1 | 10/2007 |
| WO | 2007/115930 A1 | 10/2007 |
| WO | 2007/115933 A1 | 10/2007 |

OTHER PUBLICATIONS

International Search Report for corresponding PCT/EP2009/052959; date of mailing Aug. 5, 2009.
Golub et al, Molecular Classification of Cancer: Class Discovery and Class Prediction by Gene Expression Monitoring , Science, Oct. 15, 1999, pp. 531-537, vol. 286.

*Primary Examiner* — Laura L. Stockton
(74) *Attorney, Agent, or Firm* — Michael P. Morris; Alan R. Stempel

(57) ABSTRACT

The present invention encompasses compounds of general formula (1)

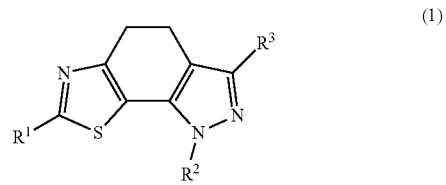

(1)

wherein $R^1$ to $R^3$ are defined as in claim 1, which are suitable for the treatment of diseases characterized by excessive or abnormal cell proliferation, and the use thereof for preparing a medicament having the above-mentioned properties.

5 Claims, No Drawings

THIAZOLYL-DIHYDRO-INDAZOLES

The present invention relates to new thiazolyl-dihydro-indazoles of general formula (1)

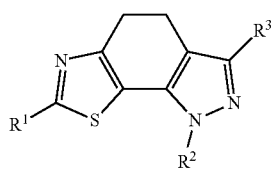

(1)

wherein the groups $R^1$ to $R^3$ have the meanings given in the claims and specification, the isomers thereof, processes for preparing these thiazolyl-dihydro-indazoles and their use as medicaments.

BACKGROUND TO THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol-3-kinases (PI3-kinases) are a subfamily of the lipid kinases which catalyse the transfer of a phosphate group to the 3'-position of the inositol ring of phosphoinositides.

They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories.

DETAILED DESCRIPTION OF THE INVENTION

It has now surprisingly been found that compounds of general formula (1), wherein the groups $R^1$ to $R^3$ have the meanings given below, act as inhibitors of specific cell cycle kinases. Thus, the compounds according to the invention may be used for example for the treatment of diseases connected with the activity of specific cell cycle kinases and characterised by excessive or abnormal cell proliferation.

The present invention relates to compounds of general formula (1)

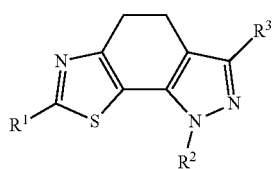

(1)

wherein
$R^1$ is selected from among —$NHR^c$, —$NHC(O)R^c$, —$NHC(O)OR^c$, —$NHC(O)NR^cR^c$, —$NHC(O)N(R^g)OR^c$ and —$NHC(O)SR^c$, and
$R^2$ denotes hydrogen or a group selected from among $C_{1-6}$alkyl, $C_{3-8}$cycloalkyl, 3-8 membered heterocycloalkyl, $C_{6-10}$aryl, $C_{7-16}$arylalkyl and 5-10 membered heteroaryl, optionally substituted by one or more identical or different $R^4$ and
$R^3$ denotes a 6 membered heteroaryl, substituted by one or more identical or different $R^a$ and/or $R^b$, or
$R^3$ denotes a 8-10 membered heteroaryl, optionally substituted by one or more identical or different $R^e$ and/or $R^f$, and
each $R^4$ denotes a group selected from among $R^a$, $R^b$ and $R^a$ substituted by one or more identical or different $R^b$ and/or $R^c$; and
each $R^a$ independently of one another denotes a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^b$ denotes a suitable group and is selected independently of one another from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —$CN$, —$NC$, —$OCN$, —$SCN$, —$NO$, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$O(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$, —$N(R^g)C(NR^g)NR^cR^c$, —$N$=$R^cR^c$ and —$N$=$C(R^g)NR^cR^c$ and
each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$halo alkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and
each $R^d$ denotes a suitable group and is selected independently of one another from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —$CN$, —$NC$, —$OCN$, —$SCN$, —$NO$, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)

$R^e$, —N[C(O)$R^e$]NR$^e$R$^e$, —N(R$^g$)C(S)R$^e$, —N(R$^g$)S(O)R$^e$, —N(R$^g$)S(O)OR$^e$—N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$, —N(R$^g$)C(NR$^g$)NR$^e$R$^e$, —N=R$^e$R$^e$ and —N=C(R$^g$)NR$^e$R$^e$ each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$halo alkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, and each R$^f$ denotes a suitable group and in each case is selected independently of one another from among =O, —OR$^g$, C$_{1-3}$haloalkyloxy, —OCF$_3$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^h$)NR$^g$R$^g$, —SC(O)R$^g$, —SC(O)OR$^g$, —SC(O)NR$^g$R$^g$, —SC(NR$^h$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O)R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(R$^h$)[S(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^h$NR$^g$R$^g$, —N(R$^h$)N(R$^h$)C(O)NR$^g$R$^g$, —N(R$^h$)C(S)NR$^g$R$^g$, —[N(R$^h$)C(O)]$_2$R$^g$, —N(R$^h$)[C(O)]$_2$R$^g$, —N{[C(O)]$_2$R$^g$}$_2$, —N(R$^h$)[C(O)]$_2$OR$^g$, —N(R$^h$)[C(O)]$_2$NR$^g$R$^g$, —N{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$, —N(R$^h$)C(NR$^h$)NR$^g$R$^g$, —N=R$^h$R$^h$ and —N=C(R$^h$)NR$^h$R$^h$; and each R$^g$ independently of one another denotes hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero aryl, 6-18 membered heteroarylalkyl, 3-14 membered heterocycloalkyl and 4-14 membered heterocycloalkylalkyl; and each R$^h$ is selected independently of one another from among hydrogen, C$_{1-6}$alkyl, 2-6 membered heteroalkyl, C$_{1-6}$halo alkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the prodrugs, the tautomers, the racemates, the enantiomers, the diastereomers, the prodrugs and the mixtures thereof, and optionally the pharmacologically acceptable salts thereof.

One aspect of the invention are compounds of general formula (1), wherein R$^3$ is a radical selected from the group consisting of pyridyl, pyrazinyl, pyrimidinyl and pyridazinyl, optionally substituted by one or more R$^4$.

A further aspect of the invention are compounds of general formula (1), wherein R$^3$ is pyridyl.

A further aspect of the invention are compounds of general formula (1), wherein R$^3$ is substituted by a residue selected from the group consisting of halogen, —CN, —OR$^c$, —NR$^c$R$^c$ and C$_{1-6}$alkyl optionally substituted by R$^b$.

A further aspect of the invention are compounds of general formula (1), wherein R$^1$ is —NHC(O)R$^c$.

A further aspect of the invention are compounds of general formula (1), wherein R$^1$ is —NHC(O)CH$_3$.

A further aspect of the invention are compounds of general formula (1)—or the pharmaceutically active salts thereof—for use as a medicament.

A further aspect of the invention are compounds of general formula (1)—or the pharmacologically effective salts thereof, for preparing a medicament with an antiproliferative activity.

A further aspect of the invention is a pharmaceutical preparation, containing as active substance one or more compounds of general formula (1) or the physiologically acceptable salts thereof optionally in conjunction with conventional excipients and/or carriers.

A further aspect of the invention is the use of a compound of general formula (1) for preparing a pharmaceutical composition for the treatment and/or prevention of cancer, infections, inflammatory and autoimmune diseases.

A further aspect of the invention is a pharmaceutical preparation comprising a compound of general formula (1) and at least one other cytostatic or cytotoxic active substance, different from formula (1), optionally in the form of the tautomers, the racemates, the enantiomers, the diastereomers and the mixtures thereof, and optionally the pharmacologically acceptable acid addition salts thereof.

Definitions

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

The term heteroalkyl refers to groups which can be derived from alkyl as defined above in its broadest sense by replacing one or more of the groups —CH$_3$ in the hydrocarbon chains independently of one another by the groups —OH, —SH or —NH$_2$, one or more of the groups —CH$_2$— independently of one another by the groups —O—, —S— or —NH—, one or more of the groups

are replaced by the group

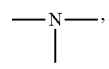

one or more of the groups =CH— by the group =N—, one or more of the groups =CH₂ by the group =NH or one or more of the groups =CH by the group =N, while in all only a maximum of three heteroatoms may be present in a heteroalkyl, there must be at least one carbon atom between two oxygen and between two sulphur atoms or between one oxygen and one sulphur atom and the group as a whole must have chemical stability.

It flows from the indirect definition/derivation from alkyl that heteroalkyl is made up of the sub-groups of saturated hydrocarbon chains with hetero-atom(s), heteroalkenyl and hetero-alkynyl, while further subdivision into straight-chain (unbranched) and branched may be carried out. If a heteroalkyl is supposed to be substituted, the substitution may take place independently of one another, in each case mono- or polysubstituted, at all the hydrogen-carrying oxygen, sulphur, nitrogen and/or carbon atoms. Heteroalkyl itself may be linked to the molecule as substituent both through a carbon atom and through a heteroatom.

By way of example, the following representative compounds are listed: dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Haloalkyl relates to alkyl groups, wherein one or more hydrogen atoms are replaced by halogen atoms. Haloalkyl includes both saturated alkyl groups and unsaturated alkenyl and alkynyl groups, such as for example —CF₃, —CHF₂, —CH₂F, —CF₂CF₃, —CHFCF₃, —CH₂CF₃, —CF₂CH₃, —CHFCH₃, —CF₂CF₂CF₃, —CF₂CH₂CH₃, —CF═CF₂, —CCl═CH₂, —CBr═CH₂, —Cl═CH₂, —C≡C—CF₃, —CHFCH₂CH₃ and —CHFCH₂CF₃.

Halogen refers to fluorine, chlorine, bromine and/or iodine atoms.

By cycloalkyl is meant a mono or bicyclic ring, while the ring system may be a saturated ring or, however, an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl and norbornenyl.

Cycloalkylalkyl includes a non-cyclic alkyl group wherein a hydrogen atom bound to a carbon atom, usually to a terminal C atom, is replaced by a cycloalkyl group.

Aryl relates to monocyclic or bicyclic aromatic rings with 6-10 carbon atoms such as phenyl and naphthyl, for example.

Arylalkyl includes a non-cyclic alkyl group wherein a hydrogen atom bound to a carbon atom, usually to a terminal C atom, is replaced by an aryl group.

By heteroaryl are meant mono- or bicyclic aromatic rings, which instead of one or more carbon atoms contain one or more, identical or different hetero atoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom, usually to a terminal C atom, is replaced by a heteroaryl group.

Heterocycloalkyl relates to saturated or unsaturated, non-aromatic mono-, bicyclic or bridged bicyclic rings comprising 3-12 carbon atoms, which instead of one or more carbon atoms carry heteroatoms, such as nitrogen, oxygen or sulphur. Examples of such heterocycloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, dioxaborolanyl, tetrahydrothienyl-S-oxide, tetrahydrothienyl-S,S-dioxide, homothiomorpholinyl-S-oxide, 2-oxa-5-azabicyclo[2,2,1]heptane, 8-oxa-3-aza-bicyclo[3.2.1]octane, 3.8-diaza-bicyclo[3.2.1]-octane, 2,5-diaza-bicyclo[2,2,1]heptane, 3.8-diaza-bicyclo[3.2.1]octane, 3.9-diaza-bicyclo[4.2.1]nonane and 2.6-diaza-bicyclo[3.2.2]nonane.

Heterocycloalkylalkyl relates to a non-cyclic alkyl group wherein a hydrogen atom bound to a carbon atom, usually to a terminal C atom, is replaced by a heterocycloalkyl group.

The following Examples illustrate the present invention without restricting its scope.

Intermediates A

The syntheses of substituted 5,6-dihydro-4H-benzothiazol-7-ones used herein as starting materials are described in earlier applications (see WO2006/040281, WO2007/113245, and WO2007/113246). Additional starting materials may be prepared by the procedures described therein.

General Procedure A1: Formation of Diketones from Acid Chlorides.

The monoketone is added to dry THF (e.g. 10 mmol in 90 mL solvent) and the suspension is cooled to −78° C. under inert atmosphere. LiHMDS (3.4 eq.) is slowly added to the reaction mixture so that the reaction temperature is kept below −60° C. After completion of the addition, a solution of the acid chloride (1.2 eq.) in dry THF (about 2-2.5 M) is added slowly. The reaction mixture is stirred overnight allowing it to warm to RT. For the work-up the mixture is cooled to −20° C. and the reaction is quenched with diluted hydrochloric acid and phosphate buffer (22 g NaH$_2$PO$_4$, 87 g Na$_2$HPO$_4$, 530 mL H$_2$O) resulting in a final pH about 6. Ethyl acetate is added and the organic layer is separated. The aqueous phase is extracted three times with ethyl acetate, the combined organic phases are dried over MgSO$_4$, filtered and the solvent is removed under reduced pressure. The remaining solid is treated with TBME and the solvent is filtered off. The product may be used without further purification.

General Procedure A2: Formation of Diketones from Esters

The monoketone (1.0 eq.) is dissolved in DMSO (1 M solution) and NaOtBu or sodium tert.-pentoxide (3.0 eq.) is slowly added. The reaction mixture is stirred for 30 min at room temperature before the ester (1.1 eq.) is added slowly. After completion of the addition the mixture is stirred for 4 h at RT, poured on ice and neutralized with saturated ammonium chloride solution. The precipitate is filtered off, washed with water dried under vacuum at 40° C. overnight. Alternatively, the solvent is evaporated after completion of the reaction and the crude product may be used for the next step without further purification.

General Procedure A3: Formation of Diketones from Active Esters.

a) Formation of the Active Ester

Carboxylic acid (1.0 eq.) is dissolved in CH$_2$Cl$_2$, CDI (1.0 eq.) is added and the reaction mixture is stirred at RT over night. The solvent is removed in vacuo and the crude product is used without further purification.

b) Formation of the Diketone

A 1 M solution of LiHMDS (3 eq.) in THF is diluted with THF and the resulting solution is cooled to −10° C. under inert atmosphere. The monoketone (1.0 eq.) is added in small portions so that the reaction temperature is kept below −10° C. After stirring one additional hour at −10° C. a solution of the active ester (2.0 eq.) in THF is added slowly. The reaction mixture is stirred over night allowing it to warm to RT. The reaction is quenched with a saturated solution of NH$_4$Cl in water and the aqueous phase is extracted twice with CH$_2$Cl$_2$. The combined organic layers are dried over MgSO$_4$, filtered and the solvent is removed under reduced pressure. The product is purified by RP-chromatography.

General Procedure A4: Nucleophilic Aromatic Substitution of o-fluoropyridines.

The o-fluoropyridine and an excess of the amine are dissolved in EtOH or iPrOH/THF (0.1-0.2 M) and the mixture is heated in the microwave at 100° C. for 30-60 min or alternatively at RT without heating (the reaction is typically monitored by LC-MS until all starting material has reacted). After completion of the reaction the solvent is removed in vacuo and the product is either purified by chromatography (NP with MeOH/DCM or RP with ACN/H$_2$O) or used without further purification.

A-01) N-[6-(6-Fluoro-pyridine-3-carbonyl)-7-hydroxy-4,5-dihydro-benzothiazol-2-yl]-acetamide

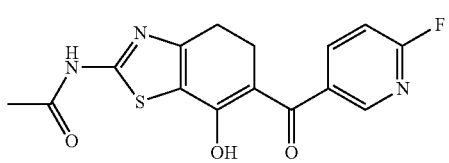

The title compound is synthesized according to general procedure A1 starting form 21.0 g (100 mmol), N-(7-oxo-4,5,6,7-tetrahydro-benzothiazol-2-yl)-acetamide and 20.2 g (120 mmol, 95% pure) 6-fluoro nicotinic acid chloride. Yield: 27.0 g.

A-02) N-[6-(6-Dimethylamino-pyridine-3-carbonyl)-7-hydroxy-4,5-dihydro-benzothiazol-2-yl]-acetamide

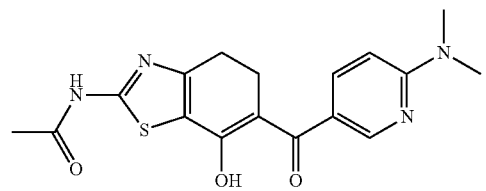

The title compound is obtained from 500 mg (1.5 mmol) A-01 and 5.0 mL of a 2 M solution of dimethylamine in THF (10 mmol). The reaction is performed in EtOH according to the general procedure A4. The product is purified by NP-chromatography. Yield 205 mg.

A-03) N-[6-(6-tert-Butylamino-pyridine-3-carbonyl)-7-hydroxy-4,5-dihydro-benzothiazol-2-yl]-acetamide

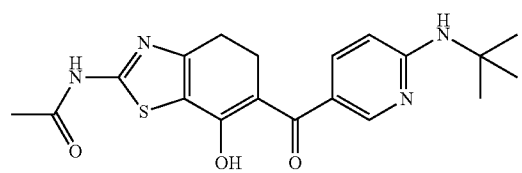

The title compound is obtained from 160 mg (0.39 mmol, ~81% purity) A-01 and 410 µL (3.90 mmol) tert-butylamine. The reaction is performed in EtOH according to the general procedure A4. The crude product is used without further purification. Yield: 157 mg.

A-04) N-[6-(6-Cyclopropylamino-pyridine-3-carbonyl)-7-hydroxy-4,5-dihydro-benzothiazol-2-yl]-acetamide

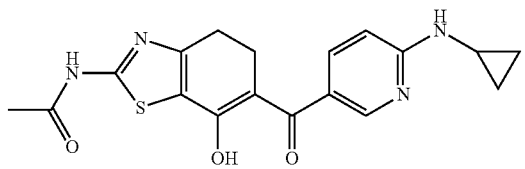

The title compound is obtained from 160 mg (0.39 mmol, about 81% purity) A-01 and 270 µL (3.90 mmol) cyclopropylamine. The reaction is performed in EtOH according to the general procedure A4. The crude product is used without further purification. Yield: 168 mg.

A-05) N-[6-(6-Allylamino-pyridine-3-carbonyl)-7-hydroxy-4,5-dihydro-benzothiazol-2-yl]-acetamide

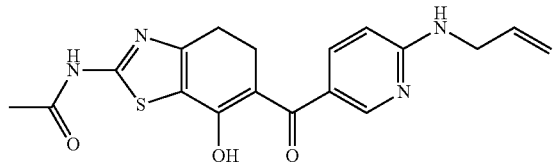

The title compound is obtained from 160 mg (0.39 mmol, about 81% purity) A-01 and 290 µL (3.87 mmol) allylamine according to the general procedure A4. The reaction is performed in EtOH. The crude product is used without further purification. Yield: 177 mg.

A-06) N-[7-Hydroxy-6-(6-isopropylamino-pyridine-3-carbonyl)-4,5-dihydro-benzothiazol-2-yl]-acetamide

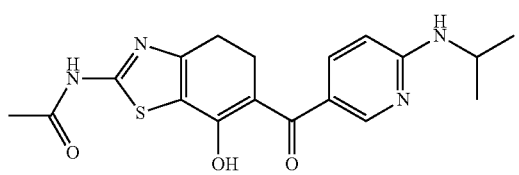

The title compound is obtained from 160 mg (0.39 mmol, about 81% purity) A-01 and 335 µL (3.89 mmol) isopropylamine. The reaction is performed in EtOH according to the general procedure A4. The crude product is used without further purification.

Yield: 179 mg.

A-07) N-[7-Hydroxy-6-(6-methylamino-pyridine-3-carbonyl)-4,5-dihydro-benzothiazol-2-yl]-acetamide

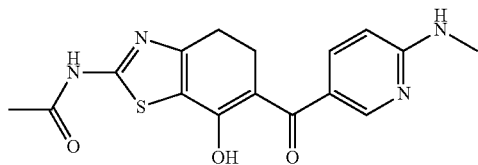

The title compound is obtained from 27.0 g (72.90 mmol, about 90% purity) A-01 and 27 mL (319.7 mmol) of a solution of methylamine in water. The reaction is performed in a 1:1 mixture of THF and iPrOH according to the general procedure A4. For the work-up a large portion of the solvent is removed under reduced pressure, the formed precipitate is filtered off and washed with a small amount of iPrOH as well as water. Yield: 17.8 g.

A-08) N-{6-[6-(2-Dimethylamino-ethylamino)-pyridine-3-carbonyl]-7-hydroxy-4,5-dihydro-benzothiazol-2-yl}-acetamide (A-08)

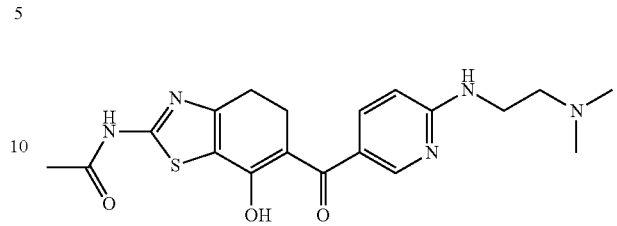

The title compound is obtained from 1.0 g (3.00 mmol) A-01 and 1.56 mL (14.1 mmol) N,N-dimethylethylendiamine. The reaction is performed in a 1:1 mixture of THF and iPrOH according to the general procedure A4. For the work-up the solvent is removed under reduced pressure, the residue taken up with water, extracted with $CH_2Cl_2$, the organic phase dried over $MgSO_4$, filtered and the solvent removed in vacuo. Yield: 1.49 g.

A-09) N-{7-Hydroxy-6-[6-(2-methoxy-ethylamino)-pyridine-3-carbonyl]-4,5-dihydro-benzothiazol-2-yl}-acetamide

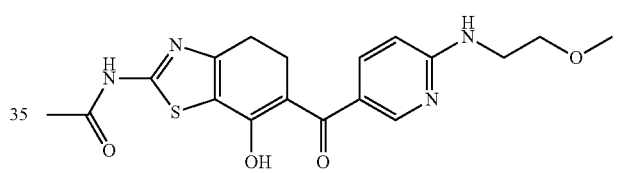

The title compound is obtained from 1.0 g (3.0 mmol) A-01 and 1.22 mL (14.1 mmol) 2-methoxyethylamine. The reaction is performed in a 1:1 mixture of THF and iPrOH according to the general procedure A4. For the work-up the solvent is removed under reduced pressure, the residue treated with water. The precipitate is filtered off, washed twice with water and dried. Yield: 1.03 g.

A-10) N-[6-(6-Ethylamino-pyridine-3-carbonyl)-7-hydroxy-4,5-dihydro-benzothiazol-2-yl]-acetamide

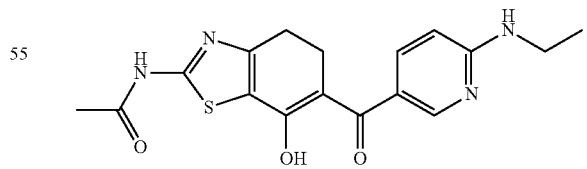

The title compound is obtained from 25.0 g (67.50 mmol, about 90% purity) A-01 and 25 mL (314 mmol) of a solution of ethylamine in water. The reaction is performed in a 1:1 mixture of THF and iPrOH according to the general procedure A4. For the work-up a large portion of the solvent is removed under reduced pressure, water is added and the formed precipitate is filtered off. The product is washed twice with both iPrOH and water. Yield: 20.2 g.

A-11) N-[6-(6-Ethylamino-5-methyl-pyridine-3-carbonyl)-7-hydroxy-4,5-dihydro-benzothiazol-2-yl]-acetamide

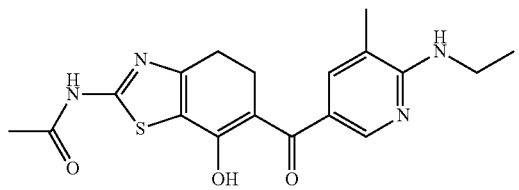

The title compound is obtained from 3.46 g (9.96 mmol) N-[6-(6-fluoro-5-methyl-pyridine-3-carbonyl)-7-hydroxy-4,5-dihydro-benzothiazol-2-yl]-acetamide (made in analogy to A-01) and 3.46 mL (43.5 mmol) of a solution of ethylamine in water. The reaction is performed in a 1:1 mixture of THF and iPrOH according to the general procedure A4. The crude product is used without further purification. Yield: 2.1 g.

A-12) N-[6-(6-Chloro-pyridine-3-carbonyl)-7-hydroxy-4,5-dihydro-benzothiazol-2-yl]-acetamide

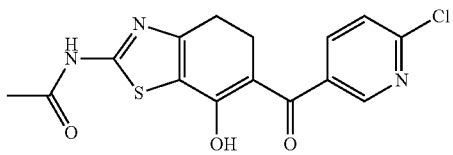

The title compound is obtained by reacting 3.34 g (15.9 mmol) N-(7-oxo-4,5,6,7-tetrahydro-benzothiazol-2-yl)-acetamide and 6.60 g (31.8 mmol) (6-chloro-pyridin-3-yl)-imidazol-1-yl-methanone according to the general procedure A3. The product is purified by RP-HPLC (gradient 5-70% ACN, 25 min, 60 mL/min). Yield: 570 mg.

A-13) N-[6-(5-Fluoro-pyridine-3-carbonyl)-7-hydroxy-4,5-dihydro-benzothiazol-2-yl]-acetamide

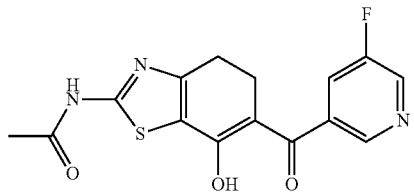

The title compound is obtained by reacting 500 mg (2.38 mmol) N-(7-oxo-4,5,6,7-tetrahydro-benzothiazol-2-yl)-acetamide and 909 mg (4.76 mmol) (5-fluoro-pyridin-3-yl)-imidazol-1-yl-methanone according to the general procedure A3. The reaction is quenched with 4 N HCl in dioxane prior to the addition of phosphate buffer (pH 6-7). The crude product obtained after extraction is used without further purification. Yield: 800 mg.

A-14) N-[7-Hydroxy-6-(5-methyl-pyridine-3-carbonyl)-4,5-dihydro-benzothiazol-2-yl]-acetamide

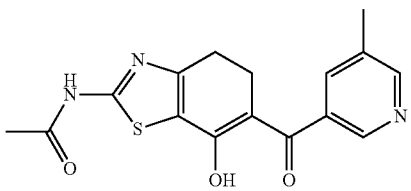

The title compound is obtained by reacting 786 mg (3.74 mmol) N-(7-oxo-4,5,6,7-tetrahydro-benzothiazol-2-yl)-acetamide and 1.40 g (7.48 mmol) of (5-methyl-pyridin-3-yl)-imidazol-1-yl-methanone according to the general procedure A3 (−60° C.). The reaction is quenched with HCl in ether (pH 3) before $CH_2Cl_2$ and phosphate buffer (28.1 g $NaH_2PO_4 \times 2H_2O$, 106.8 g $NaHPO_4 \times 2H_2O$, 500 mL $H_2O$) are added. The product is purified by RP-HPLC (gradient 5-80% ACN, 40 min). Yield: 439 mg.

A-15) N-[6-(6-Ethyl-pyridine-3-carbonyl)-7-hydroxy-4,5-dihydro-benzothiazol-2-yl]-acetamide

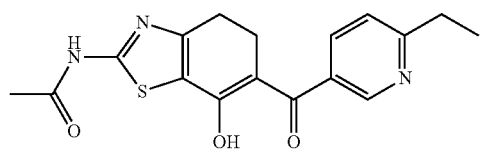

The title compound is obtained by reacting 21.0 g (210 mmol) N-(7-oxo-4,5,6,7-tetrahydro-benzothiazol-2-yl)-acetamide and 19.0 g (115 mmol) of 6-ethyl-nicotinic acid ethyl ester according to the general procedure A2. Yield: 26.4 g.

A-16) N-[7-Hydroxy-6-(6-isopropyl-pyridine-3-carbonyl)-4,5-dihydro-benzothiazol-2-yl]-acetamide

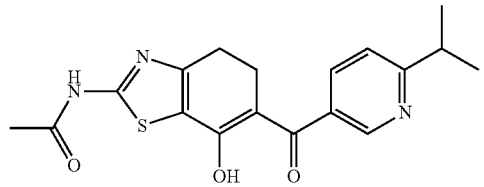

The title compound is obtained by reacting 1.67 g (7.92 mmol) N-(7-oxo-4,5,6,7-tetrahydro-benzothiazol-2-yl)-acetamide and 2.13 g (11.9 mmol) of 6-isopropyl-nicotinic acid ethyl ester according to the general procedure A2. Yield: 3.82 g.

A-17) N-[7-Hydroxy-6-(6-methoxy-pyridine-3-carbonyl)-4,5-dihydro-benzothiazol-2-yl]-acetamide

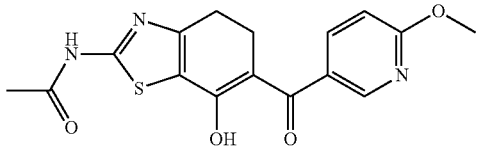

The title compound is obtained by reacting 3.36 g (16.0 mmol) N-(7-oxo-4,5,6,7-tetrahydro-benzothiazol-2-yl)-acetamide and 6.50 g (32.0 mmol) of the (6-methoxy-pyridin-3-yl)-imidazol-1-yl-methanone according to the general procedure A3. The reaction is quenched with saturated NH$_4$Cl solution prior to extraction. The product is purified by RP-chromatography (gradient: 5-70% ACN, 25 min, 60 mL/min). Yield: 860 mg.

A-18) N-[6-(5,6-Dimethyl-pyridine-3-carbonyl)-7-hydroxy-4,5-dihydro-benzothiazol-2-yl]-acetamide

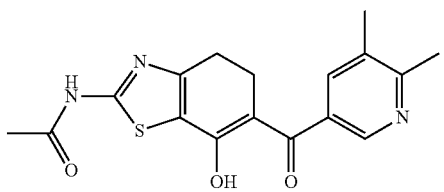

The title compound is obtained by reacting 5.00 g (23.8 mmol) N-(7-oxo-4,5,6,7-tetrahydro-benzothiazol-2-yl)-acetamide and 4.71 g (28.5 mmol) of 5,6-dimethylnicotinic acid methylester according to the general procedure A2. The product is purified by NP-HPLC (gradient DCM/MeOH 99:1-80:20, 20 min, 60 mL/min). Yield: 917 mg.

A-19) N-[7-Hydroxy-6-(quinoline-3-carbonyl)-4,5-dihydro-benzothiazol-2-yl]-acetamide

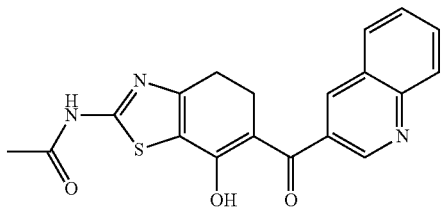

The title compound is obtained by reacting 1.67 g (7.95 mmol) N-(7-oxo-4,5,6,7-tetrahydro-benzothiazol-2-yl)-acetamide and 2.66 g (23.9 mmol) imidazol-1-yl-quinolin-3-yl-methanone according to the general procedure A3. A precipitate is formed during the reaction and is filtered off without quenching, washed with THF, dissolved in a mixture of saturated NaHCO$_3$-solution and CH$_2$Cl$_2$. The water phase is extracted with CH$_2$Cl$_2$, the combined organic phases are dried over MgSO$_4$, filtered, and the solvent is removed under reduced pressure. The remaining solid is treated with diethylether, filtered off and dried. Yield: 1.12 g.

A-20) N-[6-(6-Cyano-pyridine-3-carbonyl)-7-hydroxy-4,5-dihydro-benzothiazol-2-yl]-acetamide

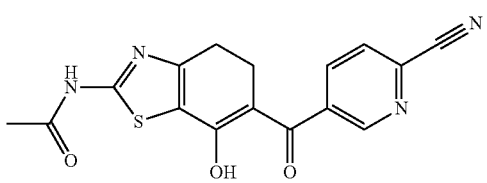

The title compound is obtained by reacting 1.91 g (9.08 mmol) N-(7-oxo-4,5,6,7-tetrahydro-benzothiazol-2-yl)-acetamide and 2.70 g (13.6 mmol) (6-cyano-pyridin-3-yl)-imidazol-1-yl-methanone according to the general procedure A3. The reaction is quenched by adding saturated NaHCO$_3$-solution. The water phase is extracted with CH$_2$Cl$_2$, the combined organic phases are dried over MgSO$_4$, filtered, and the solvent is removed under reduced pressure. The product is purified by RP-HPLC (gradient 5-80% ACN, 30 min, 60 mL/min). Yield: 149 mg.

A-23) N-[7-Hydroxy-6-(6-methyl-pyridine-3-carbonyl)-4,5-dihydro-benzothiazol-2-yl]-acetamide

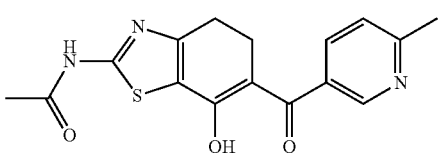

The title compound is obtained by reacting 3.82 g (18.2 mmol) N-(7-oxo-4,5,6,7-tetrahydro-benzothiazol-2-yl)-acetamide and 6.80 g (36.3 mmol) (6-methyl-pyrid-3-yl)-imidazol-1-yl-methanone according to the general procedure A3. The reaction is quenched by adding saturated NH$_4$Cl-solution. The water phase is extracted with CH$_2$Cl$_2$, the combined organic phases are dried over MgSO$_4$, filtered, and the solvent is removed under reduced pressure. The product is purified by RP-HPLC (gradient 5-70% ACN, 25 min, 60 mL/min). Yield: 4.68 g.

A-24) [7-Hydroxy-6-(6-methyl-pyridine-3-carbonyl)-4,5-dihydro-benzothiazol-2-yl]-carbamic acid methyl ester

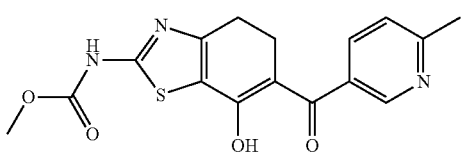

The title compound is obtained by reacting 12.7 g (56.3 mmol) (7-oxo-4,5,6,7-tetrahydro-benzothiazol-2-yl)-carbamic acid methyl ester and 13.7 g (73.2 mmol) (6-methyl-pyrid-3-yl)-imidazol-1-yl-methanone according to the general procedure A3. The product precipitates during the A-25) N-[7-Hydroxy-6-(6-methyl-pyridine-3-carbonyl)-4,5-dihydro-benzothiazol-2-yl]-propionamide

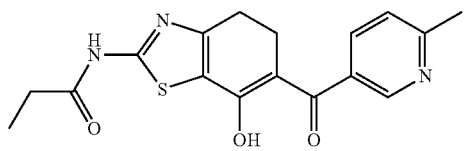

The title compound is obtained by reacting 4.10 g (18.3 mmol) N-(7-oxo-4,5,6,7-tetrahydro-benzothiazol-2-yl)-propionamide and 6.79 g (36.0 mmol) (6-methyl-pyrid-3-yl)-imidazol-1-yl-methanone according to the general procedure A3. After the complete addition a dark, sticky gum has formed. The THF is decanted of and the gum is dissolved in a saturated solution of NaHCO$_3$ in water. The mixture is extracted with CH$_2$Cl$_2$, the organic phases are washed with water and brine, dried on MgSO$_4$ and concentrated in vacuo. The residue is triturated with diethylether and ACN. Yield: 1.50 g.

A-26) (2-Chloro-7-hydroxy-4,5-dihydro-benzothiazol-6-yl)-(6-fluoro-pyridin-3-yl)-methanone

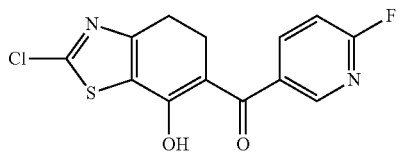

The title compound is obtained from 2.10 g (11.2 mmol) 2-chloro-5,6-dihydro-4H-benzothiazol-7-one and 1.83 g (11.4 mmol) 6-fluoronicotinic acid chloride according to general procedure A1. The crude product is taken up in DMSO, water and ACN are added. A precipitate is formed, filtered off and washed with water. Yield: 1.20 g.

A-27) (2-Amino-7-hydroxy-4,5-dihydro-benzothiazol-6-yl)-(6-methyl-pyridin-3-yl)-methanone

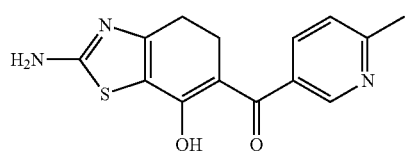

To a solution of 2.50 g A-23 in 20 mL dioxane are added 15 mL of 4 M solution of HCl in dioxane. The mixture is stirred for 2.5 h at 80° C. The solvent is removed under reduced pressure, the crude product is used without further purification.

A-28) [7-Hydroxy-6-(6-methylamino-pyridine-3-carbonyl)-4,5-dihydro-benzothiazol-2-yl]-carbamic acid methyl ester

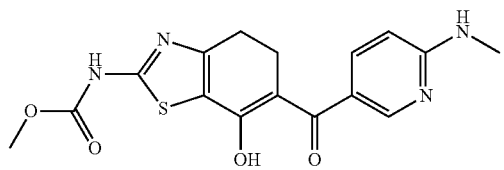

The title compound is obtained from 2.70 g (7.73 mmol) [7-hydroxy-6-(6-fluoro-pyridine-3-carbonyl)-4,5-dihydro-benzothiazol-2-yl]-carbamic acid methyl ester (which was made in analogy to A-01) and 2.7 mL (32.0 mmol) of a solution of methylamine in water. The reaction is performed in a 1:1 mixture of THF and iPrOH according to the general procedure A4. For the work-up the solvent is removed under reduced pressure, the precipitate is filtered and washed with iPrOH. Yield: 2.31 g.

A-29) (2-Cyclopropylamino-7-hydroxy-4,5-dihydro-benzothiazol-6-yl)-(6-methylamino-pyridin-3-yl)-methanone

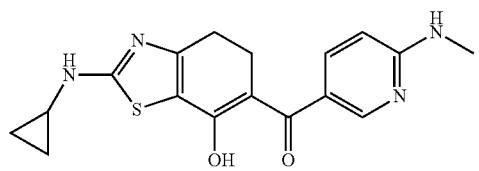

A solution of 200 mg (0.64 mmol) A-26 in THF is cooled to 0° C. A solution of methylamine in THF (1.6 mL, 2 M) is added and the mixture is stirred at 0° C. for 2 h and at RT for 2 h. Subsequently, 50 µL (0.72 mmol) cyclopropylamine are added and the mixture is stirred at RT for 18 h. The solvent is removed under reduced pressure. The crude product is used for the next step without further purification.

A-30) (7-Hydroxy-2-methylamino-4,5-dihydro-benzothiazol-6-yl)-(6-methylamino-pyridin-3-yl)-methanone

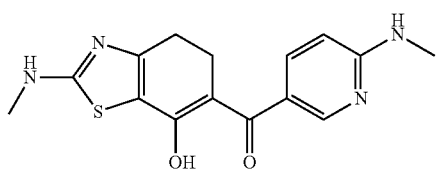

The title compound is obtained from 100 mg (0.32 mmol) A-26, 160 µL of a 2 M solution of methylamine in THF and 800 µL (1.60 mmol) of a 2 M solution of ethylamine in THF as outline for A-29. The product is purified by RP-HPLC. Yield: 33 mg.

A-31) Azetidine-1-carboxylic acid [7-hydroxy-6-(6-methyl-pyridine-3-carbonyl)-4,5-dihydro-benzothiazol-2-yl]-amide

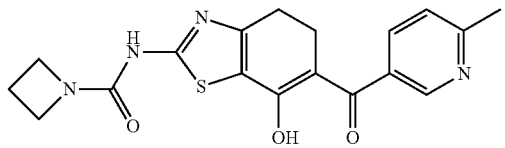

To a suspension of 2.0 g (5.33 mmol) (7-oxo-4,5,6,7-tetrahydro-benzothiazol-2-yl)-thiocarbamic acid S-ethyl ester (which was made in analogy to A-32) in 20 mL iPrOH are added DIPEA (2.74 mL, 16.0 mmol) and azetidin (540 µL, 8.0 mmol). The mixture is heated in the microwave for 30 min at 90° C. and for 30 min at 110° C. After removal of the solvent in vacuo the product is purified by RP-HPLC. Yield: 831 mg.

A-32) [6-(6-Fluoro-pyridine-3-carbonyl)-7-hydroxy-4,5-dihydro-benzothiazol-2-yl]-thiocarbamic acid S-ethyl ester

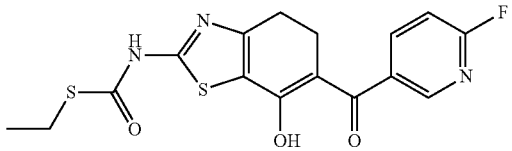

The title compound is obtained from 12.0 g (46.8 mmol) (7-oxo-4,5,6,7-tetrahydro-benzothiazol-2-yl)-thiocarbamic acid S-ethyl ester and 8.22 g (51.1 mmol) 6-fluoro-nicotinic acid chloride according to general procedure A1. The reaction is quenched with 25 mL 2 M hydrochloric acid and 100 mL phosphate buffer (pH 6). The crude product obtained after the extraction is treated with TBME. Yield: 18.5 g.

A-33) [7-Hydroxy-6-(6-methylamino-pyridine-3-carbonyl)-4,5-dihydro-benzothiazol-2-yl]-thiocarbamic acid S-ethyl ester

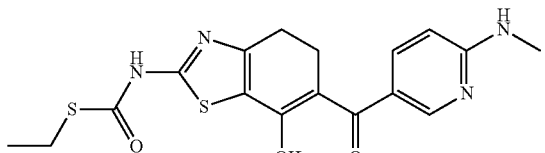

The title compound is obtained from 1.50 g (3.95 mmol) A-32 and 1.50 mL (19.8 mmol) of a solution of methylamine in water according to the general procedure A4. The reaction is performed in THF/iPrOH. After removal of the solvent in vacuo the remaining solid is treated with TBME. Yield 1.47 g.

A-34) [7-Hydroxy-6-(6-ethylamino-pyridine-3-carbonyl)-4,5-dihydro-benzothiazol-2-yl]-thiocarbamic acid S-ethyl ester

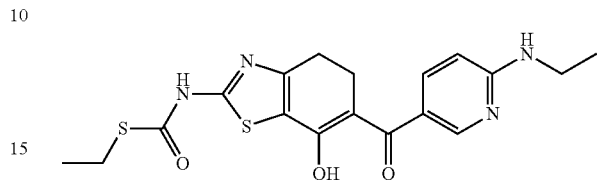

The title compound is obtained from 18.5 g (48.8 mmol) A-32 and 20.0 mL (247 mmol) of a solution of ethylamine in water according to the general procedure A4. The reaction is performed in THF/iPrOH at RT. Yield: 19.8 g.

A-35) [7-Hydroxy-6-(6-methyl-pyridine-3-carbonyl)-4,5-dihydro-benzothiazol-2-yl]-carbamic acid ethyl ester

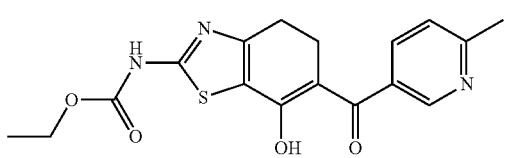

To a mixture of LiHMDS (1 M in THF, 48 mL) in 75 mL dry THF 3.90 g (16.2 mmol) (7-oxo-4,5,6,7-tetrahydro-benzothiazol-2-yl)-carbamic acid ethyl ester are added under argon atmosphere in small portions at −15° C. The mixture is stirred for 0.5 h and then the previously prepared solution of imidazol-1-yl-(6-methyl-pyridin-3-yl)-methanone is added dropwise. After the complete addition a dark, sticky gum has formed. The THF is decanted off and the gum is dissolved in a saturated solution of NaHCO₃ in water. The mixture is extracted with CH₂Cl₂, the organic phases are washed with water and brine, dried over MgSO₄ and concentrated in vacuo. The residue is triturated with ACN and dried in vacuo at 40° C. Yield: 4.45 g.

A-36) Ethyl-{5-[7-hydroxy-2-(3-methoxy-propionylamino)-4,5-dihydro-benzothiazole-6-carbonyl]-pyridin-2-yl}-carbamic acid tert-butyl ester

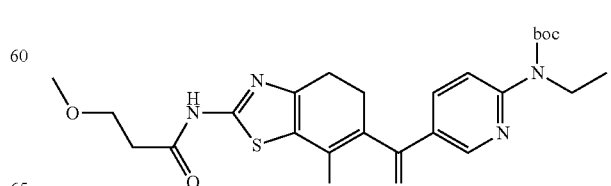

A-36a)
6-(tert-Butoxycarbonyl-ethyl-amino)-nicotinic acid

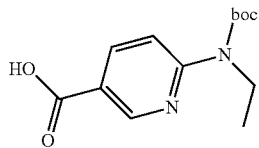

6-Chloro-nicotinic acid methyl ester (60 g, 0.35 mol) is taken up in 500 mL 2 M ethyl-amine in THF and stirred at 100° C. in a sealed tube for 16 h. The reaction mixture is cooled to RT and the solvents are removed under reduced pressure. The residue is poured on ice and stirred for 15 min. The precipitate is filtered off, washed with water and dried in vacuo. The dried 6-ethylamino-nicotinic acid methyl ester (30 g, 0.17 mol) is dissolved in 150 mL DCM and triethylamine (29 mL, 0.20 mol), DMAP (4.0 g, 33 mmol) and BOC anhydride (100 mL, 0.42 mol) are added successively at 0° C. The reaction mixture is allowed to warm up to RT and stirred for 16 h. To the reaction mixture 100 mL of 10% citric acid in water is added and the reaction mixture is stirred for 10 min. The organic phase is separated, dried over Na₂SO₄ and concentrated under reduced pressure. Yield: 60 g.

The crude 6-(tert-butoxycarbonyl-ethyl-amino)-nicotinic acid methyl ester is taken up in 100 mL dioxane and a solution of lithium hydroxide monohydrate (13.5 g, 0.32 mol) in 100 mL water is added and the reaction mixture is stirred at RT for 4 h. The dioxane is removed from the reaction mixture under reduced pressure, water is added and the reaction mixture is acidified to pH 6 with a solution of 10% citric acid in water. The formed precipitate is filtered off and dried in vacuo. Yield: 36 g. $^1$H NMR (DMSO-d6): δ 13.2 (s, 1H), 8.8 (s, 1H), 8.2 (d, 1H), 7.8 (d, 1H), 4.0 (quart, 2H), 1.5 (s, 9H), 1.2 (t, 3H).

A-36b) (5-Chlorocarbonyl-pyridin-2-yl)-ethyl-carbamic acid tert-butyl ester

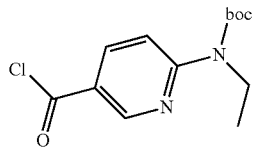

A-36a (6.40 g, 24.0 mmol) is taken up in 150 mL DCE, 1-chloro-N,N-2-trimethylpropenylamine (6.42 mL, 48.1 mmol) is added and the reaction mixture is stirred overnight at RT. The reaction mixture is concentrated under reduced pressure and the crude product is used in the next step without purification.

A-36c) 3-Methoxy-N-(7-oxo-4,5,6,7-tetrahydro-benzothiazol-2-yl)-propionamide

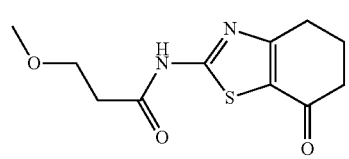

To a mixture of 2-amino-5,6-dihydro-4H-benzothiazol-7-one (3.0 g, 18 mmol) and DBU (5.3 mL, 36 mmol) in 100 mL acetonitrile is added a solution of 1-imidazol-1-yl-3-methoxy-propan-1-one (6.9 g, 45 mmol) in acetonitrile. The reaction mixture is stirred for 15 min at RT and then concentrated under reduced pressure. The residue is poured in water, acidified to pH 5 with 6 M aqueous HCl and the product is extracted with ethyl acetate. The combined organic phases are dried over MgSO₄ and concentrated under reduced pressure. Yield: 3.8 g. The product is used in the next step without purification. A-36 is synthesized according to general procedure A1 starting from 3.8 g (15 mmol) A-36c and 6.8 g (24 mmol) A-36b. Yield: 1.23 g.

A-37) 4-Dimethylamino-N-[6-(6-ethylamino-pyridine-3-carbonyl)-7-hydroxy-4,5-dihydro-benzothiazol-2-yl]-butyramide

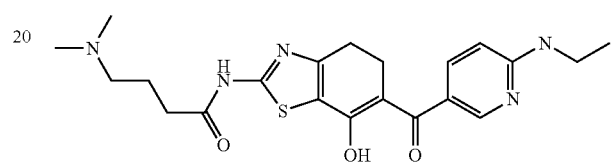

A-37a) (2-Amino-7-hydroxy-4,5-dihydro-benzothiazol-6-yl)-(6-ethylamino-pyridin-3-yl)-methanone

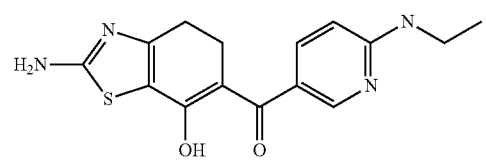

To a mixture of 4.0 g (11 mmol) A-10 in 12 mL dioxane is added 8.8 mL conc. HCl and the reaction mixture is stirred for 2 h at 95° C. The reaction mixture is concentrated under reduced pressure and the residue is triturated with methanol and dried in vacuo at 40° C. Yield: 3.7 g.

To a mixture of 3.7 g (11 mmol) A-37a in 45 mL acetonitrile is added 3.5 mL (23 mmol) DBU and the reaction mixture is stirred for 10 min. at RT. Then a solution of 5.3 g (29 mmol) 4-dimethylamino-1-imidazol-1-yl-butan-1-one in acetonitrile is added and the reaction mixture is stirred for 2 h at 100° C. and overnight at 60° C. The reaction mixture is concentrated under reduced pressure and the product is purified by HPLC (C-18, 2-70% acetonitrile in water). Yield: 2.9 g.

A-38) N-tert-Butoxycarbonyl-[5-(2-acetylamino-7-hydroxy-4,5-dihydro-benzothiazole-6-carbonyl)-pyridin-2-yl]-carbamic acid tert-butyl ester

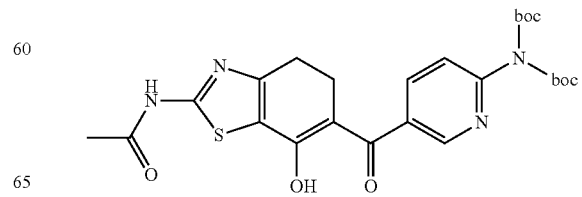

A-38a)
6-[N,N-Di-(tert-butoxycarbonyl)-amino]-nicotinic acid

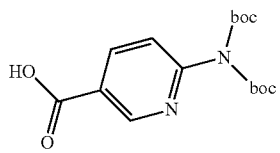

6-Amino-nicotinic acid methyl ester (13.7 g, 90.0 mmol), triethyl amine (12.5 mL, 90.0 mmol) and DMAP (3.30 g, 27.0 mmol) are taken up in 200 mL DCM and a solution of di-tert-butyl dicarbonate (41.3 g, 189 mmol) in 40 mL DCM is added drop wise. The reaction mixture is stirred overnight at RT. An aqueous 5% $KHSO_4$ solution is added and the reaction mixture is extracted with DCM. The combined organic phases are washed with an aqueous 50% saturated $KHCO_3$ solution, dried over $MgSO_4$ and concentrated under reduced pressure. Yield: 34.9 g.

Of this residue 17.3 g is taken up in a mixture of 150 mL MeOH and 300 mL water, lithium hydroxide (2.33 g, 97.3 mmol) is added and the reaction mixture is stirred for 3 h at RT. The reaction mixture is acidified to pH 4 with acetic acid and the formed precipitate is filtered off, washed with water and dried in vacuo. Yield: 11.8 g. $^1H$ NMR (DMSO-d6): δ 9.0 (s, 1H), 8.2 (d, 1H), 7.2 (d, 2H), 1.4 (s, 18H).

A-38b) N-tert-Butoxycarbonyl-(5-chlorocarbonyl-pyridin-2-yl)-carbamic acid tert-butyl ester

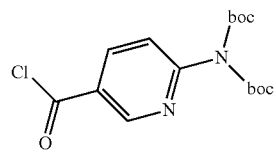

A-38a (5.00 g, 14.8 mmol) is dried by azeotropic distillation with toluene and then taken up in 20 mL dry THF and cooled to 0° C. 1-Chloro-N,N-2-trimethylpropenyl-amine (3.95 g, 30.0 mmol) is added drop wise and the reaction mixture is stirred at RT for 3 h. The reaction mixture is concentrated under reduced pressure and the crude product is used in the next step without purification.

A-38 is synthesized according to general procedure A1 starting from 8.0 g (38 mmol) N-(7-oxo-4,5,6,7-tetrahydro-benzothiazol-2-yl)-acetamide and 21.7 g (61 mmol) A-38b. Yield: 10.9 g.

A-39) N-[6-(6-Ethylamino-pyridine-3-carbonyl)-7-hydroxy-4,5-dihydro-benzothiazol-2-yl]-3-(1-methyl-1H-imidazol-2-yl)-propionamide

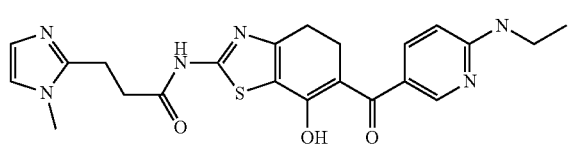

Example A-39 is prepared analogously to example A-37 starting from 0.30 g (0.95 mmol) A-37a, 0.21 mL (1.4 mmol) DBU and 0.48 g (2.4 mmol) 1-imidazol-1-yl-3-(1-methyl-1H-imidazol-2-yl)-propan-1-one. Yield: 66 mg.

A-40) {[6-(6-Ethylamino-pyridine-3-carbonyl)-7-hydroxy-4,5-dihydro-benzothiazol-2-ylcarbamoyl]-methyl}-methyl-carbamic acid tert-butyl ester

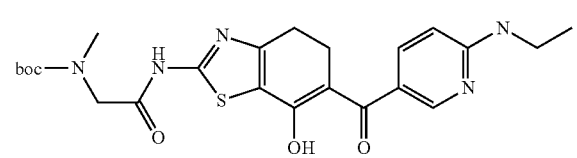

Example A-40 is prepared analogously to example A-37 starting from 0.30 g (0.95 mmol) A-37a, 0.21 mL (1.4 mmol) DBU and 0.57 g (2.4 mmol) (2-imidazol-1-yl-2-oxo-ethyl)-methyl-carbamic acid tert-butyl ester. Yield: 0.16 g.

A-41) {[6-(6-Ethylamino-pyridine-3-carbonyl)-7-hydroxy-4,5-dihydro-benzothiazol-2-ylcarbamoyl]-methyl}-carbamic acid tert-butyl ester

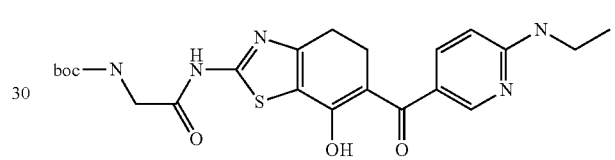

Example A-41 is prepared analogously to example A-37 starting from 0.30 g (0.95 mmol) A-37a, 0.21 mL (1.4 mmol) DBU and 0.53 g (2.4 mmol) (2-imidazol-1-yl-2-oxo-ethyl)-carbamic acid tert-butyl ester. Yield: 0.19 g.

A-42) 2-Dimethylamino-N-[6-(6-ethylamino-pyridine-3-carbonyl)-7-hydroxy-4,5-dihydro-benzothiazol-2-yl]-acetamide

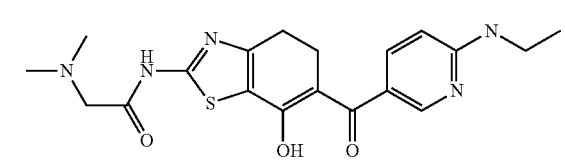

Example A-42 is prepared analogously to example A-37 starting from 0.30 g (0.95 mmol) A-37a, 0.21 mL (1.4 mmol) DBU and 0.36 g (2.4 mmol) 2-dimethylamino-1-imidazol-1-yl-ethanone. Yield: 0.20 g.

A-43) [7-Hydroxy-6-(6-methyl-pyridine-3-carbonyl)-4,5-dihydro-benzothiazol-2-yl]-carbamic acid 3-methoxy-propyl ester

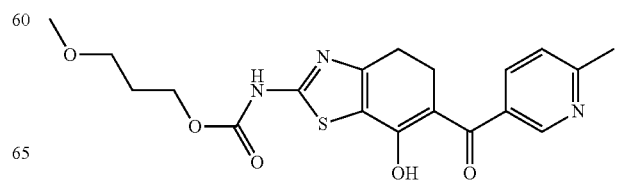

A mixture of 0.30 g (1.0 mmol) A-27, 0.42 g (2.6 mmol) CDI and 0.31 mL (2.1 mmol) DBU is stirred at 100° C. for 8 h. Then 0.50 mL (5.2 mmol) 3-methoxy-1-propanol is added and the reaction mixture is stirred at 100° C. overnight. The reaction mixture is concentrated under reduced pressure and the product is purified by HPLC (C-18, 5-80% acetonitrile in water). Yield: 87 mg.

A-44) [7-Hydroxy-6-(6-methyl-pyridine-3-carbonyl)-4,5-dihydro-benzothiazol-2-yl]-carbamic acid tetrahydro-furan-2-ylmethyl ester

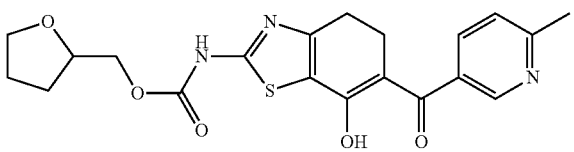

Example A-44 is prepared analogously to example A-43 starting from 0.30 g (1.0 mmol) A-27, 0.42 g (2.6 mmol) CDI, 0.31 mL (2.1 mmol) DBU and 0.50 mL (5.2 mmol) tetrahydrofurfuryl alcohol. Yield: 0.14 g.

A-45) [7-Hydroxy-6-(6-methyl-pyridine-3-carbonyl)-4,5-dihydro-benzothiazol-2-yl]-carbamic acid tetrahydro-furan-3-ylmethyl ester

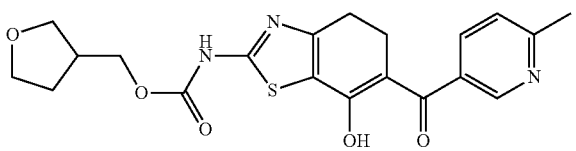

Example A-45 is prepared analogously to example A-43 starting from 0.30 g (1.0 mmol) A-27, 0.42 g (2.6 mmol) CDI, 0.31 mL (2.1 mmol) DBU and 0.50 mL (5.2 mmol) (tetrahydro-furan-3-yl)-methanol. Yield: 83 mg.

A-46) N-tert-Butoxycarbonyl-{5-[2-(3,3-dimethyl-ureido)-7-hydroxy-4,5-dihydro-benzothiazole-6-carbonyl]-pyridin-2-yl}-carbamic acid tert-butyl ester

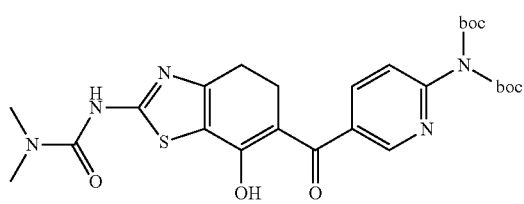

A-46a) 1,1-Dimethyl-3-(7-oxo-4,5,6,7-tetrahydro-benzothiazol-2-yl)-urea

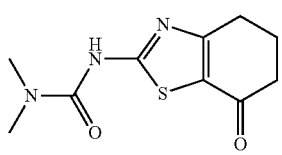

A mixture of 2-amino-5,6-dihydro-4H-benzothiazol-7-one (10 g, 59 mmol), DBU (18 mL, 0.12 mol) and CDI (24 g, 0.15 mol) in 400 mL acetonitrile is stirred for 5 h at 100° C. Then dimethylamine (150 mL, 2M in THF) is added and the reaction mixture is stirred overnight at 100° C. The reaction mixture is concentrated under reduced pressure and the residue is poured in water. The mixture is acidified to pH 5 with 6 M HCl in water and extracted with ethyl acetate. The combined organic phases are dried over MgSO$_4$ and concentrated under reduced pressure. The residue is triturated with diethyl ether. Yield: 9.1 g.

Example A-46 is synthesized according to general procedure A1 starting from 0.20 g (2.5 g, 10 mmol) A-46a and 6.0 g (17 mmol) A-38b. Yield: 2.5 g.

A-47) N-[6-(6-Amino-pyridine-3-carbonyl)-7-hydroxy-4,5-dihydro-benzothiazol-2-yl]-4-dimethylamino-butyramide

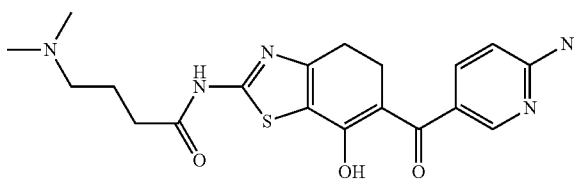

A-47a) (2-Amino-7-hydroxy-4,5-dihydro-benzothiazol-6-yl)-(6-amino-pyridin-3-yl)-methanone

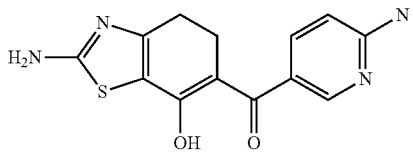

A-47a is prepared analogously to example A-37a starting from 4.0 g (7.6 mmol) A-38. Yield: 2.7 g.

Example A-47 is prepared analogously to example A-37 starting from 2.0 g (6.9 mmol) A-47a, 2.1 mL (14 mmol) DBU and 3.1 g (17 mmol) 4-dimethylamino-1-imidazol-1-yl-butan-1-one. Yield: 1.9 g.

A-48) 1-[6-(6-Ethylamino-pyridine-3-carbonyl)-7-hydroxy-4,5-dihydro-benzothiazol-2-yl]-3-methyl-urea

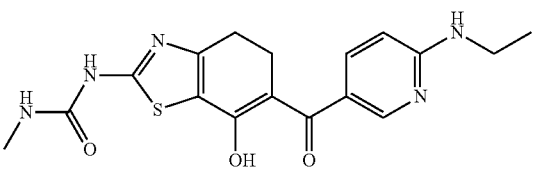

A solution of 5.00 g (12.4 mmol) A-34 in 30 mL of a 2 M solution of methylamine in methanol is heated at 100° C. for 20 min. The solvent is removed under reduced pressure and the crude reaction product is used without further purification in the next step.

A-49) 1-[6-(6-Ethylamino-pyridine-3-carbonyl)-7-hydroxy-4,5-dihydro-benzothiazol-2-yl]-urea

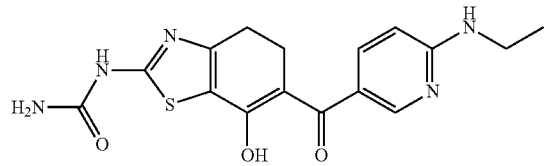

A solution of 0.90 g (2.2 mmol) A-34 in 5.5 mL of a 2 M solution of ammonia in methanol is heated at 100° C. for 30 min. The solvent is removed under reduced pressure and the crude reaction product is used without further purification in the next step.

A-50) 1-[6-(6-Ethylamino-pyridine-3-carbonyl)-7-hydroxy-4,5-dihydro-benzothiazol-2-yl]-3-ethyl-urea

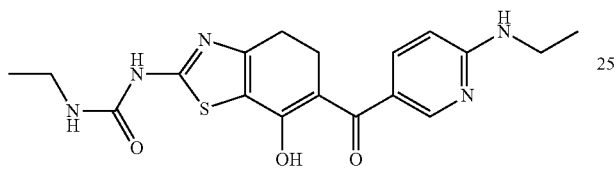

A solution of 450 mg (1.1 mmol) A-34 in 2.8 mL of a 2 M solution of ethylamine in THF is heated at 120° C. for 20 min. The solvent is removed under reduced pressure and the crude reaction product is used without further purification in the next step.

A-51) 1-(2-Dimethylamino-ethyl)-3-[6-(6-ethylamino-pyridine-3-carbonyl)-7-hydroxy-4,5-dihydro-benzothiazol-2-yl]-urea

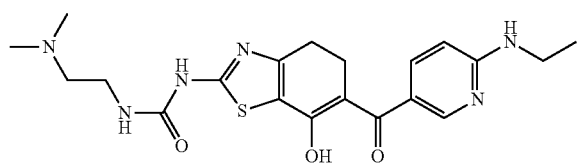

A solution of 400 mg (0.99 mmol) A-34 and 545 µL (4.94 mmol) N,N-dimethyl-ethylene-diamine in 2 mL THF is heated at 120° C. for 20 min. The solvent is removed under reduced pressure and the crude reaction product is used without further purification in the next step.

A-52) 1-[6-(6-Ethylamino-pyridine-3-carbonyl)-7-hydroxy-4,5-dihydro-benzothiazol-2-yl]-3-(2-methoxy-ethyl)-urea

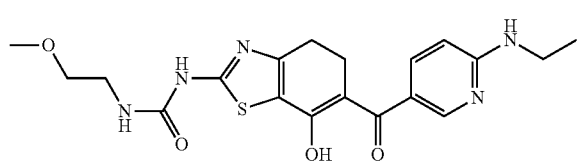

A solution of 300 mg (0.74 mmol) A-34 and 322 µl (3.71 mmol) 2-methoxy-ethylamine in 3 mL THF is heated at 120° C. for 20 min. The solvent is removed under reduced pressure and the crude reaction product is used without further purification in the next step.

A-53) 1-(3-Dimethylamino-propyl)-3-[6-(6-ethylamino-pyridine-3-carbonyl)-7-hydroxy-4,5-dihydro-benzothiazol-2-yl]-urea

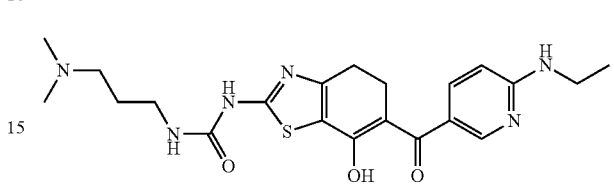

A solution of 300 mg (0.74 mmol) A-34 and 467 µL (3.71 mmol) N,N-dimethyl-1,3-propenediamine in 3 mL THF is heated at 120° C. for 20 min. The solvent is removed under reduced pressure and the crude reaction product is used without further purification in the next step.

A-54) 1-[6-(6-Ethylamino-pyridine-3-carbonyl)-7-hydroxy-4,5-dihydro-benzothiazol-2-yl]-3-(3-methoxy-propyl)-urea

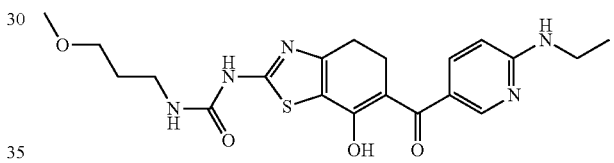

A solution of 300 mg (0.74 mmol) A-34 and 378 µL (3.71 mmol) 3-methoxy-propylamine in 3 mL THF is heated at 120° C. for 20 min. The solvent is removed under reduced pressure and the crude reaction product is used without further purification in the next step.

A-55) 1-(3-Dimethylamino-propyl)-3-[7-hydroxy-6-(6-methyl-pyridine-3-carbonyl)-4,5-dihydro-benzothiazol-2-yl]-urea

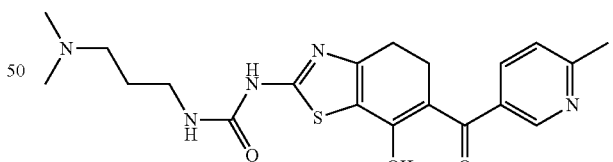

To a suspension of 2.0 g (6.96 mmol) A-27 and 2.26 g (13.9 mmol) CDI in 7 mL acetonitrile is added 1.0 mL (6.52 mmol) DBU. The reaction mixture is heated for 10 min at 90° C. in the microwave. 1.56 g (15.3 mmol) N,N-dimethyl-1,3-propanediamine is added and the reaction mixture is heated for 10 min at 120° C. in the microwave. DCM and water are added and the mixture is adjusted to pH 1 with concentrated HCl solution. After phase separation the aqueous phase is washed five times with DCM. The aqueous phase is evaporated and the residue is taken up in DMSO. Purification is performed via preparative RP-HPLC. After removal of the solvent 350 mg (0.84 mmol) of the desired compound are obtained.

Intermediates B

Hydrazines

B-01) 3-Chloro-4-hydrazino-N,N-dimethyl-benzamide hydrochloride

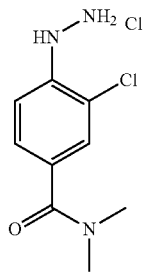

B-01a) 3-Chloro-4-fluoro-N,N-dimethyl-benzamide

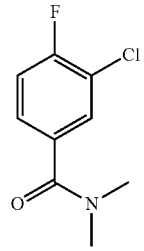

To a mixture of 3-chloro-4-fluorobenzoic acid (20.0 g, 115 mmol) in 100 mL THF is added carbonyldiimidazole (20.0 g, 126 mmol) and the reaction mixture is stirred at RT for 0.5 h. Then dimethylamine (1 M in THF, 171 mL) is added and the reaction mixture is stirred for another h. The reaction mixture is concentrated in vacuo, re-dissolved in DCM, washed with saturated aqueous sodium carbonate and brine and concentrated in vacuo. Yield: 20.0 g.

Hydrazine hydrate (150 mL, 4.96 mol) is added to a mixture of B-01a (20.0 g, 99.3 mmol) in 100 mL dioxane and the reaction mixture is stirred at reflux temperature for 16 h. The reaction mixture is concentrated in vacuo, DCM is added and the reaction mixture washed with water and brine, dried over sodium sulfate and concentrated in vacuo. The residue is dissolved in dioxane, cooled to 0° C. and hydrochloric acid (4 M in dioxane, 25 mL) is added. The reaction mixture is stirred for 1 h and then concentrated in vacuo. The residue is triturated with diethyl ether. Yield: 21 g.

B-02) 4-Hydrazino-N,N-dimethyl-benzamide

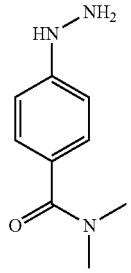

B-02a) 4-Nitro-N,N-dimethyl-benzamide

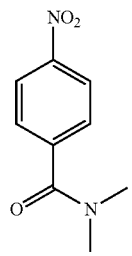

To a mixture of 4-nitrobenzoyl chloride (7.20 g, 38.8 mmol) and dimethylamine hydrochloride (3.20 g, 39.2 mmol) in 100 mL DCM is added triethyl amine (14.0 mL, 99.6 mmol) at 0° C. The cooling bath is removed and the reaction mixture is stirred overnight at RT. Then 300 mL DCM is added and the reaction mixture is washed with 50% saturated aqueous ammonium chloride, water, 50% saturated aqueous sodium hydrogen carbonate and 0.1 M aqueous NaOH. The organic phase is dried over $MgSO_4$ and concentrated in vacuo. Yield: 5.37 g.

B-02b) 4-Amino-N,N-dimethyl-benzamide

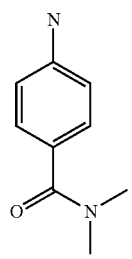

B-02a (2.0 g, 10.3 mmol) is dissolved in 120 mL MeOH and 10% palladium on coal (200 mg) is added. The reaction mixture is stirred for 2 h under an atmosphere of 4 bar hydrogen. The reaction mixture is filtered and concentrated in vacuo. Yield: 1.69 g. To a mixture of B-02b (1.68 g, 10.2 mmol) in 30 mL concentrated hydrochloric acid at −10° C. is added a solution of sodium nitrite (755 mg, 10.9 mmol) in 7 mL water. The reaction mixture is stirred for 1 h at 0° C. and then at −5° C. a solution of tin(II) chloride dehydrate (4.81 g, 21.4 mmol) in 10 mL concentrated HCl is added. The cooling bath is removed and the reaction mixture is stirred for 1 h at RT. The reaction mixture is basified with 8 M aqueous sodium hydroxide and extracted with ethyl acetate. The combined organic phases are dried over $MgSO_4$ and concentrated in vacuo. The residue is taken up in diethyl ether and 2 M HCl in diethyl ether is added until no more precipitate is formed. The precipitate is filtered of and dried in vacuo at 40° C. Yield: 213 mg.

B-03) [3-Fluoro-4-(2-morpholin-4-yl-ethoxy)-phenyl]-hydrazine hydrochloride

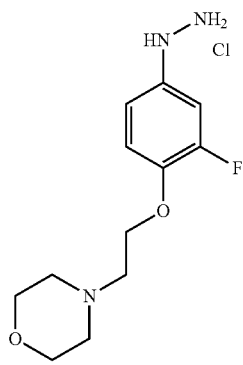

B-03a) 4-[2-(4-Bromo-2-fluoro-phenoxy)-ethyl]-morpholine

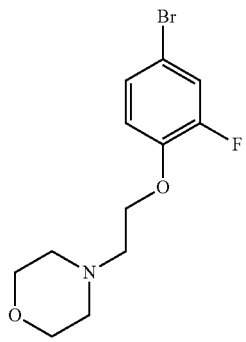

4-Bromo-2-fluorophenol (16.7 g, 87.4 mmol) is dissolved in 100 mL DMF. N-(2-Chloro-ethyl)morpholine hydrochloride (18.5 g, 99.4 mmol), potassium carbonate (28.0 g, 203 mmol) and potassium iodide (100 mg, 0.602 mmol) are added and the reaction mixture is stirred for 3 h at 65° C. The reaction mixture is poured in water and extracted with ethyl acetate. The combined organic phases are washed with water and brine, dried over magnesium sulfate and concentrated in vacuo. Yield: 27.7 g.

B-03b) N-Benzhydrylidene-N'-[3-fluoro-4-(2-morpholin-4-yl-ethoxy)-phenyl]-hydrazine

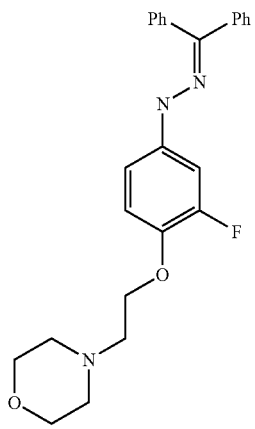

B-03a (27.7 g, 91.1 mmol) is dissolved in 300 mL toluene, degassed and added under argon atmosphere dropwise to a mixture of benzophenone hydrazone (18.8 g, 95.8 mmol), sodium tert-butoxide (13.1 g, 136 mmol), BINAP (2.0 g, 3.21 mmol) and palladium(II) acetate (400 mg, 1.78 mmol). The reaction mixture is warmed to 100° C. and stirred for 2 h. Active charcoal is added and reaction mixture is filtered over Celite. The filtrate is concentrated in vacuo and the residue is purified by flash chromatography (silica gel, 0-10% MeOH in DCM) followed by trituration with MeOH. Yield: 27.6 g.

B-03b (27.6 g, 65.7 mmol) is dissolved in 50 mL n-propanol and 50 mL concentrated hydrochloric acid is added. The reaction mixture is stirred at 120° C. for 3 h and then concentrated in vacuo. The residue is taken up in fresh n-propanol, concentrated in vacuo again, triturated with DCM and dried in vacuo. Yield: 17.3 g.

B-04) [1-(4-Hydrazino-phenyl)-cyclopropyl]-dimethyl-amine

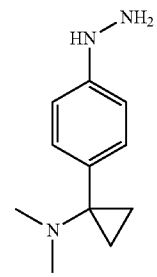

The compound is prepared according to WO 2007/113246.

B-05) 2-Fluoro-4-hydrazino-N,N-dimethyl-benzamide

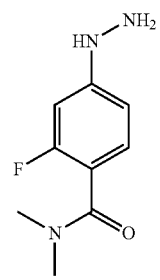

B-05a) 2-Fluoro-4-nitro-benzoyl chloride

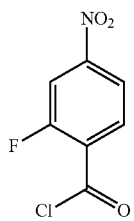

To a solution of 2-fluoro-4-nitrobenzoic acid (5.0 g, 27.0 mmol) in 70 mL DCM is added thionyl chloride (12.1 mL, 162 mmol). The reaction mixture is stirred at 50° C. for 1.5 h and overnight at RT. The reaction mixture is concentrated in vacuo, the residue is taken up in fresh DCM and concentrated in vacuo again. Yield: 5.12 g.

B-05b) 2-Fluoro-N,N-dimethyl-4-nitro-benzamide

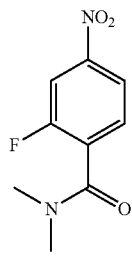

B-05a (5.12 g, 25.2 mmol) is dissolved in 60 mL THF and cooled to 0° C. DIPEA (5.17 ml, 30.2 mmol) is added followed by a 2 M solution of methyl amine in THF (12.6 mL, 25.2 mmol) and the reaction mixture is stirred overnight at RT. Then 20 mL of a saturated aqueous sodium bicarbonate solution is added and the reaction mixture is extracted with ethyl acetate. The combined organic phases are washed with saturated aqueous sodium hydrogen carbonate solution, dried over magnesium sulfate and concentrated in vacuo. Yield: 1.94 g.

B-05c) 4-Amino-2-fluoro-N,N-dimethyl-benzamide

A mixture of B-05b (1.94 g, 9.13 mmol) and 10% Pd on coal (194 mg) in 50 mL MeOH is stirred overnight at RT under an atmosphere of 5 bar hydrogen. The reaction mixture is filtered and concentrated in vacuo. Yield: 1.40 g.

B-05c (1.40 g, 7.68 mmol) is dissolved in 20 mL concentrated HCl and cooled to −10° C. Slowly a solution of sodium nitrite (1.36 g, 11.5 mmol) in 10 mL water is added and the reaction mixture is stirred for 4 h. A solution of tin(II)chloride dihydrate (6.94 g, 30.7 mmol) in 10 mL concentrated HCl is added and the reaction mixture is stirred overnight at RT. The reaction mixture is cooled to 0° C., basified with 10 M aqueous NaOH and extracted with chloroform. The combined organic phases are washed with water, dried over MgSO$_4$ and concentrated in vacuo. Yield: 1.0 g.

B-06) (2-Methyl-2,3-dihydro-1H-isoindol-5-yl)-hydrazine hydrochloride

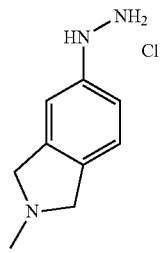

B-06a) 5-Bromo-2-methyl-isoindole-1,3-dione

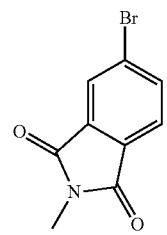

A mixture of 3-bromophthalimide (10.0 g, 44.2 mmol), potassium carbonate (12.2 g, 88.5 mmol) and potassium iodide (50 mg, 0.30 mmol) are stirred in 80 mL DMF for 15 min. The reaction mixture is cooled to 0° C., methyl iodide (3.04 mL, 48.7 mmol) is added and the reaction mixture is stirred overnight at RT. The reaction mixture is filtered, the solids are washed with DMF and the filtrate is poured in water. The mixture is extracted with ethyl acetate and the combined organic phases are washed several times with water, dried over MgSO$_4$ and concentrated in vacuo. Yield: 7.10 g.

B-06b) 5-Bromo-2-methyl-2,3-dihydro-1H-isoindole

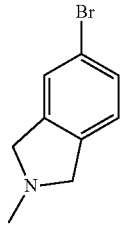

B-06a (5.8 g, 24.2 mmol) is dissolved in 60 mL THF and cooled to 0° C. Borane dimethylsulfide complex (9.18 mL, 121 mmol) is added and the reaction mixture is warmed to RT. The reaction mixture is stirred overnight at reflux temperature. Additional borane dimethyl sulfide complex (9.18 mL, 121 mmol) is added and the reaction mixture is stirred for another 20 h at reflux temperature. The reaction mixture is cooled to RT, 40 mL MeOH and 12 mL conc. HCl are added and the reaction mixture is stirred overnight at 80° C. The reaction mixture is concentrated in vacuo, the residue is taken up in ethyl acetate and washed with saturated aqueous sodium hydrogen carbonate solution. The water phase is extracted with ethyl acetate, the combined organic phases are dried over Na$_2$SO$_4$ and concentrated in vacuo. Yield: 4.56 g.

B-06c) N-Benzhydrylidene-N'-(2-methyl-2,3-dihydro-1H-isoindol-5-yl)-hydrazine

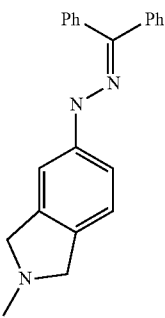

B-06c is prepared analogously to B-03b starting from B-06b (3.5 g, 16.5 mmol), benzophenone hydrazone (3.24 g, 16.5 mmol), sodium tert-butoxide (2.38 g, 24.8 mmol), (2-biphenyl)-di-tert-butylphosphine (246 mg, 0.825 mmol) and palladium(II) acetate (111 mg, 0.495 mmol). Yield: 1.25 g.

B-06 is prepared analogously to B-03 starting from B-06c (1.55 g, 4.73 mmol). Yield: 620 mg.

B-07) (4-Hydrazino-benzyl)-dimethyl-amine hydrochloride

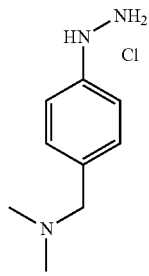

B-07a) (4-Bromo-benzyl)-dimethyl-amine

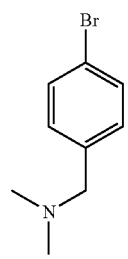

At 5° C. 4-bromobenzylbromide (100 g, 402 mmol) in 100 mL DMF is added to a mixture of dimethylamine (40% in water, 150 mL, 1.33 mol). After 0.5 h stirring at RT, 6 M aqueous HCl is added and the reaction mixture is extracted with diethyl ether. The combined organic phases are washed with brine, dried over Na$_2$SO$_4$ and concentrated in vacuo. The residue is purified by vacuum distillation (bp 58° C. at 2 mbar). Yield: 77.6 g.

B-07b) [4-(N'-Benzhydrylidene-hydrazino)-benzyl]-dimethyl-amine

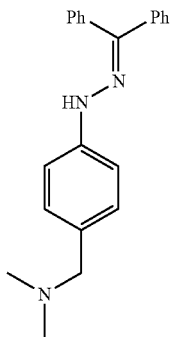

B-07b is prepared analogously to B-03b starting from B-07a (77.6 g, 362 mmol), benzophenone hydrazone (71.0 g, 362 mmol), sodium tert-pentoxide (59.8 g, 543 mmol), BINAP (5.12 mg, 8.20 mmol) and palladium(II)acetate (1.38 g, 6.16 mmol). Yield: 122 g. The product is purified by treatment with active coal in n-propanol.

B-07 is prepared analogously to B-03 starting from B-07b (122 g, 362 mmol). Yield: 57.6 g.

B-08) 2-(4-Hydrazino-phenyl)-ethanol

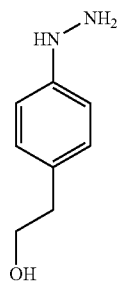

B-08 is prepared analogously to B-05 starting from 4-aminophenethyl alcohol (7.3 g, 53.2 mmol), sodium nitrite (3.7 g, 53.6 mmol) and tin(II) chloride dihydrate (50.0 g, 222 mmol). Yield: 3.70 g.

B-09) (4-Fluoro-3-morpholin-4-ylmethyl-phenyl)-hydrazine hydrochloride

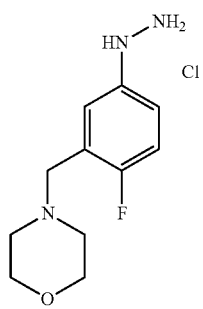

B-09a) 4-(5-Bromo-2-fluoro-benzyl)-morpholine

5-Bromo-2-fluorobenzaldehyde (2.5 g, 12.3 mmol) and morpholine (1.62 g, 18.5 mmol) are dissolved in 50 mL DCE and stirred for 0.5 h. Acetic acid (0.42 mL, 7.4 mmol) and sodium trisacetoxyboronhydride (3.92 g, 18.5 mmol) are added and the reaction mixture is stirred for 2 h. Then 50 mL of a saturated aqueous solution of sodium hydrogencarbonate is added and the reaction mixture is stirred for another 0.5 h. The reaction mixture is extracted with DCM and the combined organic phases are dried over MgSO$_4$ and concentrated in vacuo. Yield: 3.02 g.

B-09b) N-Benzhydrylidene-N'-(4-fluoro-3-morpholin-4-ylmethyl-phenyl)-hydrazine

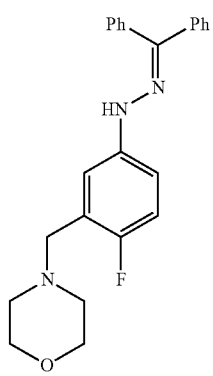

B-09b is prepared analogously to B-03b starting from B-09a (3.0 g, 10.9 mmol), benzophenone hydrazone (2.15 g, 10.9 mmol), sodium tert-butoxide (1.58 g, 16.4 mmol), (2-biphenyl)-di-tert-butylphosphine (135 mg, 0.438 mmol) and palladium(II)acetate (49 mg, 0.22 mmol). Yield: 2.40 g.

B-09 is prepared analogously to B-03 starting from B-09b (2.40 g, 6.16 mmol). Yield: 1.64 g.

B-10) [4-(1-Methyl-pyrrolidin-2-yl)-phenyl]-hydrazine hydrochloride

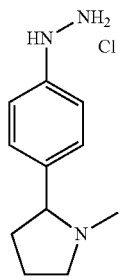

B-10a) 5-(4-Bromo-phenyl)-3,4-dihydro-2H-pyrrole

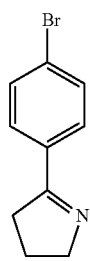

A mixture of 4'-bromo-4-chlorobutyrophenone (20.0 g, 76.5 mmol), sodium azide (7.46 g, 115 mmol) and sodium iodide (344 mg, 2.29 mmol) is stirred overnight at 55° C. The reaction mixture is poured on water and extracted with DCM. The organic phases are dried over MgSO$_4$ and concentrated in vacuo. The residue is dissolved in 150 mL cyclohexane, triphenylphosphine (20.1 g, 76.5 mmol) is added and the reaction mixture is stirred overnight at RT. The reaction mixture is filtered and the solids are washed with cold diethyl ether. The filtrate is concentrated in vacuo, water is added and the mixture is extracted with DCM. The combined organic phases are washed with water and brine, dried over MgSO$_4$ and concentrated in vacuo. The residue is treated with a mixture diethyl ether/cyclohexane (1/1, v/v), filtered and the filtrate is concentrated in vacuo. Yield: 15.6 g.

B-10b) 2-(4-Bromo-phenyl)-pyrrolidine

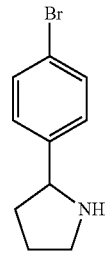

To a mixture of B-10a (5.50 g, 24.5 mmol) in 20% acetic acid in MeOH at 0° C. is added sodium boronhydride (1.93 g, 36.8 mmol). The reaction mixture is stirred at 0° C. for 1 h and then 4 h at RT. Then 20 mL 1M HCl is added and the reaction mixture is extracted with diethyl ether. The aqueous phase is basified with 10 M aqueous NaOH and extracted with DCM. The combined organic extracts are washed with brine, dried over MgSO$_4$ and concentrated in vacuo. Yield: 3.92 g.

B-10c) 2-(4-Bromo-phenyl)-1-methyl-pyrrolidine

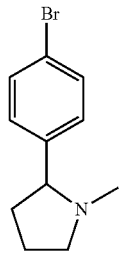

To a mixture of B-10b (2.5 g, 11.1 mmol) and potassium carbonate (3.06 g, 22.1 mmol) in ACN is added methyl iodide (0.76 mL, 12 mmol) at 0° C. The reaction mixture is stirred 0.5 h at RT and then filtered. The solids are washed with ACN and the filtrate is concentrated in vacuo. The residue is dissolved in ethyl acetate, washed with 0.01 M aqueous NaOH and brine, dried over MgSO$_4$ and concentrated in vacuo. The residue is purified by flash chromatography (silica gel, 0-10% MeOH in DCM containing 0.5% ammonia). Yield: 1.35 g.

B-10d) N-Benzhydrylidene-N'-[4-(1-methyl-pyrrolidin-2-yl)-phenyl]-hydrazine

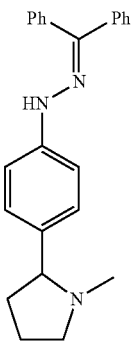

B-10d is prepared analogously to B-03b starting from B-10c (1.35 g, 5.62 mmol) benzophenone hydrazone (1.10 g, 5.62 g), sodium tert-butoxide (0.81 g, 8.4 mmol), (2-biphenyl)di-tert-butyl phosphine (84 mg, 0.28 mmol) and palladium(II) acetate (38 mg, 0.17 mmol). Yield: 1.20 g.

B-10 is prepared analogously to B-03 starting from B-10d (1.20 g, 3.38 mmol). Yield: 0.42 g.

B-11) (4-Hydrazino-phenyl)-methanol is commercially available

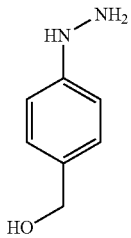

B-12) (3-Methanesulfonyl-phenyl)-hydrazine

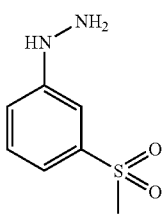

B-012 is prepared analogously to B-05 starting from 3-methylsulfonylaniline hydrochloride (2.50 g, 11.4 mmol), sodium nitrite (1.18 g, 17.1 mmol) and tin(II)chloride dihydrate (14.9 g, 66.0 mmol). The product is purified by precipitation from ethyl acetate with cyclohexane. Yield: 1.08 g.

B-13) N-(3-Chloro-4-hydrazino-phenyl)-N-methyl-acetamide

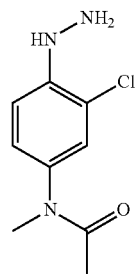

B-13a) N-(4-Bromo-3-chloro-phenyl)-N-methyl-acetamide

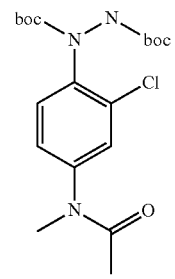

To a solution of 4-bromo-3-chloroacetanilide (10.0 g, 40.2 mmol) in 50 mL THF is added 60% sodium hydride in mineral oil (2.40 g, 60.0 mmol) and the reaction mixture is stirred for 1 h at RT. The reaction mixture is cooled to 0° C., methyliodide (2.49 mL, 40.0 mmol) is added. After 2 h additional methyl iodide (0.25 mL, 4.0 mmol) is added and the reaction mixture is stirred at RT for 10 min. The reaction mixture is quenched with saturated aqueous ammonium chloride, filtered and extracted with diethyl ether. The organic phases are washed with brine, dried over $Na_2SO_4$ and evaporated to dryness. Yield: 10.3 g.

B-13b) N-[4-(Acetyl-methyl-amino)-2-chloro-phenyl]-hydrazinedicarboxylic acid di-tert-butyl ester To lithium chloride (906 mg, 21.0 mmol) in 20 mL THF is added a 2 M solution of isopropylmagnesium chloride in diethyl ether (11.0 mL, 22.0 mmol) and the reaction mixture is stirred at RT for 0.5 h. The reaction mixture is cooled to −78° C. and a solution of B-13a (5.0 g, 19.0 mmol) in 10 mL THF is added. The reaction mixture is warmed to −15° C. and after 2 h di-tert-butylazodicarboxylate (4.39 g, 19.0 mmol) is added. After 20 min saturated aqueous ammonium chloride is added and the reaction mixture is extracted with diethyl ether. The organic phases are washed with water and brine, dried over $Na_2SO_4$ and concentrated in vacuo. The residue is purified by chromatography (silica gel, 50 to 70% ethyl acetate in cyclohexane). Yield: 3.91 g.

B-13b (1.96 g, 4.74 mmol) is dissolved in 20 mL DCM, cooled to 0° C. and 20 mL trifluoroacetic acid is added. The reaction mixture is warmed to RT and stirred for 2 h. The reaction mixture is concentrated in vacuo, neutralized with 5 M aqueous NaOH and extracted with DCM. The organic phases are washed with water and brine, dried over $Na_2SO_4$ and concentrated in vacuo. Yield: 960 mg.

B-14) (4-Hydrazino-phenyl)-ethanone O-methyl-oxime hydrochloride

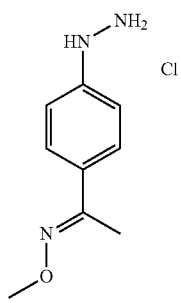

B-14a) N-(4-Acetyl-phenyl)-hydrazinedicarboxylic acid di-tert-butyl ester

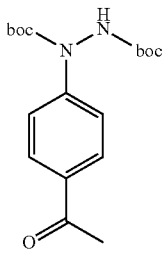

A mixture of 4-methoxycarbonylphenylboronic acid (2.0 g, 12.2 mmol), di-tert-butylazo-dicarboxylate (2.88 g, 12.5 mmol) and copper(II) acetate (220 mg, 1.21 mmol) in 35 mL MeOH is stirred for 4 h at 45° C. The reaction mixture is concentrated in vacuo, DCM is added and the mixture is washed with water. The organic phase is washed with brine, dried over $MgSO_4$ and concentrated in vacuo. The residue is triturated with hot n-hexane. Yield: 2.46 g.

B-14b) N-(4-{1-[(E)-Methoxyimino]-ethyl}-phenyl)-hydrazinedicarboxylic acid di-tert-butyl ester

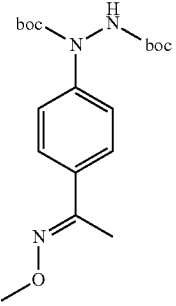

B-14a (2.10 g, 5.99 mmol) and O-methylhydroxylamine hydrochloride (500 mg, 5.99 mmol) are stirred in MeOH for 4 h. The reaction mixture is diluted with DCM and washed with water and brine. The water phases are neutralized with saturated aqueous sodium hydrogencarbonate and extracted with DCM. The combined organic phases are dried over $MgSO_4$ and concentrated in vacuo. Yield: 1.92 g.

B-14b (1.92 g, 5.09 mmol) is dissolved in 20 mL dioxane and 12.8 mL 4 M HCl in dioxane are added. The reaction mixture is stirred for 2 h at 50° C. and overnight at RT. The reaction mixture is filtered and the solids are dried in vacuo. Yield: 1.10 g.

B-15) 4-Hydrazino-benzaldehyde O-(2-methoxy-ethyl)-oxime hydrochloride

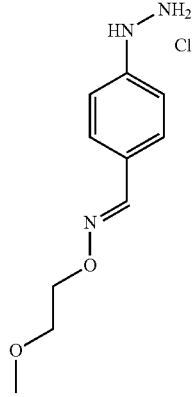

B-15a) 2-(2-Methoxy-ethoxy)-isoindole-1,3-dione

A mixture of N-hydroxyphthalimide (30.0 g, 184 mmol) and potassium carbonate (25.4 g, 138 mmol) in 300 mL NMP is heated to 50° C. Potassium iodide (0.15 g, 0.90 mmol) and 2-bromoethyl methyl ether (19.0 ml, 202 mmol) are added and the reaction mixture is stirred at 80° C. for 2 h. The reaction mixture is poured on 1 M aqueous HCl and extracted with ethyl acetate. The combined organic phases are dried over $MgSO_4$ and concentrated in vacuo. The residue is triturated with water and subsequently crystallized from EtOH. Yield: 17.1 g.

B-15b) O-(2-Methoxy-ethyl)-hydroxylamine hydrochloride

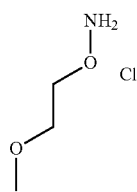

B-15a (17.1 g, 77.3 mmol) is dissolved in ethyl acetate, ethanolamine (5.13 mL, 85.0 mmol) is added and the reaction mixture is stirred for 2 h at 80° C. The reaction mixture is concentrated in vacuo, triturated with diethyl ether and filtered. To the filtrate 1 M HCl in diethyl ether (77.3 mL, 77.3 mmol) is added and the formed precipitate is filtered off and dried in vacuo. Yield: 4.76 g.

B-15c) N-(4-Formyl-phenyl)-hydrazinedicarboxylic acid di-tert-butyl ester

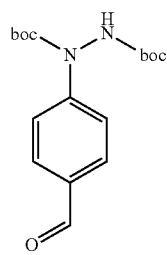

B-15c is prepared analogously to B-14a starting from 4-formylphenylboronic acid (3.52 g, 23.5 mmol), di-tert-butylazodicarboxylate (5.95 g, 25.8 mmol) and copper(II) acetate (230 mg, 1.27 mmol). The product is purified by flash chromatography (silica gel, 0-60% ethyl acetate in cyclohexane). Yield: 7.50 g.

B-15d) N-{4-[(2-Methoxy-ethoxyimino)-methyl]-phenyl}-hydrazinedicarboxylic acid di-tert-butyl ester

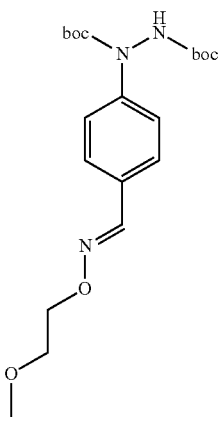

B-15d is prepared analogously to B-14b starting from B-15c (3.96 g, 11.8 mmol) and B-15b (1.50 g, 11.8 mmol). The product is purified by preparative RP-HPLC (5-98% ACN in water). Yield: 4.25 g.

B-15 is prepared analogously to B-14 starting from B-15d (4.25 g, 10.4 mmol) and 4 M HCl in dioxane (25.9 mL, 104 mmol). Yield: 2.90 g.

B-16) 4-Hydrazino-benzaldehyde O-(2-morpholin-4-yl-ethyl)-oxime hydrochloride

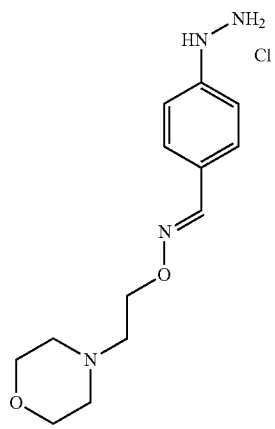

B-16a) 2-(2-Morpholin-4-yl-ethoxy)-isoindole-1,3-dione hydrochloride

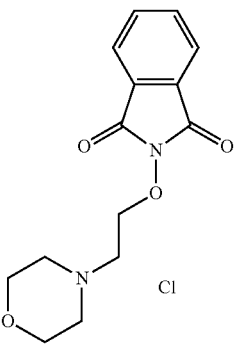

B-16a is prepared analogously to B-15a starting from N-hydroxyphthalimide (5.0 g, 30.7 mmol), potassium carbonate (4.24 g, 30.7 mmol) and N-(2-chloroethyl)morpholine hydrochloride (6.27 g, 33.7 mmol). The product is isolated as the hydrochloride. Yield: 4.22 g.

B-16b) O-(2-Morpholin-4-yl-ethyl)-hydroxylamine hydrochloride

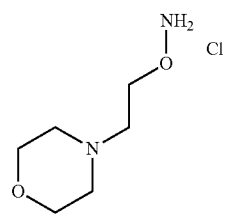

B-16b is prepared analogously to B-15b starting from B-16a (4.22 g, 15.3 mmol) and ethanolamine (1.01 mL, 16.8 mmol). Yield: 1.31 g.

B-16c) N-{4-[(2-Morpholin-4-yl-ethoxyimino)-methyl]-phenyl}-hydrazinedicarboxylic acid di-tert-butyl ester

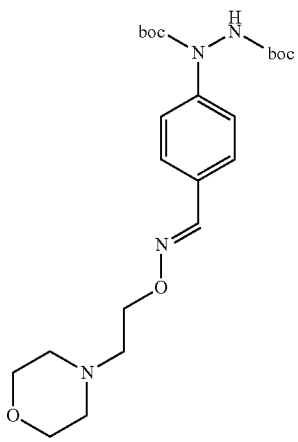

B-16c is prepared analogously to B-14a starting from B-16b (1.31 g, 7.17 mmol) and B-15c (2.41 g, 7.17 mmol). The product is purified by preparative RP-HPLC (5-98% ACN in water) Yield: 1.48 g.

B-16c is taken up in 5 mL dioxane and 8.0 mL of a 4 M solution of HCl in dioxane is added. The reaction mixture is stirred overnight at RT and then concentrated in vacuo. The residue is triturated in DCM. Yield: 0.52 g.

B-17) 2,6-Difluoro-4-hydrazino-benzaldehyde O-(2-methoxy-ethyl)-oxime hydrochloride

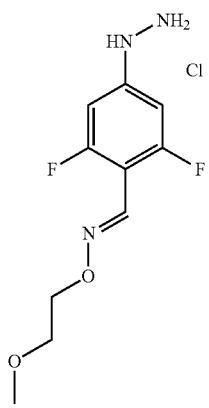

B-17a) N,N-(3,5-Difluoro-4-formyl-phenyl)-hydrazinedicarboxylic acid di-tert-butyl ester

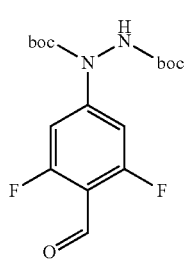

B-17a is prepared analogously to B-14a starting from 3,5-difluoro-4-formylboronic acid (5.0 g, 26.9 mmol), di-tert-butylazocarboxylate (6.81 g, 29.6 mmol) and copper(II) acetate (488 mg, 2.69 mmol). Yield: 9.93 g.

B-17b) N,N-{3,5-Difluoro-4-[(2-methoxy-ethoxyimino)-methyl]-phenyl}-hydrazine-dicarboxylic acid di-tert-butyl ester

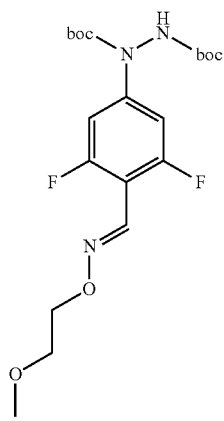

B-17b is prepared analogously to B-14b starting from B-17a (1.46 g, 3.92 mmol) and B-15b (500 mg, 3.92 mmol). The product is purified by preparative RP-HPLC (5-98% ACN in water). Yield: 700 mg.

B-17 is prepared analogously to B-14 starting from B-17b (700 mg, 1.57 mmol) and 4 M HCl in dioxane (3.93 mL, 15.7 mmol). Yield: 263 mg.

B-18) 2,3-Difluoro-4-hydrazino-benzaldehyde O-(2-methoxy-ethyl)-oxime hydrochloride

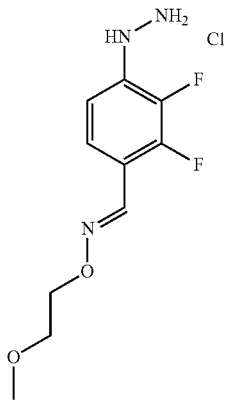

B-18a) N,N-(2,3-Difluoro-4-formyl-phenyl)-hydrazinedicarboxylic acid di-tert-butyl ester

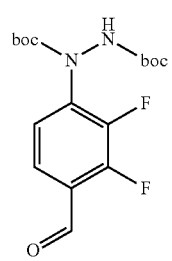

B-18a is prepared analogously to B-14a starting from 2,3-difluoro-4-formylboronic acid (5.0 g, 26.9 mmol), di-tert-butylazodicarboxylate (6.81 g, 29.6 mmol) and copper(II) acetate (488 mg, 2.69 mmol). Yield: 9.70 g.

B-18b) N,N-{2,3-Difluoro-4-[(2-methoxy-ethoxy-imino)-methyl]-phenyl}-hydrazine-dicarboxylic acid di-tert-butyl ester

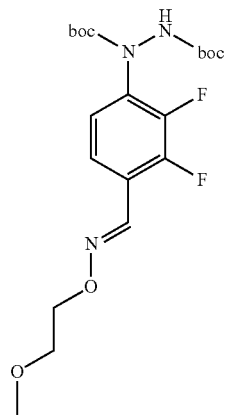

B-18b is prepared analogously to B-14b starting from B-18a (1.46 g, 3.92 mmol) and B-15b (500 mg, 3.92 mmol). The product is purified by preparative RP-HPLC (5-98% ACN in water). Yield: 840 mg.

B-18 is prepared analogously to B-14 starting from B-18b (840 mg, 1.89 mmol) and 4 M HCl in dioxane (4.72 ml, 18.9 mmol). Yield: 276 mg.

B-19) Cyclopropylmethyl-hydrazine hydrochloride

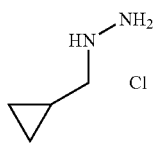

B-19a) N'-[1-Cyclopropyl-methylidene]-hydrazinecarboxylic acid tert-butyl ester

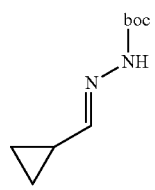

Cyclopropylcarboxaldehyde (4.07 mL, 14.3 mmol) is dissolved in 3 mL MeOH and tert-butylcarbazate (1.89 g, 14.3 mmol) is added. The reaction mixture is stirred overnight at RT and subsequently concentrated in vacuo. Yield: 2.57 g.

B-19b) N'-Cyclopropylmethyl-hydrazinecarboxylic acid tert-butyl ester

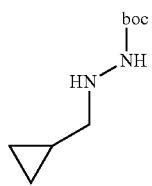

To a mixture of B-19a (2.57 g, 13.9 mmol) in 13 mL 50% aqueous acetic acid is added sodium cyanoborohydride (877 mg, 13.9 mmol) and the reaction mixture is stirred overnight RT. The reaction mixture is basified with 10 M aqueous NaOH and extracted with DCM. The combined organic extracts are washed with saturated aqueous sodium hydrogen carbonate, dried over MgSO$_4$ and concentrated in vacuo. Yield: 2.05 g. B-19b (2.05 g, 11.0 mmol) is dissolved in 3 mL dioxane and 4 M HCl in dioxane (13.8 mL, 55.0 mmol) is added. The reaction mixture is stirred at RT and then concentrated in vacuo. Yield: 1.30 g.

B-20 (1-Ethyl-propyl)-hydrazine hydrochloride

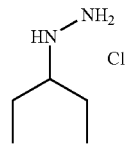

B-20a)
N'-(1-Ethyl-propylidene)-hydrazinecarboxylic acid tert-butyl ester

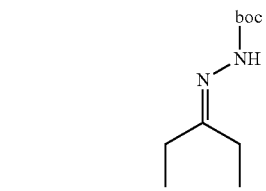

B-20a is prepared analogously to B-19a starting from 3-pentanone (1.23 mL, 11.6 mmol) and tert-butylcarbazate (1.53 g, 11.6 mmol). Yield: 2.26 g.

B-20b) N'-(1-Ethyl-propyl)-hydrazinecarboxylic acid tert-butyl ester

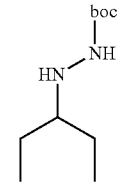

B-20b was prepared analogously to B-19b starting from B-20a (2.26 g, 11.3 mmol) and sodium cyanoborohydride (709 mg, 11.3 mmol). Yield: 1.68 g.

B-20 is prepared analogously to B-19 starting from B-20b (1.68 g, 8.31 mmol) and 4 M hydrochloric acid in dioxane (10.4 ml, 41.5 mmol). Yield: 1.20 g.

B-21) Isobutyl-hydrazine hydrochloride

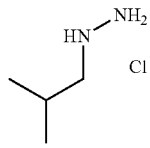

B-21a) N'-[2-Methyl-propylidene]-hydrazinecarboxylic acid tert-butyl ester

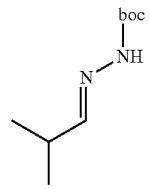

B-21a is prepared analogously to B-19a starting from isobutyraldehyde (1.26 mL, 13.9 mmol) and tert-butylcarbazate (1.83 g, 13.9 mmol). Yield: 2.56 g.

B-21b) N'-Isobutyl-hydrazinecarboxylic acid tert-butyl ester

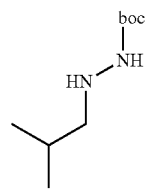

B-21b is prepared analogously to B-19b starting from B-21a (2.56 g, 13.7 mmol) and sodium cyanoborohydride (864 mg, 13.7 mmol). Yield: 1.97 g.

B-21 is prepared analogously to B-19 starting from B-21b (1.97 g, 10.5 mmol) and 4 M HCl in dioxane (13.1 mL, 52.3 mmol). Yield: 1.30 g.

B-22) (Tetrahydro-pyran-4-yl)-hydrazine

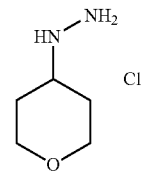

B-22a) N'-(Tetrahydro-pyran-4-ylidene)-hydrazinecarboxylic acid tert-butyl ester

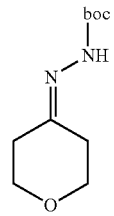

B-22a was prepared analogously to B-19a starting from tetrahydro-4H-pyran-4-one (923 μL, 9.99 mmol) and tert-butylcarbazate (1.32 g, 9.99 mmol). Yield: 2.15 g.

B-22b) N'-(Tetrahydro-pyran-4-yl)-hydrazinecarboxylic acid tert-butyl ester

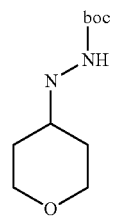

B-22b is prepared analogously to B-19b starting from B-22a (2.15 g, 10.0 mmol) and sodium cyanoborohydride (631 mg, 10.0 mmol). Yield: 1.57 g.

B-22 is prepared analogously to B-19 starting from B-22b (1.57 g, 7.26 mmol) and 4 M HCl in dioxane (9.07 ml, 36.3 mmol). Yield: 1.10 g.

B-23) (2-Methyl-allyl)-hydrazine hydrochloride

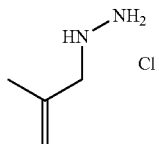

B-23a) N'-[2-Methyl-prop-2-en-(E)-ylidene]-hydrazinecarboxylic acid tert-butyl ester

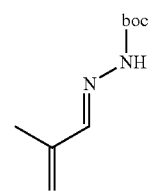

B-23a is prepared analogously to B-19a starting from methacroleine (1.18 ml, 14.3 mmol) and tert-butylcarbazate (1.89 g, 14.3 mmol). Yield: 2.61 g.

B-23b) N'-(2-Methyl-allyl)-hydrazinecarboxylic acid tert-butyl ester

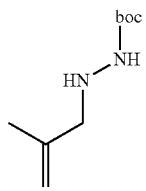

B-23b is prepared analogously to B-19b starting from B-23a (2.61 g, 14.2 mmol) and sodium cyanoborohydride (890 mg, 14.2 mmol). Yield: 1.88 g.

B-23 is prepared analogously to B-19 starting from B-23b (1.88 g, 10.1 mmol) and 4 M HCl in dioxane (12.6 mL, 50.5 mmol). Yield: 1.14 g.

B-24) (2-Methoxy-ethyl)-hydrazine hydrochloride

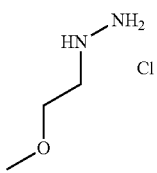

B-24a) N'-Isopropylidene-hydrazinecarboxylic acid tert-butyl ester

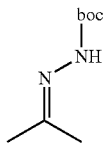

To a solution of tert-butylcarbazate (50.0 g, 378 mmol) in 40 mL acetone is added 10 g $MgSO_4$ and 5 mL acetic acid and the reaction mixture is stirred at reflux temperature for 1 h. The reaction mixture is filtered and concentrated in vacuo. The residue is crystallized from diethyl ether/cyclohexane. Yield: 49.4 g.

B-24b) N'-Isopropylidene-N-(2-methoxy-ethyl)-hydrazinecarboxylic acid tert-butyl ester

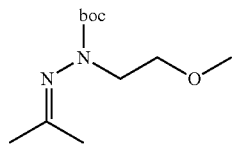

B-24a (5.0 g, 29.0 mmol) is dissolved in 70 mL toluene and potassium hydroxide (2.12 g, 37.7 mmol) and tetrabutylammonium hydrogensulfate (986 mg, 2.90 mmol) are added. The reaction mixture is heated to 50° C. and 2-bromoethyl methyl ether (3.23 mL, 34.8 mmol) is added. Next the reaction mixture is heated to 80° C. and stirred for 2 h. The reaction mixture is washed with water, the organic phase is dried on $MgSO_4$ and concentrated in vacuo. Yield: 4.35 g.

To a solution of B-24b (4.25 g, 18.9 mmol) in 80 mL THF is added 2 M aqueous HCl (18.9 mL, 37.8 mmol) and the reaction mixture is stirred at reflux temperature for 3 h. The reaction mixture is concentrated in vacuo and co-evaporated several times with toluene. Yield: 2.93 g.

B-25) Prop-2-ynyl-hydrazine hydrochloride

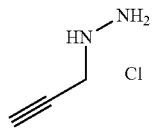

B-25a) N'-Isopropylidene-N-prop-2-ynyl-hydrazinecarboxylic acid tert-butyl ester hydrochloride

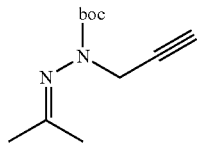

B-25a is prepared analogously to B-24b starting from B-24a (2.34 g, 13.6 mmol), potassium hydroxide (991 mg, 17.7 mmol), tetrabutylammonium hydrogensulfate (461 mg, 1.36 mmol) and propargyl chloride (70% in toluene, 1.8 mL, 16.3 mmol). Yield: 1.99 g.

B-25 is prepared analogously to B-24 starting from B-25a (1.99 g, 9.64 mmol) and 2 M aqueous HCl (9.46 mL, 18.9 mmol). Yield: 1.03 g.

B-26) Piperidin-4-yl-hydrazine is commercially available

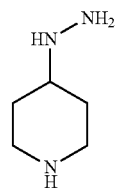

B-27) [1-(2-Methoxy-ethyl)-piperidin-4-yl]-hydrazine hydrochloride

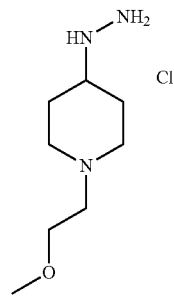

B-27a) N'-Piperidin-4-ylidene-hydrazinecarboxylic acid tert-butyl ester hydrochloride

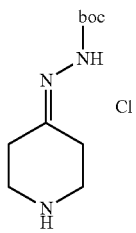

A mixture of 4-piperidone hydrochloride monohydrate (31.2 g, 203 mmol) and tert-butylcarbazate (26.8 g, 203 mmol) in 100 mL MeOH is stirred over weekend at RT and then concentrated in vacuo. The residue is crystallized from ethyl acetate. Yield: 47.5 g.

B-27b) N'-Piperidin-4-yl-hydrazinecarboxylic acid tert-butyl ester

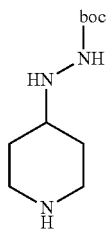

B-27a (40.2 g, 161 mmol) is dissolved in 50% aqueous acetic acid (240 mL) and sodium cyanoborohydride (12.1 g, 193 mmol) is added under cooling with an ice bath and the reaction mixture is stirred for 1 h. The reaction mixture is basified and extracted with DCM. The organic phases are washed with saturated aqueous sodium hydrogencarbonate, dried over sodium sulfate and concentrated in vacuo. Yield: 21.1 g.

B-27c) N'-[1-(2-Methoxy-ethyl)-piperidin-4-yl]-hydrazinecarboxylic acid tert-butyl ester

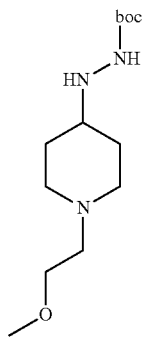

To a mixture of B-27b (2.50 g, 11.6 mmol), potassium carbonate (2.76 g, 20.0 mmol) and potassium iodide (50 mg, 0.30 mmol) in 25 mL DMF is added 2-bromoethyl methyl ether (1.23 mL, 12.8 mmol) and the reaction mixture is stirred overnight at RT. The reaction mixture is poured on water and extracted with ethyl acetate. The combined organic extracts are washed with water and brine, dried over MgSO$_4$ and concentrated in vacuo.
Yield: 2.65 g.

B-27c is taken up in dioxane, treated with 4 M hydrochloric acid in dioxane (10.0 mL, 40.0 mmol) and stirred overnight at RT. The formed precipitate is filtered off and dried in vacuo. Yield: 1.2 g.

B-28) (1-Prop-2-ynyl-piperidin-4-yl)-hydrazine hydrochloride

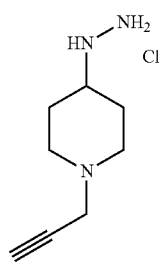

B-28a) N'-(1-Prop-2-ynyl-piperidin-4-yl)-hydrazinecarboxylic acid tert-butyl ester

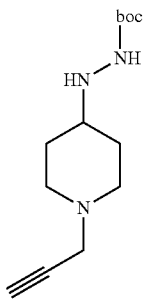

B-28a is prepared analogously to B-27c starting from B-27b (10.0 g, 46.4 mmol), potassium carbonate (4.0 g, 29.0 mmol) and propargyl bromide (80% in toluene, 5.26 mL, 48.8 mmol). Yield: 12.4 g.

B-28 is prepared analogously to B27 starting from B-28a (12.4 g, approximately 46.4 mmol) and 4 M hydrochloric acid in dioxane (61.3 ml, 245 mmol). Yield: 9.30 g.

B-29) (1-Cyclopropyl-piperidin-4-yl)-hydrazine hydrochloride

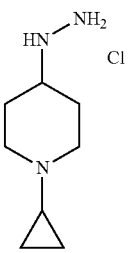

B-29a) N'-(1-Cyclopropyl-piperidin-4-ylidene)-hydrazinecarboxylic acid tert-butyl ester

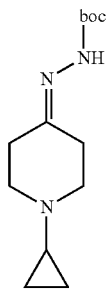

A mixture of 1-cyclopropyl-4-piperidon (10.0 g. 71.8 mmol) and tert-butylcarbazate (9.50 g, 71.8 mmol) in 25 mL THF is stirred for 3 h at RT and then concentrated in vacuo. Yield: 19.2 g.

B-29b) N'-(1-Cyclopropyl-piperidin-4-yl)-hydrazinecarboxylic acid tert-butyl ester

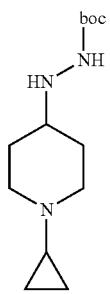

B-29b is prepared analogously to B-27b starting from B-29a (18.0 g, 71.1 mmol) and sodium cyanoborohydride (4.47 g, 71.1 mmol). Yield: 17.2 g.

Under cooling with an ice bath acetyl chloride (14.3 mL, 201 mmol) is added to 40 mL EtOH. Then B-29b (17.2 g, 67.3 mmol) is added and the reaction mixture is stirred for 1 h at RT. The reaction mixture is filtered and the solids are dried in vacuo at 40° C. Yield: 12.3 g.

B-30) (1-Methyl-piperidin-4-yl)-hydrazine is commercially available

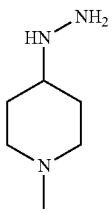

B-31) 4-Hydrazino-benzaldehyde O-methyl-oxime hydrochloride

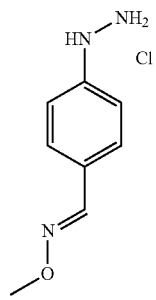

A mixture of B-15c (7.50 g, 22.3 mmol) and methoxyamine hydrochloride (1.95 g, 23.4 mmol) in 50 mL MeOH is stirred under reflux at 75° C. for 2 h. Then 1 mL of concentrated hydrochloric acid is added and the reaction mixture is stirred for another h at 75° C. and then concentrated in vacuo. The residue is dried in vacuo at 40° C. overnight and then triturated with DCM. Yield: 3.2 g.

B-32 [1-(3-Fluoro-4-hydrazino-phenyl)-cyclopropyl]-dimethyl-amine hydrochloric acid

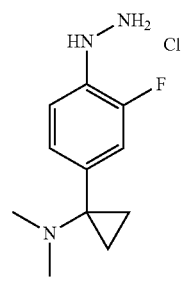

B-32a) [1-(4-Bromo-3-fluoro-phenyl)-cyclopropyl]-carbamic acid tert-butyl ester

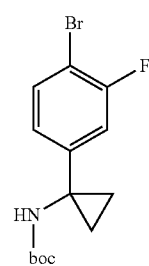

A mixture of 1-(4-bromo-3-fluorophenyl)cyclopropanecarboxylic acid (7.4 g, 28.6 mmol, prepared from 1-bromo-4-bromomethyl-2-fluorobenzene according to Peretto et al. J Med. Chem. 2005, 48, 5705-20), DIPEA (6.36 mL, 37.1 mmol), tert-butanol (67.0 mL, 714 mmol), diphenylphosphorylazide (7.37 mL, 34.3 mmol) and molsieve (4 Å) in 100 mL toluene is stirred under reflux overnight. The reaction mixture is filtered and concentrated in vacuo. The residue is taken up B-32b) [1-(4-Bromo-3-fluoro-phenyl)-cyclopropyl]-methyl-carbamic acid tert-butyl ester

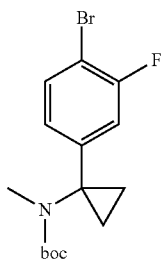

To a solution of B-32a (9.37 g, 28.4 mmol) in 120 mL DMF is added sodium hydride (60% in mineral oil, 1.7 g, 42.6 mmol) and the reaction mixture is stirred at RT for 0.5 h. The reaction mixture is warmed to 40° C. and methyl iodide (3.89 mL, 62.4 mmol) is added. After 1 h the reaction mixture is poured on ice water and extracted with ethyl acetate. The combined organic phases are washed with water and brine, dried over MgSO₄ and concentrated in vacuo. Yield: 8.54 g.

B-32c) [1-(4-Bromo-3-fluoro-phenyl)-cyclopropyl]-methyl-amine hydrochloride

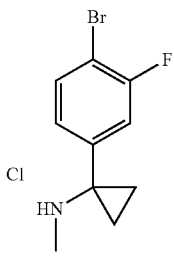

A mixture of B-32b (8.54 g, 24.8 mmol) in 4 M hydrochloric acid in dioxane (31.0 mL, 124 mmol) is stirred for 1 h at RT and then concentrated in vacuo. Yield: 7.28 g.

B-32d) [1-(4-Bromo-3-fluoro-phenyl)-cyclopropyl]-dimethyl-amine

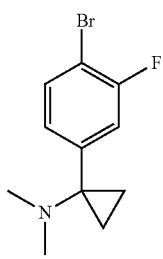

A mixture of B-32c (7.28 g, 25.9 mmol) and formaldehyde (30% in water, 3.90 mL, 38.9 mmol) in 150 mL 1,2-dichloroethane is stirred vigorously for 0.5 h at RT. Acetic acid (2.23 mL, 38.9 mmol) and sodium triacetoxyborohydride (8.25 g, 38.9 mmol) are added under cooling with ice water and the reaction mixture is stirred for 2 h at RT. Saturated aqueous sodium hydrogencarbonate is added and the reaction mixture is extracted with DCM. The combined organic phases are dried over MgSO₄ and concentrated in vacuo. Yield: 7.07 g.

B-32e) {1-[4-(N'-Benzhydrylidene-hydrazino)-3-fluoro-phenyl]-cyclopropyl}-dimethyl-amine

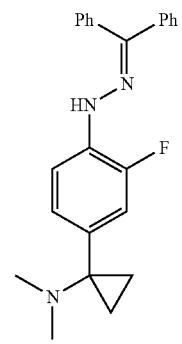

A mixture of B-32d (7.07 g, approximately 25.9 mmol), benzophenone hydrazone (5.38 g, 27.4 mmol), sodium tert-butoxide (3.95 g, 41.1 mmol) and (2-biphenyl)-di-tert-butylphosphine (422 mg, 1.37 mmol) in 200 mL dioxane is degassed and put under an argon atmosphere. Palladium(II) acetate (122 mg, 548 µmol) is added and the reaction mixture is stirred for 2 h at 80° C. The reaction mixture is filtered and concentrated in vacuo. The residue purified by flash chromatography (silica gel, 1-5% MeOH in DCM). Yield: 4.84 g.

B-32e (4.8 g, 12.9 mmol) is dissolved in 10 mL n-propanol and 10 mL concentrated HCl is added. The reaction mixture is stirred for 1 h at 100° C. and then concentrated in vacuo. The residue is taken up in fresh n-propanol, concentrated in vacuo again, triturated with DCM and dried in vacuo at 40° C. Yield: 1.93 g.

B-33) 4-Hydrazino-3-methoxy-benzoic acid methyl ester is prepared according to WO2007113245

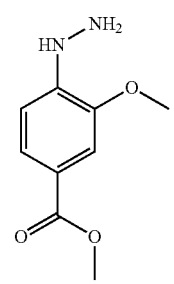

B-34) 3-Ethoxy-4-hydrazino-benzoic acid methyl ester

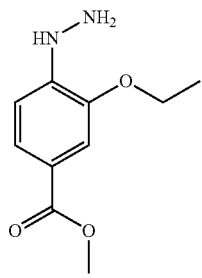

B-34a) 3-Ethoxy-4-nitro-benzoic acid methyl ester

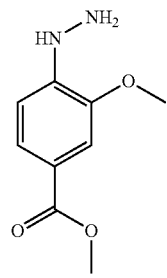

A mixture of methyl 3-hydroxyl-4-nitrobenzoate (25.1 g, 125 mmol) and bromoethane (20 mL, 263 mmol) in 200 mL ACN is cooled to 15° C. Potassium carbonate (54.4 g, 390 mmol) is added and the reaction mixture is stirred overnight at 60° C. Additional bromoethane (10 mL, 131 mmol) is added and the reaction mixture is stirred overnight at 95° C. The reaction mixture is filtered and the filtrate is concentrated in vacuo. The residue is triturated with ACN and dried in vacuo. Yield: 26.5 g.

B-34b) 4-Amino-3-ethoxy-benzoic acid methyl ester

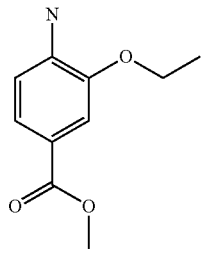

A mixture of B-34a (26.5 g, 118 mmol) and Raney nickel (1.5 g, 5.43 mmol) in 150 mL THF is stirred for 5 d at RT under an atmosphere of 10 bar dihydrogen. The reaction mixture is filtered and the filtrate is concentrated in vacuo. The residue is lyophilized from dioxane. Yield: 21.7 g.

B-34 is prepared analogously to B-05 starting from B-34b (21.5 g, 108 mmol), sodium nitrite (7.75 g, 110 mmol) and tin(II) chloride dihydrate (104 g, 453 mmol). The product is lyophilized from dioxane. Yield: 19.3 g.

B-35) 3-Hydrazino-N,N-dimethyl-benzenesulfonamide hydrochloride

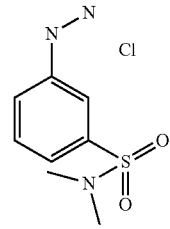

B-35a) N-(3-Dimethylsulfamoyl-phenyl)-hydrazinedicarboxylic acid di-tert-butyl ester

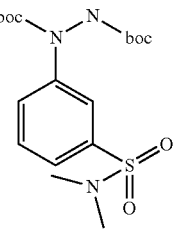

B-35a is prepared analogously to B-14a starting from 3-(N,N-dimethylsulphonamido)-benzeneboronic acid (1.0 g, 4.37 mmol), di-tert-butylazodicarboxylate (1.11 g, 4.83 mmol) and copper(II) acetate (79 mg, 0.44 mmol). The product is purified by preparative RP-HPLC (5-98% ACN in water). Yield: 1.15 g.

B-35 is prepared analogously to B-14 starting from B-35a (1.15 g, 2.77 mmol) and 4 M HCl in dioxane (6.92 ml, 27.8 mmol). Yield: 527 mg.

B-36) (3-Trifluoromethoxy-phenyl)-hydrazine hydrochloride

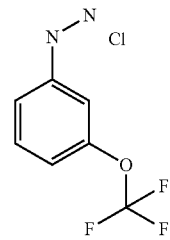

B-36a) N-(3-Trifluoromethoxy-phenyl)-hydrazinedicarboxylic acid di-tert-butyl ester

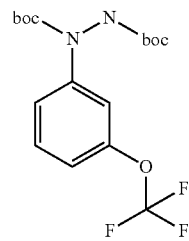

B-36a is prepared analogously to B-14a starting from 3-(trifluoromethoxy)benzeneboronic acid (1.0 g, 4.86 mmol), di-tert-butylazodicarboxylate (1.23 g, 5.34 mmol) and copper(II) acetate (88 mg, 0.49 mmol). The product is purified by preparative RP-HPLC (5-98% ACN in water). Yield: 1.26 g.

B-36 is prepared analogously to B-14 starting from B-36a (1.26 g, 3.21 mmol) and 4 M HCl in dioxane (8.03 ml, 32.1 mmol). Yield: 557 mg.

B-37) (3-Pyrazol-1-yl-phenyl)-hydrazine hydrochloride

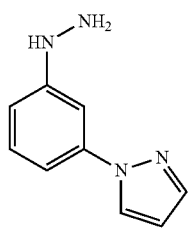

B-37a) N-(3-Pyrazol-1-yl-phenyl)-hydrazinedicarboxylic acid di-tert-butyl ester

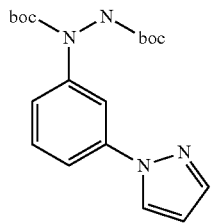

B-37a is prepared analogously to B-14a starting from 3-(1H-pyrazol-1-yl)phenylboronic acid (800 mg, 4.26 mmol), di-tert-butylazodicarboxylate (1.08 g, 4.68 mmol) and copper(II) acetate (77 mg, 0.43 mmol). Yield: 1.17 g.

B-37 is prepared analogously to B-14 starting from B-37a (1.17 g, 3.13 mmol) and 4 M HCl in dioxane (7.81 mL, 31.3 mmol). Yield: 518 mg.

Examples C

Examples C-01 to C-118 can be synthesized according to one of the following general procedures. The appropriate hydrazine and diketone required for synthesis can be deduced from the table of examples.

General Procedure C1:

The appropriate diketone (1 eq.) and the appropriate hydrazine or hydrazine hydrochloride (1 eq.) are added to acetic acid and allowed to stir at RT for 24 h. The acetic acid is removed under reduced pressure, the resulting crude material is dissolved in NMP and purified using RP-LC/MS (ACN:$H_2O$-ammonium hydrogen carbonate pH 9.3). The resulting product fractions are collected and the solvent removed via freeze-drying to yield the desired product.

General Procedure C2:

The appropriate diketone (1 eq.) and the appropriate hydrazine or hydrazine hydrochloride (5-10 eq.) are added to acetic acid and heated to 85° C.-160° C. for 1-6 h in the microwave. The acetic acid is removed under reduced pressure, the resulting crude material dissolved in NMP and purified using RP-LC/MS (ACN:$H_2O$-TFA pH 1). The resulting product fractions recollected and the solvent removed via freeze-drying to yield the desired product.

General Procedure C3

The appropriate diketone (1 eq.) and the appropriate hydrazine hydrochloride (1 eq.) are added to EtOH and heated to 100° C.-140° C. for 15-60 min in the microwave. The EtOH is removed under reduced pressure, the resulting crude material dissolved in NMP and purified using RP-LC/MS (ACN:$H_2O$-TFA pH 1). The resulting product fractions are collected and the solvent removed via freeze-drying to yield the desired product.

General procedure C4:

The appropriate diketone (1 eq.) and the appropriate hydrazine or hydrazine hydrochloride (1.3 eq.) are added to acetic acid and allowed to stir at 70° C. for 2 d. The acetic acid is removed under reduced pressure, the resulting crude material is dissolved in DMSO/TFA and purified using RP-LC/MS. The resulting product fractions are collected and the solvent is removed via freeze-drying to yield the desired product.

TABLE 1

Examples C-01-C-117

| No. | MOLSTRUCTURE | Diketone | Hydrazine | [M + H]$^+$ | rt |
|---|---|---|---|---|---|
| C-01 | | A-01 | B-03 | 553 | 1.51 |

TABLE 1-continued

Examples C-01-C-117

| No. | MOLSTRUCTURE | Diketone | Hydrazine | [M + H]⁺ | rt |
|---|---|---|---|---|---|
| C-02 | | A-02 | B-01 | 536 | 1.09 |
| C-03 | | A-02 | B-31 | 488 | 1.25 |
| C-04 | | A-03 | B-01 | 564 | 1.18 |
| C-05 | | A-04 | B-01 | 548 | 1.06 |

TABLE 1-continued

Examples C-01-C-117

| No. | MOLSTRUCTURE | Diketone | Hydrazine | [M + H]+ | rt |
|---|---|---|---|---|---|
| C-06 | | A-04 | B-31 | 500 | 1.19 |
| C-07 | | A-05 | B-01 | 548 | 1.06 |
| C-08 | | A-05 | B-31 | 500 | 1.19 |
| C-09 | | A-06 | B-01 | 550 | 1.1 |

TABLE 1-continued
Examples C-01-C-117
| No. | MOLSTRUCTURE | Diketone | Hydrazine | [M + H]+ | rt |
|---|---|---|---|---|---|
| C-10 | 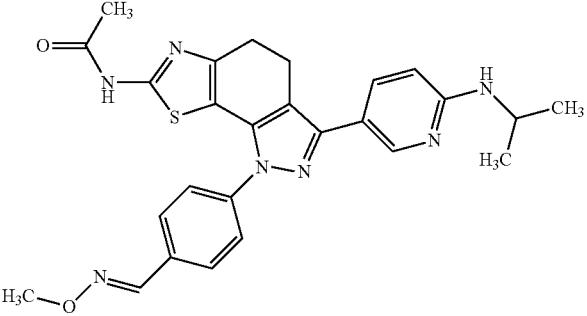 | A-06 | B-31 | 502 | 1.24 |
| C-11 | 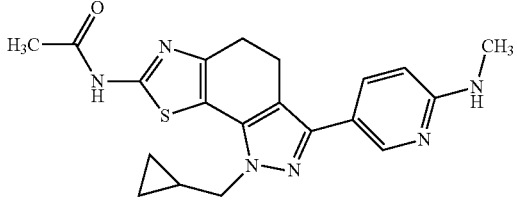 | A-07 | B-19 | 395 | 1.01 |
| C-12 | 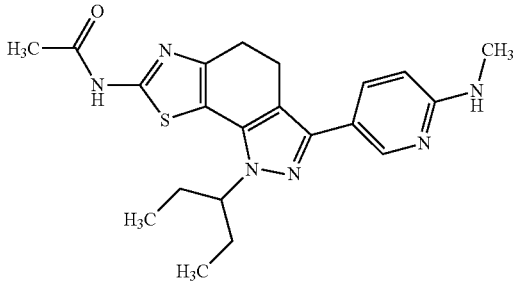 | A-07 | B-20 | 411 | 1.13 |
| C-13 | 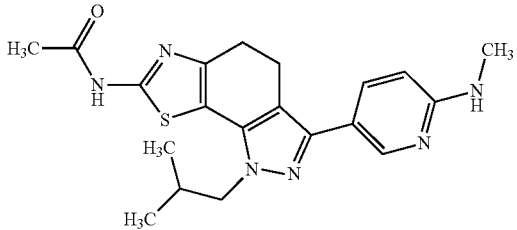 | A-07 | B-21 | 397 | 1.05 |
| C-14 | 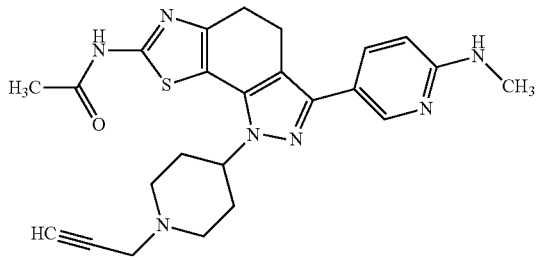 | A-07 | B-28 | 462 | 1.02 |

TABLE 1-continued

Examples C-01-C-117

| No. | MOLSTRUCTURE | Diketone | Hydrazine | [M + H]+ | rt |
|---|---|---|---|---|---|
| C-15 | | A-07 | B-29 | 464 | 1.12 |
| C-16 | | A-07 | cyclopentylhydrazine | 409 | 1.18 |
| C-17 | | A-07 | ethylhydrazine | 369 | 0.99 |
| C-18 | | A-07 | hydrazine | 341 | 0.95 |
| C-19 | | A-07 | isopropylhydrazine | 383 | 1.03 |
| C-20 | | A-07 | o,o-dimethyl-phenylhydrazine | 445 | 1.09 |

TABLE 1-continued

Examples C-01-C-117

| No. | MOLSTRUCTURE | Diketone | Hydrazine | [M + H]+ | rt |
|---|---|---|---|---|---|
| C-21 | | A-07 | o-methylphenyl-hydrazine | 431 | 1.11 |
| C-22 | | A-07 | t-butylhydrazine | 397 | 1.14 |
| C-23 | | A-08 | o-chlorophenyl hydrazine | 508 | 1.15 |
| C-24 | | A-09 | cyclohexylhydrazine | 467 | 1.22 |
| C-25 | | A-10 | B-22 | 439 | 1.04 |

TABLE 1-continued

Examples C-01-C-117

| No. | MOLSTRUCTURE | Diketone | Hydrazine | [M + H]+ | rt |
|-----|---|---|---|---|---|
| C-26 | | A-10 | B-23 | 409 | 1.06 |
| C-27 | | A-10 | B-24 | 413 | 1.01 |
| C-28 | | A-10 | B-25 | 393 | 1.02 |
| C-29 | | A-10 | B-28 | 476 | 1.09 |
| C-30 | | A-10 | B-30 | 452 | 1.06 |
| C-31 | | A-10 | ethylhydrazine | 383 | 1.03 |

TABLE 1-continued

Examples C-01-C-117

| No. | MOLSTRUCTURE | Diketone | Hydrazine | [M + H]+ | rt |
|---|---|---|---|---|---|
| C-32 | | A-10 | isopropylhydrazine | 397 | 1.1 |
| C-33 | | A-10 | methylhydrazine | 369 | 1.01 |
| C-34 | | A-10 | o-methylphenyl-hydrazine | 445 | 1.95 |
| C-35 | | A-10 | t-butylhydrazine | 411 | 1.21 |
| C-36 | | A-11 | B-27 | 510 | 1.09 |

TABLE 1-continued

Examples C-01-C-117

| No. | MOLSTRUCTURE | Diketone | Hydrazine | [M + H]+ | rt |
|---|---|---|---|---|---|
| C-37 | | A-11 | isopropylhydrazine | 411 | 1.14 |
| C-38 | | analogous to A-11 | isopropylhydrazine | 397 | 1.06 |
| C-39 | | A-12 | B-04 | 505 | 1.6 |
| C-40 | | A-13 | phenylhydrazine | 406 | 1.97 |
| C-41 | | A-14 | B-02 | 473 | 1.48 |

TABLE 1-continued

Examples C-01-C-117

| No. | MOLSTRUCTURE | Diketone | Hydrazine | [M + H]+ | rt |
|---|---|---|---|---|---|
| C-42 | | A-15 | isopropylhydrazine | 382 | 1.12 |
| C-43 | | A-16 | B-01 | 535 | 1.16 |
| C-44 | | A-17 | B-05 | 507 | 1.04 |
| C-45 | | A-17 | B-06 | 473 | 1.13 |

TABLE 1-continued

Examples C-01-C-117

| No. | MOLSTRUCTURE | Diketone | Hydrazine | [M + H]+ | rt |
|---|---|---|---|---|---|
| C-46 | | A-17 | ethylhydrazine | 370 | 1.04 |
| C-47 | | A-18 | isopropylhydrazine | 382 | 1.1 |
| C-48 | | A-19 | B-28 | 483 | 1.19 |
| C-49 | | A-20 | B-07 | 470 | 1.47 |
| C-52 | | A-23 | (2,2,2-trifluoro-ethyl)-hydrazine | 408 | 1.1 |

TABLE 1-continued

Examples C-01-C-117

| No. | MOLSTRUCTURE | Diketone | Hydrazine | [M + H]+ | rt |
|---|---|---|---|---|---|
| C-53 | | A-23 | (2-bromo-phenyl)-hydrazine | 480 | 1.15 |
| C-54 | | A-23 | (2-fluoro-phenyl)-hydrazine | 420 | 1.12 |
| C-55 | | A-23 | B-37 | 468 | 1.16 |
| C-56 | | A-23 | B-36 | 486 | 1.26 |

TABLE 1-continued

Examples C-01-C-117

| No. | MOLSTRUCTURE | Diketone | Hydrazine | [M + H]+ | rt |
|---|---|---|---|---|---|
| C-57 | | A-23 | (6-chloro-pyridin-3-yl)-hydrazine | 437 | 1.14 |
| C-58 | | A-23 | 2-hydrazino-benzonitrile | 427 | 1.16 |
| C-59 | | A-23 | 2-hydrazino-ethanol | 370 | 0.95 |
| C-60 | | A-23 | B-35 | 509 | 1.15 |
| C-61 | | A-23 | 3-hydrazino-propionitrile | 379 | 1.01 |

TABLE 1-continued

Examples C-01-C-117

| No. | MOLSTRUCTURE | Diketone | Hydrazine | [M + H]+ | rt |
|---|---|---|---|---|---|
| C-62 | | A-23 | B-08 | 446 | 1.45 |
| C-63 | | A-23 | B-12 | 480 | 1.01 |
| C-64 | | A-23 | B-13 | 507 | 1.78 |
| C-65 | | A-23 | B-14 | 473 | 1.18 |

/ # TABLE 1-continued
Examples C-01-C-117
| No. | MOLSTRUCTURE | Diketone | Hydrazine | [M + H]+ | rt |
|---|---|---|---|---|---|
| C-66 | 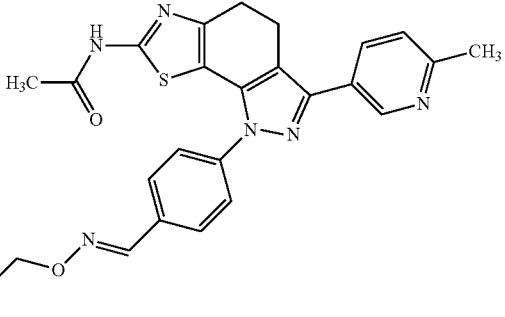 | A-23 | B-15 | 503 | 1.2 |
| C-67 | 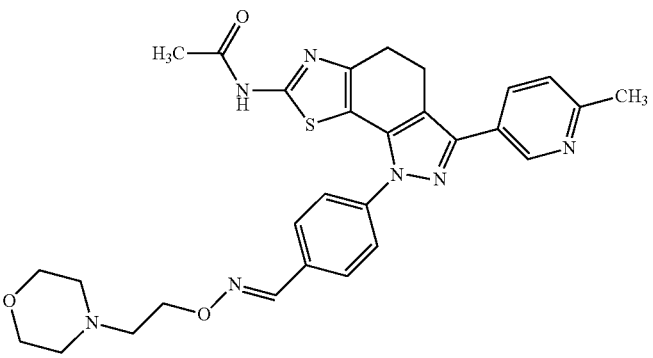 | A-23 | B-16 | 558 | 1.15 |
| C-68 | 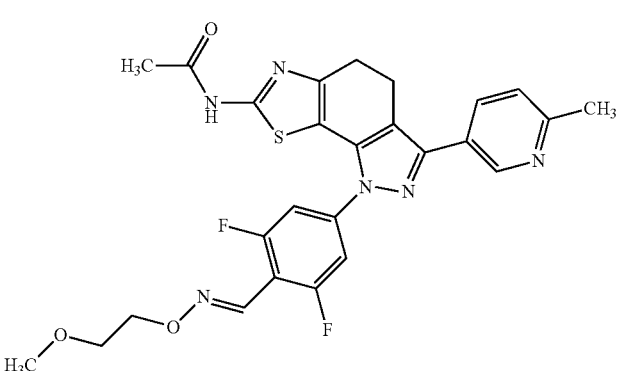 | A-23 | B-17 | 539 | 1.21 |
| C-69 | 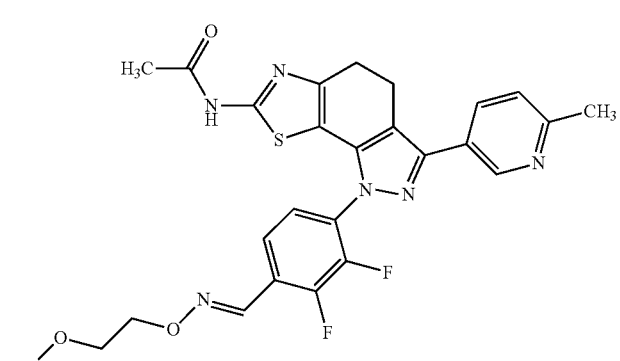 | A-23 | B-18 | 539 | 1.2 |

TABLE 1-continued

Examples C-01-C-117

| No. | MOLSTRUCTURE | Diketone | Hydrazine | [M + H]+ | rt |
|---|---|---|---|---|---|
| C-70 | | A-23 | B-26 | 409 | 1.01 |
| C-71 | | A-23 | B-31 | 459 | 2.01 |
| C-72 | | A-23 | benzylhydrazine | 416 | 1.14 |
| C-73 | | A-23 | isopropylhydrazine | 368 | 1.13 |
| C-74 | | A-23 | N-(3-hydrazino-phenyl)-acetamide HCl | 459 | 1.02 |

TABLE 1-continued

Examples C-01-C-117

| No. | MOLSTRUCTURE | Diketone | Hydrazine | [M + H]+ | rt |
|---|---|---|---|---|---|
| C-75 | | A-23 | pyridin-2-yl-hydrazine | 403 | 1.15 |
| C-76 | | A-24 | B-09 | 535 | |
| C-77 | | A-24 | B-10 | 501 | |
| C-78 | | A-24 | B-11 | 448 | 0.93 |
| C-79 | | A-24 | cyclobutyl-hydrazine | 396 | 1.01 |

TABLE 1-continued

Examples C-01-C-117

| No. | MOLSTRUCTURE | Diketone | Hydrazine | [M + H]⁺ | rt |
|---|---|---|---|---|---|
| C-80 | | A-24 | isopropylhydrazine | 384 | 0.99 |
| C-81 | | A-27 | isopropylhydrazine | 326 | 1.09 |
| C-82 | | A-28 | o-methylphenyl-hydrazine | 447 | 1.01 |
| C-83 | | A-29 | B-31 | 472 | 1.25 |
| C-84 | | A-30 | B-31 | 446 | 1.19 |

TABLE 1-continued

Examples C-01-C-117

| No. | MOLSTRUCTURE | Diketone | Hydrazine | [M + H]+ | rt |
|---|---|---|---|---|---|
| C-85 | | A-31 | isopropylhydrazine | 409 | 1.08 |
| C-86 | | A-35 | B-32 | 533 | |
| C-87 | | A-23 | (2-hydrazino-ethyl)-dimethyl-amine | 397 | 1.27 |
| C-88 | | A-23 | (2-morpholin-4-yl-ethyl)-hydrazine | 439 | 1.25 |
| C-89 | | A-23 | (2-trifluoromethyl-phenyl)-hydrazine | 470 | 1.58 |

TABLE 1-continued

Examples C-01-C-117

| No. | MOLSTRUCTURE | Diketone | Hydrazine | [M + H]+ | rt |
|---|---|---|---|---|---|
| C-90 | | A-23 | (2-methoxy-phenyl)-hydrazine | 432 | 1.47 |
| C-91 | | A-23 | (2-trifluoromethoxy-phenyl)-hydrazine | 486 | 1.70 |
| C-92 | | A-23 | o-methylphenyl-hydrazine | 416 | 1.89 |
| C-93 | | A-23 | isobutylhydrazine | 382 | 1.86 |
| C-94 | | A-36 | isopropylhydrazine | 441 | 1.53 |

TABLE 1-continued

Examples C-01-C-117

| No. | MOLSTRUCTURE | Diketone | Hydrazine | [M + H]+ | rt |
|---|---|---|---|---|---|
| C-95 | | A-37 | isopropylhydrazine | 468 | 1.63 |
| C-96 | | A-47 | isopropylhydrazine | 440 | 1.49 |
| C-97 | | A-39 | o-methylphenyl-hydrazine | 539 | 1.62 |
| C-98 | | A-46 | o-methylphenyl-hydrazine | 446 | 1.43 |
| C-99 | | A-38 | o-methylphenyl-hydrazine | 417 | 1.59 |

TABLE 1-continued

Examples C-01-C-117

| No. | MOLSTRUCTURE | Diketone | Hydrazine | [M + H]+ | rt |
|---|---|---|---|---|---|
| C-100 | | A-37 | o-methylphenyl-hydrazine | 516 | 1.76 |
| C-101 | | A-36 | o-methylphenyl-hydrazine | 489 | 1.75 |
| C-102 | | A-41 | o-methylphenyl-hydrazine | 460 | 1.39 |
| C-103 | | A-40 | o-methylphenyl-hydrazine | 474 | 1.49 |
| C-104 | | A-42 | o-methylphenyl-hydrazine | 488 | 1.71 |
| C-105 | | A-43 | isopropylhydrazine | 442 | 1.46 |

TABLE 1-continued

Examples C-01-C-117

| No. | MOLSTRUCTURE | Diketone | Hydrazine | [M + H]+ | rt |
|---|---|---|---|---|---|
| C-106 | | A-44 | isopropylhydrazine | 454 | 1.43 |
| C-107 | | A-45 | isopropylhydrazine | 454 | 1.44 |
| C-108 | | A-49 | o-tolylhydrazine hydrochloride | 446 | 1.53 |
| C-109 | | A-48 | o-tolylhydrazine hydrochloride | 460 | 1.59 |
| C-110 | | A-50 | o-tolylhydrazine hydrochloride | 474 | |

TABLE 1-continued

Examples C-01-C-117

| No. | MOLSTRUCTURE | Diketone | Hydrazine | [M + H]+ | rt |
|---|---|---|---|---|---|
| C-111 | | A-51 | o-tolylhydrazine hydrochloride | 517 | 1.61 |
| C-112 | | A-52 | o-tolylhydrazine hydrochloride | 504 | 1.76 |
| C-113 | | A-54 | o-tolylhydrazine hydrochloride | 518 | 1.83 |
| C-114 | | A-53 | o-tolylhydrazine hydrochloride | 531 | 1.84 |
| C-115 | | A-55 | isopropylhydrazine hydrochloride | 454 | 1.6 |

107 108

TABLE 1-continued

Examples C-01-C-117

| No. | MOLSTRUCTURE | Diketone | Hydrazine | [M + H]+ | rt |
|---|---|---|---|---|---|
| C-116 | | A-23 | 2-chloro-pyridin-3-yl-hydrazine | 437/439 | 1.55 |
| C-117 | | A-07 | 2-chloro-pyridin-3-yl-hydrazine | 452 | 1.38 |

Examples D

D-01) N-[1-(4-Amino-2-chloro-phenyl)-3-(6-methyl-pyridin-3-yl)-4,5-dihydro-1H-pyrazolo[4,3-g]benzothiazol-7-yl]-acetamide

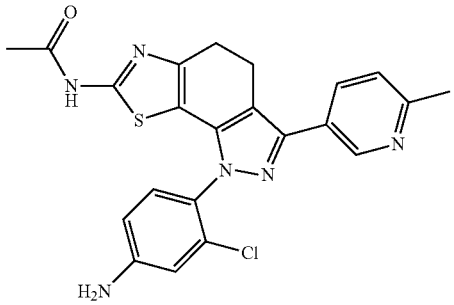

D-01a) N-[1-(2-Chloro-4-nitro-phenyl)-3-(6-methyl-pyridin-3-yl)-4,5-dihydro-1H-pyrazolo[4,3-g]benzothiazol-7-yl]-acetamide

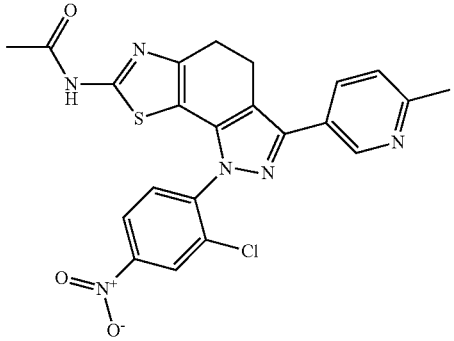

A suspension of 5.0 g (15.2 mmol) N-[6-(6-methyl-pyridine-3-carbonyl)-7-oxo-4,5,6,7-tetrahydro-benzothiazol-2-yl]-acetamide (A-23) and 3.74 g (16.7 mmol) (2-chloro-4-nitro-phenyl)-hydrazine hydrochloride in 100 mL glacial acetic acid is stirred at 60° C. After stirring for 24 h at 60° C. the solvent is evaporated, the residue taken up in 200 mL of ACN and stirred for 20 min. The solid is filtered off and dried at 40° C. yielding 5.33 g of the desired product.

A reaction mixture of 5.30 g (11.0 mmol) D-01a, 596 mg (2.20 mmol) vanadyl acetyl-acetonate and 530 mg Pt/C (5%) in 180 mL DMF and 270 mL THF is hydrogenated with a hydrogen pressure of 3 bar at RT over night. The reaction mixture is filtered over celite and the solvent is evaporated under reduced pressure. The residue is taken up in ACN. The solid material is filtered off and dried at 60° C. yielding 3.94 g D-01.

D-02) N-[1-(4-Amino-2-fluoro-phenyl)-3-(6-methyl-pyridin-3-yl)-4,5-dihydro-1H-pyrazolo[4,3-g]benzothiazol-7-yl]-acetamide

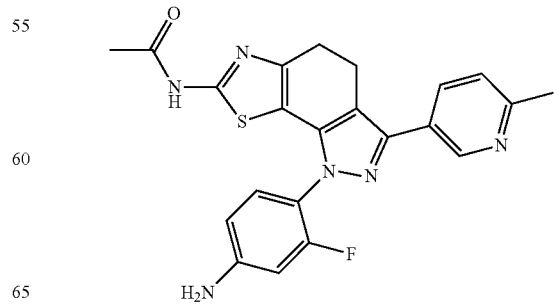

D-02a) N-[1-(2-Fluoro-4-nitro-phenyl)-3-(6-methyl-pyridin-3-yl)-4,5-dihydro-1H-pyrazolo[4,3-g]benzothiazol-7-yl]-acetamide

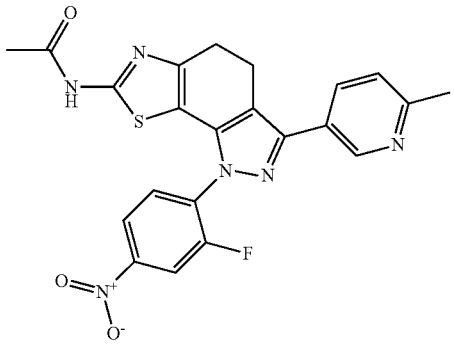

A suspension of 2.30 g (6.98 mmol) A-23 and 1.45 g (6.98 mmol) (2-fluoro-4-nitro-phenyl)-hydrazine hydrochloride in 40 mL glacial acetic acid is stirred at 40° C. over night. The solvent is evaporated, water is added and the mixture is stirred for 30 min. The formed precipitate is filtered off and dried in a vacuum drying chamber at 40° C. yielding 2.70 g D-02a.

A reaction mixture of 6.3 g (13.6 mmol) D-02a, 734 mg (2.71 mmol) vanadyl acetyl-acetonate and 700 mg Pt/C (5%) in 100 mL DMF and 150 mL THF is hydrogenated with a hydrogen pressure of 4 bar at RT over night. The reaction mixture is filtered over silica and the solvent is evaporated under reduced pressure. The residue is taken up in ACN and the solid material is filtered off and dried at 60° C. yielding 5.34 g D-02.

D-03) N-[1-(4-Bromo-phenyl)-3-(6-methyl-pyridin-3-yl)-4,5-dihydro-1H-pyrazolo[4,3-g]benzothiazol-7-yl]-acetamide

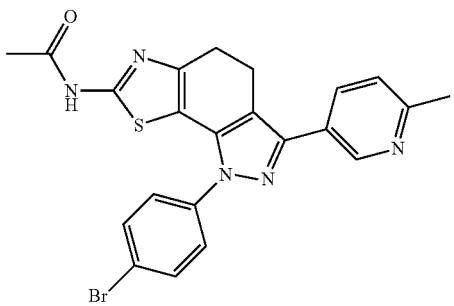

To a suspension of 10.0 g (30.4 mmol) A-23 in 40 mL glacial acetic acid is added 7.46 g (33.4 mmol) (4-Bromo-phenyl)-hydrazine hydrochloride. After stirring at RT over night the precipitation is filtered off and washed three times with EtOH. The solid is dried and yields 11 g D-03.

D-04) N-{3-(6-Methyl-pyridin-3-yl)-1-[4-(4,4,5,5-tetramethyl-1,3,2-dioxaborolan-2-yl)-phenyl]-4,5-dihydro-1H-pyrazolo[4,3-g]benzothiazol-7-yl}-acetamide

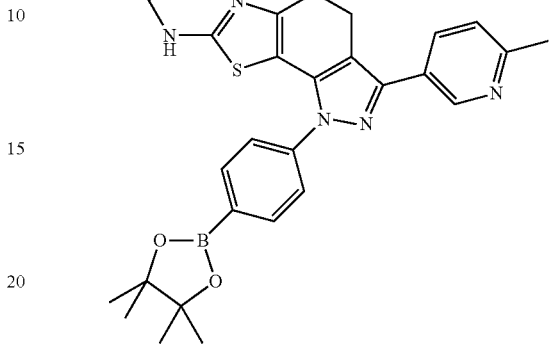

A solution of 5.50 g (11.4 mmol) D-03, 3.20 g (12.6 mmol) bis(pinacolato)diboron, 3.38 g (34.4 mmol) potassium acetate and 468 mg (0.572 mmol) palladium 1,1'-bis(diphenyl-phosphino)ferrocene dichloride DCM complex in 40 mL dry DMF is heated under an argon atmosphere at 105° C. over night. The suspension is reduced to the half volume and the precipitation is filtered off, washed twice with 5 mL water and 5 mL EtOH and dried under reduced pressure yielding 5.6 g D-04. The product is used in the next step without further purification.

D-05) N-[1-(4-Bromo-phenyl)-3-(6-ethylamino-pyridin-3-yl)-4,5-dihydro-1H-pyrazolo[4,3-g]benzothiazol-7-yl]-acetamide

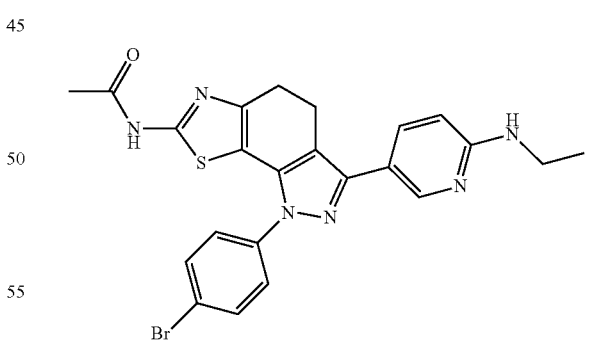

To a suspension of 4.12 g (11.5 mmol) A-10 in 30 mL glacial acetic acid is added 3.11 g (13.9 mmol) (4-bromo-phenyl)-hydrazine hydrochloride. After stirring at RT over night and 1 h at 50° C. the solvent is evaporated, the residue suspended in 25 mL MeOH and sonicated for 25 min. The solid material is filtered off and dried yielding 1.66 g D-05.

D-06) N-[1-(4-Bromo-phenyl)-3-(6-methylamino-pyridin-3-yl)-4,5-dihydro-1H-pyrazolo[4,3-g]benzothiazol-7-yl]-acetamide

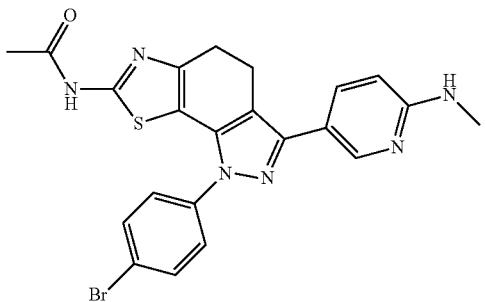

To a suspension of 4.0 g (11.6 mmol) A-07 in 30 mL glacial acetic acid is added 3.11 g (13.9 mmol) (4-bromo-phenyl)-hydrazine hydrochloride. After stirring at RT over night and 1 h at 50° C. the solvent is evaporated, the residue is suspended in 20 mL EtOH and sonicated for 25 min. The solid material is filtered off and dried yielding 2.66 g D-06, which is used without further purification.

D-07) 4-[7-Acetylamino-3-(6-methyl-pyridin-3-yl)-4,5-dihydro-pyrazolo[4,3-g]benzo-thiazol-1-yl]-cis-cyclohexanecarboxylic acid

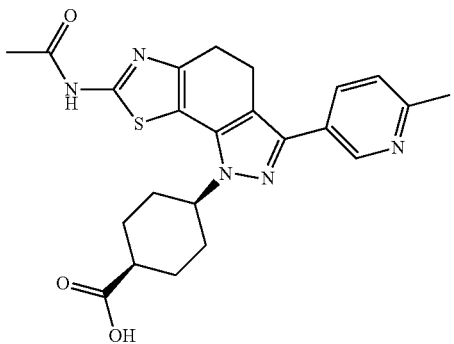

D-07a) 4-[7-Acetylamino-3-(6-methyl-pyridin-3-yl)-4,5-dihydro-pyrazolo[4,3-g]benzothiazol-1-yl]-cis-cyclohexanecarboxylic acid ethyl ester

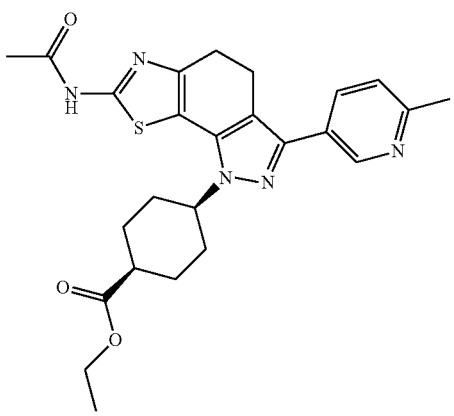

A solution of 1.30 g (3.95 mmol) A-23 and 1.01 g (4.74 mmol) 4-hydrazino-cyclohexane-carboxylic acid ethyl ester hydrochloride in 30 mL glacial acetic acid is stirred at 65° C. for 50 h. The solvent is evaporated and the residue is taken up in DMF. Purification is performed via RP-prep. HPLC chromatography (gradient 2-60% ACN). After freeze-drying 510 mg of D-07a are obtained To a solution of 737 mg (1.54 mmol) D-07a in 35 mL THF is added a solution of 294 mg (12.3 mmol) LiOH in 14 mL water. The reaction mixture is stirred at 30° C. for 3 d. Glacial acetic acid is added until pH 4-5 is reached and the solvent is evaporated under reduced pressure. The residue is taken up in DCM and water is added. The formed precipitate is filtered off. More water is added to the filtrate to drive the precipitation to completion. The combined solid fractions are dried yielding 372 mg D-07.

D-08) 4-[7-Acetylamino-3-(6-methyl-pyridin-3-yl)-4,5-dihydro-pyrazolo[4,3-g]benzo-thiazol-1-yl]-cis-cyclohexanecarboxylic acid

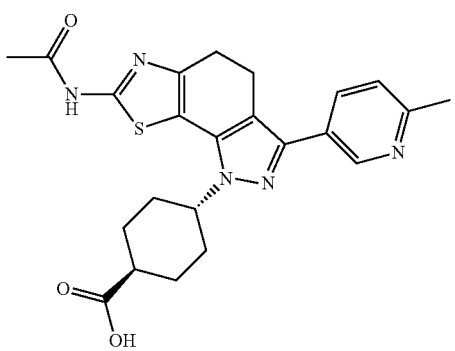

D-08a) 4-[7-Acetylamino-3-(6-methyl-pyridin-3-yl)-4,5-dihydro-pyrazolo[4,3-g]benzo-thiazol-1-yl]-trans-cyclohexanecarboxylic acid ethyl ester

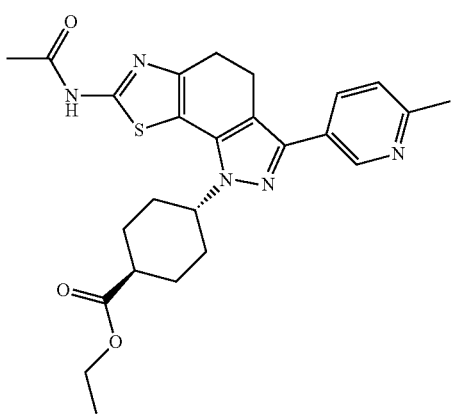

A solution of 1.30 g (3.95 mmol) A-23 and 0.967 g (4.34 mmol) 4-hydrazino-cyclohexane-carboxylic acid ethyl ester hydrochloride in 30 mL glacial acetic acid is stirred at 60° C. for 50 h. The solvent is evaporated and the residue is taken up in DMF. Purification is performed via RP-prep. HPLC chromatography (gradient 2-60% ACN). After freeze-drying 298 mg of D-08a are obtained.

To a solution of 371 mg (0.774 mmol) D-08a in 17 mL THF is added a solution of 148 mg (6.19 mmol) LiOH in 7.0 mL water. The reaction mixture is stirred at RT for 24 h. Glacial acetic acid is added until pH 4-5 is reached and the solvent is evaporated under reduced pressure. The residue is taken up in DCM and water is added. The formed precipitate is filtered off. More water is added to the filtrate to drive the precipitation to completion. The combined solid fractions are dried at 40° C. over night yielding 284 mg D-08.

D-09) N-[1-(4-Cyano-2-methyl-phenyl)-3-(6-methyl-pyridin-3-yl)-4,5-dihydro-1H-pyrazolo[4,3-g]benzothiazol-7-yl]-acetamide

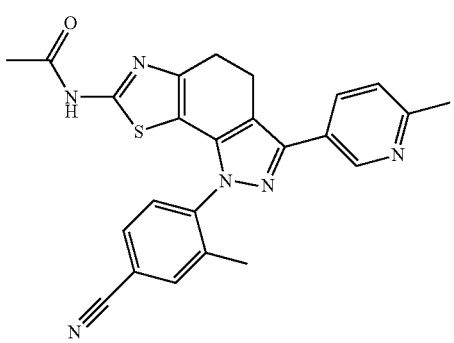

A solution of 2.50 g (8 mmol) A-23 and 1.68 g (11 mmol) 4-hydrazino-3-methyl-benzonitrile in 10 mL glacial acetic acid is stirred at 45° C. over night. The solvent is evaporated and the residue is taken up in 10 mL EtOH. After stirring over night the formed precipitate is filtered off and dried yielding 1.4 g D-09.

D-10) N-[1-(4-Formyl-2-methyl-phenyl)-3-(6-methyl-pyridin-3-yl)-4,5-dihydro-1H-pyrazolo[4,3-g]benzothiazol-7-yl]-acetamide

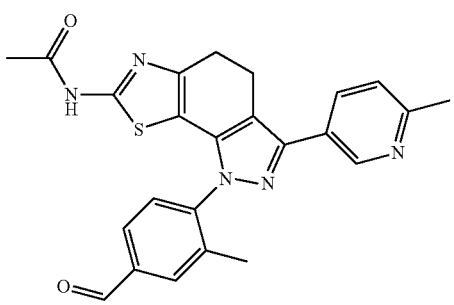

To a reaction mixture of 600 mg (1.36 mmol) D-09 in 2.0 mL glacial acetic acid, 2.0 mL pyridine and 2.0 mL water is added 1.0 g (21.7 mmol) formic acid and 300 mg Raney-nickel and stirred at 90° C. for 30 min. The reaction mixture is filtered off without cooling and washed with 5 mL glacial acetic acid. The filtrate is evaporated under reduced pressure and 10 mL of water are added to the residue. The formed precipitation is filtered off, washed with water and dried in vacuum yielding 450 mg D-10, which is used in the next step without further purification.

D-11) N-[1-(2-Bromo-4-cyano-phenyl)-3-(6-methyl-pyridin-3-yl)-4,5-dihydro-1H-pyrazolo[4,3-g]benzothiazol-7-yl]-acetamide

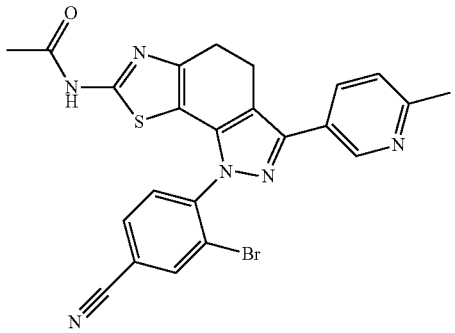

A solution of 5.0 g (15.2 mmol) A-23) and 5.20 g (22.1 mmol) 3-bromo-4-hydrazino-benzonitrile in 20 ml glacial acetic acid is stirred at 60° C. for 3 h. The solvent is evaporated and the residue is taken up in 10 mL EtOH. After stirring over night the formed precipitation is filtered off and dried, yielding 4.30 g of the desired product D-11.

D-12) N-[1-(2-Bromo-4-formyl-phenyl)-3-(6-methyl-pyridin-3-yl)-4,5-dihydro-1H-pyrazolo[4,3-g]benzothiazol-7-yl]-acetamide

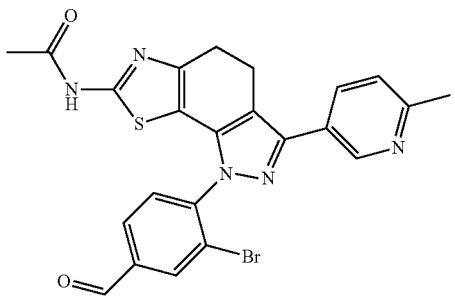

To a reaction mixture of 600 mg (1.19 mmol) D-11 in 2 mL glacial acetic acid, 2 mL pyridine and 2 mL water is added 1.0 g (21.7 mmol) formic acid and 300 mg Raney-nickel and stirred at 90° C. for 30 min. The reaction mixture is filtered off without cooling and washed twice with 20 mL MeOH/DCM. The filtrate is evaporated under reduced pressure and 10 mL of water are added to the residue. The formed precipitate is filtered off, washed twice with 3 mL water and dried in vacuum yielding 588 mg D-12, which is used in the next step without further purification.

D-13) N-[1-[2-Bromo-4-(methoxyimino-methyl)-phenyl]-3-(6-methyl-pyridin-3-yl)-4,5-dihydro-1H-pyrazolo[4,3-g]benzothiazol-7-yl]-acetamide

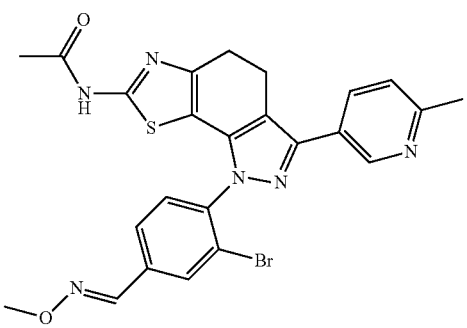

A reaction mixture of 170 mg (0.301 mmol) D-12 and 50.3 mg (0.602 mmol) O-methyl-hydroxylamine hydrochloride in 2 mL MeOH is stirred at 40° C. over night. The reaction mixture is evaporated under reduced pressure and the residue is taken up in 2 mL MeOH/DCM with 5% triethyl amine. Purification is performed via prep. HPLC yielding 150 mg of D-13.

D-14) N-[3-(6-Methyl-pyridin-3-yl)-1-piperidin-4-yl-4,5-dihydro-1H-pyrazolo[4,3-g]benzothiazol-7-yl]-acetamide

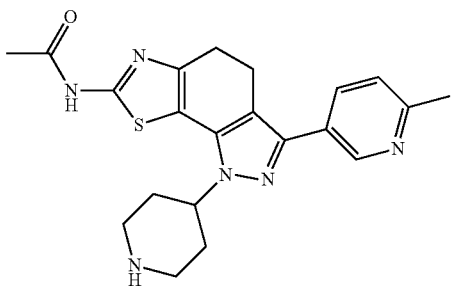

A mixture of 5.20 g (15.8 mmol) A-23 and 3.6 g (19.1 mmol) B-26 in 200 mL glacial acetic acid is stirred at 80° C. for 72 h. The solvent is evaporated and the residue is taken up in water and aqueous 5% potassium carbonate solution. The formed precipitate is filtered off and washed with water. Purification of the crude product is performed via MPLC (DCM/MeOH 93:7 as eluent) yielding 4.0 g of D-14.

D-15) [1-[4-(Methoxyimino-methyl)-phenyl]-3-(6-methyl-pyridin-3-yl)-4,5-dihydro-1H-pyrazolo[4,3-g]benzothiazol-7-yl]-thiocarbamic acid S-ethyl ester

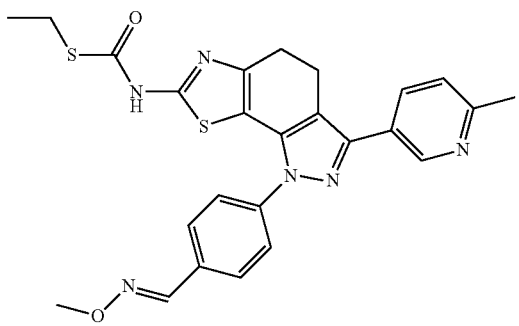

To a solution of 150 mg (0.306 mmol) D-16 in 2 mL NMP is added 153 μL (0.895 mmol) diisopropylethylamine and 122 mg (0.981 mmol) ethyl-chloro-thioformate. The reaction mixture is stirred at RT over night. Water is added to the reaction and the resultant mixture is extracted twice with 15 mL DCM. The combined organic layers are dried over Na₂SO₄ and evaporated under reduced pressure yielding 150 mg D-15 which is used in the next step without further purification.

D-16) 4-[7-Amino-3-(6-methyl-pyridin-3-yl)-4,5-dihydro-pyrazolo[4,3-g]benzothiazol-1-yl]-benzaldehyde O-methyl-oxime

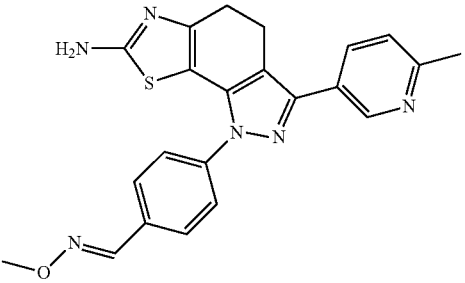

To a solution of 500 mg (1.09 mmol) D-29 in 10 mL MeOH and 3 mL DCM is added 5 mL of 4 M HCl dioxane solution. The reaction mixture is stirred at 60° C. for 6 h. The solvent is evaporated under reduced pressure and the residue is taken up in water and DCM. Potassium carbonate is added until the aqueous phase becomes basic. After phase separation the aqueous phase is extracted twice with 50 mL DCM. The combined organic layers are washed with 1 M aqueous HCl solution. Some MeOH is added to the organic layer, dried over Na₂SO₄ and the solvent is evaporated under reduced pressure yielding 113 mg D-16, which is used in the next step without further purification.

D-17) 1-Isopropyl-3-(6-methyl-pyridin-3-yl)-4,5-dihydro-1H-pyrazolo[4,3-g]benzothiazol-7-ylamine

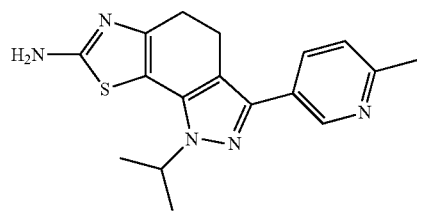

To a suspension of 4.7 g (13 mmol) C-73 in 5 mL dioxane is added dropwise 2.14 mL conc. aqueous HCl solution. After complete addition the reaction mixture is heated at 95° C. for 2 h. Saturated NaHCO₃ solution is added to the cooled reaction mixture until pH 8 is reached. The formed precipitate is filtered off, washed twice with 5 mL water and dried in vacuo yielding 3.70 g D-17, which is used for the next step without further purification.

D-18) [1-(4-Bromo-phenyl)-3-(6-methyl-pyridin-3-yl)-4,5-dihydro-1H-pyrazolo[4,3-g]benzothiazol-7-yl]-carbamic acid methyl ester

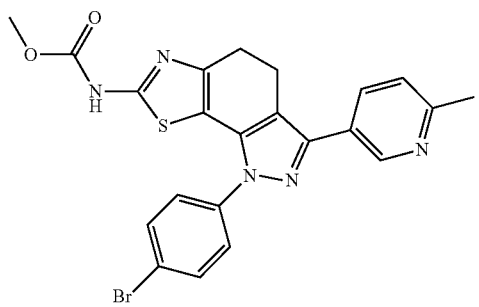

A mixture of 400 mg (1.27 mmol) A-24 and 284 mg (1.27 mmol) (4-bromo-phenyl)-hydrazine hydrochloride in 10 mL glacial acetic acid is stirred at 50° C. for 48 h. The solvent is evaporated, the residue is taken up in MeOH and sonicated for 15 min. The solid material is filtered off and dried yielding 780 mg D-18.

D-19) 4-[7-Acetylamino-3-(6-chloro-pyridin-3-yl)-4,5-dihydro-pyrazolo[4,3-g]benzo-thiazol-1-yl]-3-chloro-N,N-dimethyl-benzamide

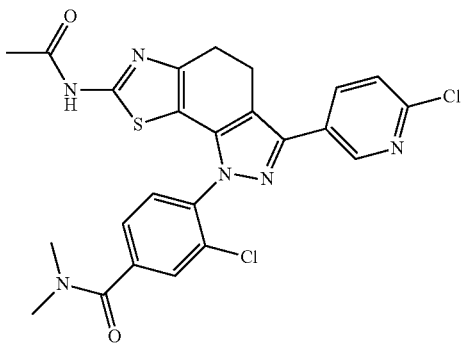

A mixture of 1.50 g (4.29 mmol) A-12 and 1.39 g (5.58 mmol) B-01 in 35 mL glacial acetic acid is stirred at 40° C. over night. The solvent is evaporated, the residue is taken up in DCM and saturated Na$_2$CO$_3$ solution. The aqueous layer is extracted twice with DCM, the combined organic layers are dried over MgSO$_4$ and evaporated under reduced pressure yielding 1.05 g D-19.

D-20) [3-(6-Ethylamino-pyridin-3-yl)-1-o-tolyl-4,5-dihydro-1H-pyrazolo[4,3-g]benzo-thiazol-7-yl]-thio-carbamic acid S-ethyl ester

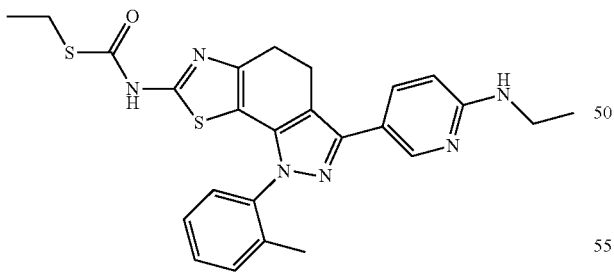

A solution of 2.50 g (4.94 mmol) A-34 and 0.941 g (1.11 mmol) 2-methyl-phenylhydrazine hydrochloride in 10 mL glacial acetic acid is stirred at 80° C. over night. The solvent is evaporated under reduced pressure and the residue is taken up in DMSO/MeOH. Solid material is filtered off and the filtrate is purified via prep. HPLC yielding 0.680 g D-20, which is used without further purification for the next step.

D-21) [1-(2-Chloro-phenyl)-3-(6-methylamino-pyridin-3-yl)-4,5-dihydro-1H-pyrazolo[4,3-g]benzothiazol-7-yl]-thiocarbamic acid S-ethyl ester

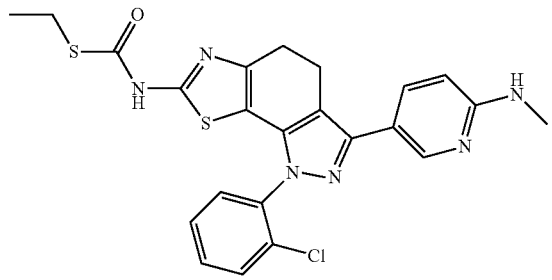

To a suspension of 200 mg (0.512 mmol) A-33 in 15 mL isopropanol is added 275 mg (1.54 mmol) 2-chlorophenylhydrazine hydrochloride. After stirring at 80° C. over night the solvent is evaporated under reduced pressure yielding 150 mg D-21, which is used without further purification for the next step.

D-22) 4-[7-Acetylamino-3-(6-methyl-pyridin-3-yl)-4,5-dihydro-pyrazolo[4,3-g]benzo-thiazol-1-yl]-3-methoxy-benzoic acid methyl ester

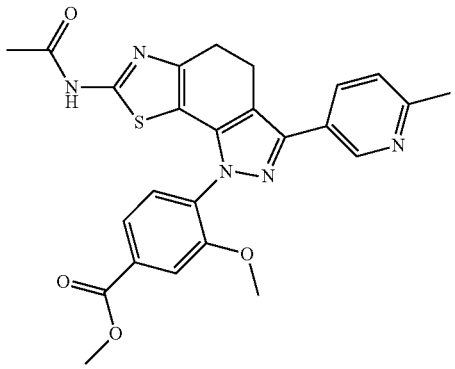

A reaction mixture of 3 g (8.93 mmol) A-23 and 2.5 g (13 mmol) B-33 in 20 mL glacial acetic acid is stirred at 60° C. over night. The solvent is evaporated and the residue is taken up in 10 mL EtOH. The precipitation is filtered off, washed twice with 4 mL of EtOH and dried yielding 3.30 g D-22.

D-23) 4-[7-Acetylamino-3-(6-methyl-pyridin-3-yl)-4,5-dihydro-pyrazolo[4,3-g]benzothiazol-1-yl]-3-methoxy-benzoic acid

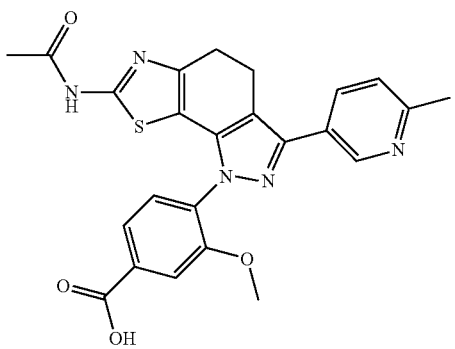

D-23 is made in analogously to D-25

D-24) 4-[7-Acetylamino-3-(6-methyl-pyridin-3-yl)-4,5-dihydro-pyrazolo[4,3-g]benzo-thiazol-1-yl]-3-ethoxy-benzoic acid methyl ester

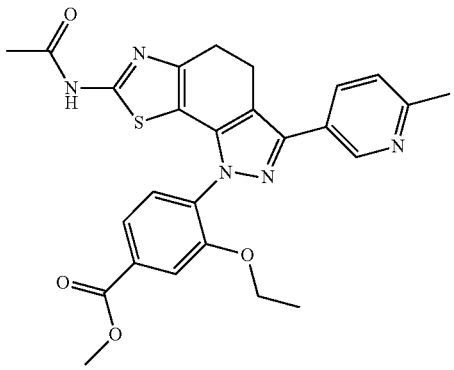

A reaction mixture of 6.72 g (22 mmol) A-23 and 4.29 g (20 mmol) B-34 in 50 mL glacial acetic acid is stirred at RT over night. The solvent is evaporated and the residue is taken up in dioxane. After freeze-drying the residue is suspended in 40 mL of EtOH and sonicated for a few minutes. The solid material is filtered off and dried yielding 4.80 g of the desired product D-24.

D-25) 4-[7-Acetylamino-3-(6-methyl-pyridin-3-yl)-4,5-dihydro-pyrazolo[4,3-g]benzo-thiazol-1-yl]-3-ethoxy-benzoic acid

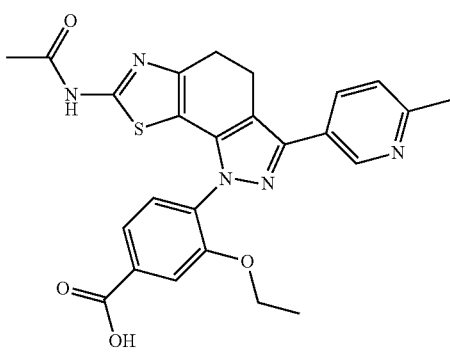

A solution of 4.80 g (9.44 mmol) D-24 and 1.61 g (37.8 mmol) LiOH in 60 mL dioxane and 12 mL water is stirred at RT for 2 h. 100 mL water and 1 M aqueous HCl solution are added to the reaction until pH 4 is reached. More water (150 mL) is added and the formed precipitation is filtered off, washed five times with 20 mL water suspended in water and dried in the freeze dryer yielding 4.30 g D-25.

D-26) N-[1-(3-Cyano-phenyl)-3-(6-methyl-pyridin-3-yl)-4,5-dihydro-1H-pyrazolo[4,3-g]benzothiazol-7-yl]-acetamide

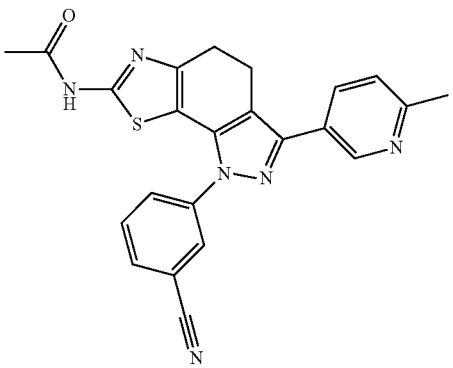

A reaction mixture of 5.04 g (15 mmol) A-23 and 2.40 g (16.2 mmol) 3-hydrazino-benzonitrile in 50 mL glacial acetic acid is stirred at RT over night. The formed precipitation is filtered off, washed twice with 75 mL glacial acetic acid and dried yielding 4.04 g D-26.

D-27) 4-[7-Acetylamino-3-(6-methyl-pyridin-3-yl)-4,5-dihydro-pyrazolo[4,3-g]benzo-thiazol-1-yl]-3-chloro-benzoic acid methyl ester

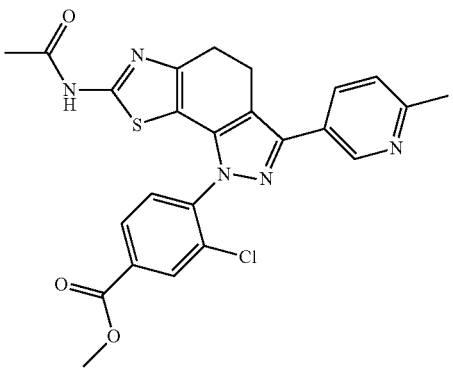

A reaction mixture of 4.16 g (12 mmol) A-23 and 2.79 g (13.2 mmol) 3-chloro-4-hydrazino-benzoic acid methyl ester in 30 mL glacial acetic acid is stirred at RT over night. The solvent is evaporated and the residue is taken up in dioxane/water. After freeze-drying the residue is suspended in 50 mL of EtOH and sonicated for a few minutes. The solid material is filtered off washed with 50 mL EtOH and dried yielding 2.61 g D-27.

D-28) 4-[7-Acetylamino-3-(6-methyl-pyridin-3-yl)-4,5-dihydro-pyrazolo[4,3-g]benzo-thiazol-1-yl]-3-chloro-benzoic acid

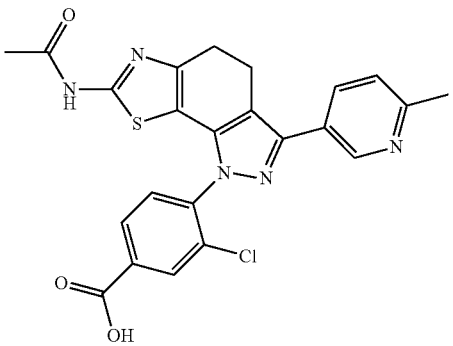

A solution of 2.60 g (5.16 mmol) D-27 and 879 mg (20.6 mmol) LiOH in 30 mL dioxane and 8 mL water is stirred at RT for 2 h. 150 mL water and 1 M aqueous HCl solution are added to the reaction until pH 4 is reached. More water (150 mL) is added and the formed precipitate is filtered off, washed five times with 20 mL water suspended in water and dried in the freeze dryer yielding 1.72 g D-28.

D-29) N-[1-[4-(Methoxyimino-methyl)-phenyl]-3-(6-methyl-pyridin-3-yl)-4,5-dihydro-1H-pyrazolo[4,3-g]benzothiazol-7-yl]-acetamide

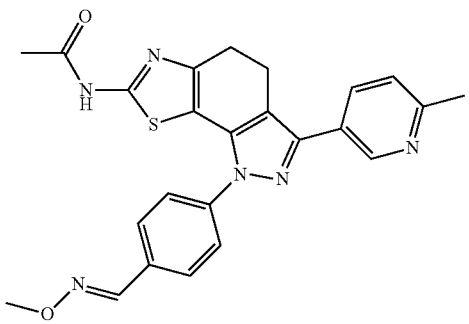

A reaction mixture of 2.00 g (6.07 mmol) A-23 and 1.74 g (7.29 mmol) B-31 in 20 mL glacial acetic acid is stirred at RT over night. The solvent is evaporated under reduced pressure. Water is added to the residue and it is extracted seven times with DCM. The combined organic layers are washed with saturated NaCl solution, dried over $Na_2SO_4$ and the solvent is evaporated under reduced pressure yielding 2.68 g D-29.

D-30) N-[3-(6-Ethyl-pyridin-3-yl)-1-piperidin-4-yl-4,5-dihydro-1H-pyrazolo[4,3-g]benzothiazol-7-yl]-acetamide

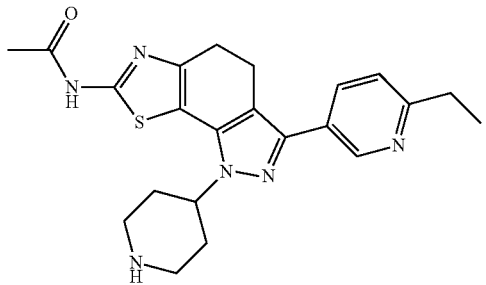

D-30 can be synthesized in analogously to D-14.

Examples E

E-01) N-[1-(2-Chloro-4-{[1-cyclobutyl-1-pyrrolidin-1-yl-meth-(E)-ylidene]-amino}-phenyl)-3-(6-methyl-pyridin-3-yl)-4,5-dihydro-1H-pyrazolo[4,3-g]benzothiazol-7-yl]-acetamide To a solution of 597 mg (3 mmol) cyclobutyl-pyrrolidin-1-yl-methanone in 2 mL dry $CH_2Cl_2$ a solution of 330 µL (3.9 mmol) oxalyl chloride in 1 mL $CH_2Cl_2$ is added and the reaction mixture is stirred at RT for 1 h. To a solution of 100 mg (0.23 mmol) D01 in 1 mL NMP the freshly prepared solution of 1-(chloro-cyclobutyl-methylene)-pyrrolidinium chloride in 3 mL $CH_2Cl_2$ is added in one portion. The reaction mixture is stirred for 10 min at RT. The $CH_2Cl_2$ is evaporated and the product isolated from the NMP solution by both RP-HPLC and NP-HPLC. Yield: 81 mg.

E-02 to E-04 are prepared in a procedure analogous to example E-01

E-05) N-[1-[4-(6-Chloro-pyridin-3-yl)-phenyl]-3-(6-methyl-pyridin-3-yl)-4,5-dihydro-1H-pyrazolo[4,3-g]benzothiazol-7-yl]-acetamide Intermediate D-04 (70 mg), 2-chloro-5-bromopyridine (38 mg) and potassium carbonate (73 mg) are added to DMF (1 mL). The reaction flask is purged with argon and tetrakis-(triphenylphosphine)palladium(0) (8 mg) is added. The reaction is heated to 110° C. for 24 h. The mixture is cooled to RT, filtered and washed with MeOH (300 µL). The resulting filtrate is purified using RP-LC/MS (ACN:$H_2O$-TFA pH 1). Yield: 3 mg.

E-06) N-[3-(6-Methyl-pyridin-3-yl)-1-(4-thiophen-3-yl-phenyl)-4,5-dihydro-1H-pyrazolo[3',4':3,4]benzo[1,2-d]thiazol-7-yl]-acetamide Intermediate D-04 (70 mg), 3-bromothiophene (33 mg) and potassium carbonate (73 mg) are added to DMF (1 mL). The reaction flask is purged with argon and tetrakis(triphenylphosphine)palladium(0) (8 mg) is added. The reaction is heated to 110° C. for 24 h. The mixture is cooled to RT, filtered and washed with MeOH (300 µL). The resulting filtrate is purified using RP-LC/MS (ACN:$H_2O$-TFA pH 1). Yield: 2 mg.

E-07) N-[1-(2'-Methoxy-biphenyl-4-yl)-3-(6-methyl-pyridin-3-yl)-4,5-dihydro-1H-pyrazolo[3',4':3,4]benzo[1,2-d]thiazol-7-yl]-acetamide Intermediate D-04 (70 mg), 2-bromoanisol (37 mg) and potassium carbonate (73 mg) are added to DMF (1 mL). The reaction flask was purged with argon and tetrakis(triphenylphosphine)palladium(0) (8 mg) is added. The reaction is heated to 110° C. for 24 h. The mixture is cooled to RT, filtered and washed with MeOH (300 µL). The resulting filtrate is purified using RP-LC/MS (ACN:$H_2O$-TFA pH 1). Yield: 20 mg, 30.

E-08) N-{3-(6-Methyl-pyridin-3-yl)-1-[4-(4-methyl-pyridin-3-yl)-phenyl]-4,5-dihydro-1H-pyrazolo[4,3-g]benzothiazol-7-yl}-acetamide Intermediate D-04 (150 mg), 3-bromo-4-methylpyridine (50 µL) and potassium carbonate (390 mg) are added to DMF (5 mL). The reaction flask is purged with argon and tetrakis-(triphenylphosphine)palladium(0) (8 mg) is added. The reaction is heated to 100° C. for 3.5 h. The mixture is cooled to RT and added to DCM (15 mL). The resulting mixture is filtered and washed with DCM (15 mL). The DCM is removed under reduced pressure and the resulting DMF solution is purified using RP-LC/MS (ACN:$H_2O$-TFA pH 1). Yield: 16 mg.

E-09) N-[3-(6-Ethylamino-pyridin-3-yl)-1-(4-pyridin-3-yl-phenyl)-4,5-dihydro-1H-pyrazolo[4,3-g]benzothiazol-7-yl]-acetamide Intermediate D-05 (156 mg), pyridine-3-boronic acid (80 mg) and potassium carbonate (275 mg) are added to DMF (4 mL). The reaction flask is purged with argon and tetrakis-(triphenylphosphine)palladium(0) (35 mg) is added. The reaction is heated to 100° C. for 24 h. The mixture is cooled to RT and added to DCM (15 mL). The resulting mixture is filtered and washed with DCM (15 mL). The DCM was removed under reduced pressure and the resulting DMF solution is purified using RP-LC/MS (ACN:H$_2$O-TFA pH 1). Yield: 49 mg.

E-10) N-{3-(6-Ethylamino-pyridin-3-yl)-1-[4-(2-methyl-pyridin-4-yl)-phenyl]-4,5-dihydro-1H-pyrazolo[4,3-g]benzothiazol-7-yl}-acetamide Intermediate D-05 (515 mg), 4-methylpyridine-4-boronic acid pinacol ester (480 mg) and potassium carbonate (990 mg) were added to DMF (15 mL). The reaction flask was purged with argon and tetrakis(triphenylphosphine)palladium(0) (120 mg) was added. The reaction was heated to 100° C. for 24 h. The mixture was cooled to RT and added to DCM (15 mL). The resulting mixture was filtered and washed with DCM (15 mL). The DCM was removed under reduced pressure and the resulting DMF solution was purified using RP-LC/MS (ACN:H$_2$O-TFA pH 1). Yield: 120 mg.

E-11) N-{3-(6-Methylamino-pyridin-3-yl)-1-[4-(2-methyl-pyridin-4-yl)-phenyl]-4,5-dihydro-1H-pyrazolo[4,3-g]benzothiazol-7-yl}-acetamide Intermediate D-06 (500 mg), 2-methylpyridine-4-boronic acid pinacol ester (480 mg) and potassium carbonate (990 mg) were added to DMF (15 mL). The reaction flask was purged with argon and tetrakis(triphenylphosphine)palladium(0) (120 mg) was added. The reaction was heated to 110° C. for 2 h in the microwave. The mixture was cooled to RT and added to DCM (15 mL). The resulting mixture was filtered and washed with DCM (15 mL). The DCM was removed under reduced pressure and the resulting DMF solution was purified using RP-LC/MS (ACN:H$_2$O-TFA pH 1). Yield: 226 mg.

E-12) 4-[(S)-7-Acetylamino-3-(6-methyl-pyridin-3-yl)-4,5-dihydro-pyrazolo[4,3-g]benzo-thiazol-1-yl]-cyclohexanecarboxylic acid methyl-(1-methyl-piperidin-4-yl)-amide To a suspension of 40 mg (0.09 mmol) D07 in DMF 45 µL (0.27 mmol) DIPEA 40 mg (0.11 mmol) HATU are added. The mixture is stirred at RT for 15 min before 14 µL (0.10 mmol) 1-methyl-4-(methylamino)piperidine are added. The mixture is stirred overnight. The precipitated product is collected and washed with a saturated solution of NaHCO$_3$ and water. Finally, the product is dried in vacuo. Yield: 30 mg.

E-13 and E-14 are prepared in a procedure analogous to example E-12. If the compounds did not precipitate in sufficient purity they are purified by prep. HPLC-MS.

E-15) N-[1-[4-(Methoxyimino-methyl)-2-methyl-phenyl]-3-(6-methyl-pyridin-3-yl)-4,5-dihydro-1H-pyrazolo[4,3-g]benzothiazol-7-yl]-acetamide Intermediate D-10 (3.3 g) and methoxyamine hydrochloride (1.3 g) are added to MeOH (20 mL) and allowed to stir at 40° C. for 30 min. The solvent is then removed under reduced pressure, 5 mL NMP are added and the resulting solution is purified using RP-LC/MS (ACN:H$_2$O-ammonium hydrogen carbonate pH 9.3). Yield: 1.78 g.

E-16) N-[1-[4-(Isopropoxyimino-methyl)-2-methyl-phenyl]-3-(6-methyl-pyridin-3-yl)-4,5-dihydro-1H-pyrazolo[4,3-g]benzothiazol-7-yl]-acetamide Intermediate D-10 (70 mg) and isopropoxyamine hydrochloride (42 mg) are added to MeOH (2 mL) and allowed to stir at 40° C. overnight. The solvent is then removed under reduced pressure, dissolved in a mixture of MeOH/DCM, and purified using RP-LC/MS (ACN:H$_2$O-ammonium hydrogen carbonate pH 9.3). Yield: 48 mg.

E-17) N-[1-[2-Ethynyl-4-(methoxyimino-methyl)-phenyl]-3-(6-methyl-pyridin-3-yl)-4,5-dihydro-1H-pyrazolo[4,3-g]benzothiazol-7-yl]-acetamide Intermediate D-13 (70 mg), trimethylsilylacetylene (15 mg), copper(I)iodide (1 mg), bis-(triphenylphosphine)palladium(II) chloride (5 mg), triphenylphosphine (7 mg), and diethylamine (500 µL) are added to DMSO (500 µL). The reaction is then heated to 115° C. for 100 seconds in the microwave. The reaction mixture is filtered and purified using RP-LC/MS (ACN:H$_2$O-ammonium hydrogen carbonate pH 9.3). This material is then dissolved in THF (1 mL) and TBAF (100 µL of a 1 M solution in THF) is added. The reaction mixture is heated at 40° C. for 1 h. The reaction mixture is filtered and purified using RP-LC/MS (ACN:H$_2$O-ammonium hydrogen carbonate pH 9.3). Yield: 7 mg.

E-18) N-[1-[4-(Methoxyimino-methyl)-2-prop-1-ynyl-phenyl]-3-(6-methyl-pyridin-3-yl)-4,5-dihydro-1H-pyrazolo[4,3-g]benzothiazol-7-yl]-acetamide Intermediate D-13 (140 mg), lithium chloride (33 mg), bis-(triphenylphosphine)-palladium(II)chloride (18 mg) and triphenylphosphine (27 mg) are added to DMSO and allowed to stir at RT for 5 min. Tributyl(1-propynyl)-tin (171 mg) is then added portion-wise and the reaction mixture is then heated at 105° C. for 25 min. The reaction mixture is filtered and purified using RP-LC/MS (ACN:H$_2$O-ammonium hydrogen carbonate pH 9.3). Yield: 35 mg.

E-19) 4-[7-Acetylamino-3-(6-methyl-pyridin-3-yl)-4,5-dihydro-pyrazolo[4,3-g]benzo-thiazol-1-yl]-piperidine-1-carboxylic acid dimethylamide To a mixture of D-14 (15 mg, 367 µmol) and triethylamine (76.3 µL, 551 µmol) in 2 mL THF is added at 0° C. dimethylcarbamoylchloride (33.7 µL, 367 µmol). The reaction mixture is stirred overnight at RT. The reaction mixture is filtered and the solids are dried in vacuo at 40° C. Yield: 15 mg E-20 to E-26 are prepared with a procedure analogous to example E-19.

E-27) N-{3-(6-Methyl-pyridin-3-yl)-1-[1-(3-pyridin-3-yl-prop-2-ynyl)-piperidin-4-yl]-4,5-dihydro-1H-pyrazolo[4,3-g]benzothiazol-7-yl}-acetamide A mixture of D-14 (10 mg, 245 µmol), formaldehyde (37% in water, 92 µL, 1.22 mmol), copper(I) bromide (70.2 mg, 490 µmol), 3-ethynylpyridine (50.5 mg, 490 µmol) and molsieves (4 Å) in 5 mL dry dioxane under an argon atmosphere is stirred at 80° C. for 1 h. The reaction mixture is filtered, DCM added and the reaction mixture is washed with water and brine. The organic phase is dried over MgSO$_4$ and concentrated in vacuo. The residue is purified by preparative RP-HPLC (5-98% ACN in water). Yield: 8.2 mg.

Example E-28 is prepared analogous to example E-27.

E-30) N-[3-(6-Methyl-pyridin-3-yl)-1-(1-pyridin-2-ylmethyl-piperidin-4-yl)-4,5-dihydro-1H-pyrazolo[4,3-g]benzothiazol-7-yl]-acetamide A mixture of D-14 (8.00 g, 19.6 mmol), 2-pyridinecarboxaldehyde (3.15 g, 29.4 mmol) and acetic acid (3.7 mL, 43.1 mmol) in 60 mL MeOH/DCM (1/1, v/v) is stirred for 2 h at RT. Then sodium trisacetoxyborohydride (12.5 g, 58.5 mmol) is added and the reaction mixture is stirred overnight at RT and then 2 h at 40° C. The reaction mixture is poured on saturated aqueous sodium hydrogencarbonate and extracted with DCM containing 10% MeOH. The combined organic phases are dried over $Na_2SO_4$ and concentrated in vacuo. The residue is purified by triturating with ethyl acetate, flash chromatography (silica gel, 0-10% MeOH in DCM containing 0.5% ammonia) and finally by triturating with EtOH and dioxane. Yield: 3.61 g.

E-29 and E-31 are prepared with a procedure analogous to example E-30.

E-32) [1-[4-(Methoxyimino-methyl)-phenyl]-3-(6-methyl-pyridin-3-yl)-4,5-dihydro-1H-pyrazolo[4,3-g]benzothiazol-7-yl]-urea A solution of 50 mg (010 mmol) D-15 and ammonia in 1 mL NMP is stirred at 90° C. over night. The reaction mixture is purified using RP-LC/MS (ACN:$H_2O$-TFA pH 1-2). Yield: 1.13 mg.

E-33) N-[1-[4-(Methoxyimino-methyl)-phenyl]-3-(6-methyl-pyridin-3-yl)-4,5-dihydro-1H-pyrazolo[4,3-g]benzothiazol-7-yl]-propionamide To a solution of 50 mg (0.12 mmol) D-16 in 1 mL NMP is added 60 μL (0.351 mmol) diisopropylethylamine and 32 μL (0.367 mmol) propionyl chloride and stirred at RT for 6 h. The reaction mixture is purified using RP-LC/MS (ACN:$H_2O$-formic acid pH 2-3). Yield: 20 mg.

E-34) 2-Methoxy-N-[1-[4-(methoxyimino-methyl)-phenyl]-3-(6-methyl-pyridin-3-yl)-4,5-dihydro-1H-pyrazolo[4,3-g]benzothiazol-7-yl]-acetamide To a solution of 100 mg (0.204 mmol) D-16 in 1 mL NMP is added 102 μL (0.597 mmol) diisopropylethylamine and 60 μL (0.658 mmol) methoxy-acetyl chloride and stirred at RT over night. The reaction mixture is purified using RP-LC/MS (ACN:$H_2O$-formic acid pH 2-3). Yield: 46.9 mg.

E-35) 2-Hydroxy-N-[1-[4-(methoxyimino-methyl)-phenyl]-3-(6-methyl-pyridin-3-yl)-4,5-dihydro-1H-pyrazolo[4,3-g]benzothiazol-7-yl]-acetamide To a solution of 453 mg (0.331 mmol) D-16 in 1 mL NMP is added 165 μL (0.964 mmol) diisopropylethylamine and 226 μL (1.99 mmol) acetoxy-acetyl chloride and stirred at RT for 30 min. 20 mL Water are added to the reaction and the resultant mixture is extracted three times with 25 mL DCM. The combined organic layers are dried over $Na_2SO_4$ and the solvent is evaporated under reduced pressure. The isolated crude product is dissolved in 5 mL MeOH and 2 mL (33.1 mmol, 32%) ammonia solution is added. After stirring at RT for 2 h the solvent is evaporated under reduced pressure and the residue is taken up in NMP. The reaction mixture is purified using RP-LC/MS (ACN:$H_2O$-formic acid pH 2-3). Yield: 22.7 mg.

E-36) Cyclobutanecarboxylic acid [1-isopropyl-3-(6-methyl-pyridin-3-yl)-4,5-dihydro-1H-pyrazolo[4,3-g]benzothiazol-7-yl]-amide Intermediate D-17 (150 mg) and di-isopropylethyl amine (0.18 g) are dissolved in NMP (1 mL). Cyclobutanecarbonyl chloride (0.16 g) is then added and the reaction mixture is allowed to stir at RT for 2 h. MeOH (1 mL) and 1 drop of HCL (conc.) is added and allowed to stir for 10 min at RT. The reaction mixture is filtered and purified using RP-LC/MS (ACN:$H_2O$-ammonium hydrogen carbonate pH 9.3). Yield: 52 mg.

E-37) N-[1-Isopropyl-3-(6-methyl-pyridin-3-yl)-4,5-dihydro-1H-pyrazolo[4,3-g]benzothiazol-7-yl]-isobutyramide Intermediate D-17 (150 mg) and di-isopropylethyl amine (0.18 g) are dissolved in NMP (1 mL). isobuteric acid chloride (0.15 g) is then added and the reaction mixture is stirred at RT for 2 h. MeOH (1 mL) and 1 drop of HCL (conc.) is then added and the mixture stirred for 10 min at RT. The reaction mixture is filtered and purified using RP-LC/MS (ACN:$H_2O$-ammonium hydrogen carbonate pH 9.3). Yield: 57 mg.

E-38) Cyclopropanecarboxylic acid [1-isopropyl-3-(6-methyl-pyridin-3-yl)-4,5-dihydro-1H-pyrazolo[4,3-g]benzothiazol-7-yl]-amide Cyclopropylcarboxylic acid (0.12 g), diisopropylethyl amine (0.12 g) and TBTU (0.44 g) are dissolved in DCM (1 mL) and allowed to react at 30° C. for 30 min. A solution of intermediate D-17 (150 mg) in NMP (1 mL) is then added dropwise to reaction mixture which is then heated at 90° C. for 4 h. MeOH (1 mL) and 1 drop of HCl (conc.) is then added and the mixture stirred for 10 min at RT. The reaction mixture is filtered and purified using RP-LC/MS (ACN:$H_2O$-ammonium hydrogen carbonate pH 9.3). Yield: 70 mg.

E-39) N-[1-Isopropyl-3-(6-methyl-pyridin-3-yl)-4,5-dihydro-1H-pyrazolo[4,3-g]benzothiazol-7-yl]-formamide Formic acid (0.53 mL) and acetic acid anhydride (0.65 mL) are added together and stirred at 30° C. for 30 min. The solution is cooled to 0° C. and intermediate D-17 (150 mg) is added. The reaction is allowed to react overnight at 30° C. The reaction mixture is then added to isopropanol (10 mL) and the resulting solid is removed via filtration and dried in vacuo. Yield: 119 mg.

E-40) [1-[4-(4-Methyl-piperazin-1-yl)-phenyl]-3-(6-methyl-pyridin-3-yl)-4,5-dihydro-1H-pyrazolo[4,3-g]benzothiazol-7-yl]-carbamic acid methyl ester To a solution of 200 mg (0.302 mmol) D-18 in 2 mL DMSO is added under nitrogen 105 mg (0.936 mmol) potassium 2-methyl-propan-2-olate, 70 mg (0.103 mmol) PEPPSI and 70 μL (0.630 mmol) 1-methyl-piperazine. The reaction mixture is heated under microwave irradiation at 130° C. for 45 min. The reaction mixture is purified using RP-LC/MS (ACN:$H_2O$-ammonium hydrogen carbonate pH 9.3). Yield: 10.9 mg.

E-41) [1-{4-[4-(4-Methyl-piperazin-1-yl)-piperidin-1-yl]-phenyl}-3-(6-methyl-pyridin-3-yl)-4,5-dihydro-1H-pyrazolo[4,3-g]benzothiazol-7-yl]-carbamic acid methyl To a solution of 200 mg (0.302 mmol) D-18 in 2 mL DMSO is added under nitrogen 105 mg (0.936 mmol) potassium 2-methyl-propan-2-olate, 70 mg (0.103 mmol) PEPPSI and 110 mg (0.600 mmol) 1-methyl-4-piperidin-4-yl-piperazine. The reaction mixture is heated under microwave irradiation (Biotage) at 130° C. for 45 min. The reaction mixture is purified using RP-LC/MS (ACN:$H_2O$-ammonium hydrogen carbonate pH 9.3).
Yield: 4.6 mg.

E-42) 4-{7-Acetylamino-3-[6-(3-dimethylamino-prop-1-ynyl)-pyridin-3-yl]-4,5-dihydro-pyrazolo[4,3-g]benzothiazol-1-yl}-3-chloro-N,N-dimethyl-benzamide A reaction mixture of 70 mg (0.133 mmol) D-19, 13.2 g (0.159 mmol) dimethyl-prop-2-ynyl-amine, 2.52 mg (0.013 mmol) CuI, 9.32 mg (0.013 mmol) bis-(triphenyl-phosphane)-palladium(II) dichloride and 6.96 mg (0.027 mmol) triphenyl-phosphane in 500 μL diethylamine and 500 μL DMSO under argon is heated under microwave irradiation (Biotage) at 90° C. for 90 min. The reaction mixture is purified using RP-LC/MS (ACN:$H_2O$-formic acid pH 2-3). Yield: 20 mg.

E-43) 4-{7-Acetylamino-3-[6-(3-methoxy-prop-1-ynyl)-pyridin-3-yl]-4,5-dihydro-pyrazolo[4,3-g]benzothiazol-1-yl}-3-chloro-N,N-dimethyl-benzamide A reaction mixture of 100 mg (0.190 mmol) D-19, 29 μL (0.341 mmol) 3-methoxy-propyne, 3.6 mg (0.019 mmol) CuI, 26.6 mg (0.038 mmol) bis-(triphenyl-phosphane)-palladium(II) dichloride and 9.94 mg (0.038 mmol) triphenyl-phosphane in 500 μL diethylamine and 500 μL DMSO under argon is heated under microwave irradiation (Biotage) at 100° C. for 120 min. The reaction mixture is purified using RP-LC/MS (ACN:$H_2O$-ammonium hydrogen carbonate pH 9.3). Yield: 30 mg.

E-44) 4-[7-Acetylamino-3-(6-cyclopropylethynyl-pyridin-3-yl)-4,5-dihydro-pyrazolo[4,3-g]benzothiazol-1-yl]-3-chloro-N,N-dimethyl-benzamide A reaction mixture of 70 mg (0.133 mmol) D-19, 15.8 mg (0.239 mmol) ethynyl-cyclopropane, 2.52 mg (0.013 mmol) CuI, 9.32 mg (0.013 mmol) bis-(triphenyl-phosphane)-palladium(II) dichloride and 6.96 mg (0.027 mmol) triphenyl-phosphane in 500 μL diethylamine and 500 μL DMSO under argon is heated under microwave irradiation at 100° C. for 150 min. The reaction mixture is purified using RP-LC/MS (ACN:$H_2O$-ammonium hydrogen carbonate pH 9.3). Yield: 26 mg.

E-45) 4-{7-Acetylamino-3-[6-(3-hydroxy-prop-1-ynyl)-pyridin-3-yl]-4,5-dihydro-pyrazolo[4,3-g]benzothiazol-1-yl}-3-chloro-N,N-dimethyl-benzamide A reaction mixture of 70 mg (0.133 mmol D-19, 8.93 mg (0.159 mmol) prop-2-yn-1-ol, 2.52 mg (0.013 mmol) CuI, 9.32 mg (0.013 mmol) bis-(triphenyl-phosphane)-palladium(II) dichloride and 6.96 mg (0.027 mmol) triphenyl-phosphane in 500 μL diethylamine and 500 μl DMSO under argon is heated under microwave irradiation at 100° C. for 30 min. The reaction mixture is purified using RP-LC/MS (ACN:$H_2O$-ammonium hydrogen carbonate pH 9.3). Yield: 23 mg.

E-46) 4-[7-Acetylamino-3-(6-phenylethynyl-pyridin-3-yl)-4,5-dihydro-pyrazolo[4,3-g]benzothiazol-1-yl]-3-chloro-N,N-dimethyl-benzamide A reaction mixture of 150 mg (0.284 mmol) D-19, 34.9 mg (0.341 mmol) ethynylbenzene, 5.4 mg (0.028 mmol) CuI, 20.0 mg (0.028 mmol) bis-(triphenyl-phosphane)-palladium (II) dichloride and 14.9 mg (0.057 mmol) triphenyl-phosphane in 500 μL diethylamine and 500 μL DMSO under argon is heated under microwave irradiation (Biotage) at 100° C. for 60 min. The reaction mixture is purified using RP-LC/MS (ACN:$H_2O$-ammonium hydrogen carbonate pH 9.3). Yield: 8 mg.

E-47) 3-[3-(6-Ethylamino-pyridin-3-yl)-1-o-tolyl-4,5-dihydro-1H-pyrazolo[4,3-g]benzothiazol-7-yl]-1,1-dimethyl-urea To 700 μL of a 1 M solution of dimethylamine in THF is added 170 mg (0.346 mmol) D-20. The reaction mixture is heated at 85° C. for 2 h, TFA is added to the reaction mixture and purification is performed using RP-LC/MS (ACN:$H_2O$-TFA pH 1-2). Yield: 109 mg.

E-48) 1-Ethyl-3-[3-(6-ethylamino-pyridin-3-yl)-1-o-tolyl-4,5-dihydro-1H-pyrazolo[4,3-g]benzothiazol-7-yl]-1-methyl-urea A solution of 170 mg (0.346 mmol) D-20 and 60 μL (0.698 mmol) ethylmethylamine in 200 μL THF is heated at 85° C. for 2 h. The solid material is filtered off and the filtrate is purified performed using RP-LC/MS (ACN:$H_2O$-TFA pH 1-2). Yield: 54.3 mg.

E-49) Azetidine-1-carboxylic acid [1-(2-chloro-phenyl)-3-(6-methylamino-pyridin-3-yl)-4,5-dihydro-1H-pyrazolo[4,3-g]benzothiazol-7-yl]-amide A solution of 200 mg (0.42 mmol) D-21, 240 μL (4.2 mmol) azetidine and 271 μL (2.1 mmol) diisopropylethylamine in 10 mL isopropanol is heated under microwave irradiation at 100° C. for 40 min. The solvent is evaporated under reduced pressure, the residue is taken up in NMP and 3 drops of TFA are added. The solution is purified with RP-LC/MS (ACN:$H_2O$-TFA pH 1-2). Yield: 65 mg.

E-50) 4-[7-Acetylamino-3-(6-methyl-pyridin-3-yl)-4,5-dihydro-pyrazolo[4,3-g]benzothiazol-1-yl]-3,N-dimethoxy-N-methyl-benzamide Intermediate D-23 (500 mg), diisopropylethylamine (0.5 g) and HATU (0.6 g) are dissolved in DCM (10 mL). The reaction mixture is stirred at RT for 10 min, then 1,2-dimethylhydroxylamine (0.12 g) is added and stirred for 1 h at RT. Then the solvent is removed under reduced pressure and isopropanol (5 mL) is added followed by water (5 mL). The resulting precipitate is collected via filtration, washed with water (5 mL) and the solid is dried under reduced pressure. Yield: 460 mg.

E-51) 4-[7-Acetylamino-3-(6-methyl-pyridin-3-yl)-4,5-dihydro-pyrazolo[4,3-g]benzothiazol-1-yl]-3-ethoxy-N,N-dimethyl-benzamide Intermediate D-25 (500 mg), 1,1'-carbonyldiimidazole (96 mg) are added to ethylacetate (2.4 mL) and NMP (0.6 mL).

The reaction mixture is then stirred at RT for 30 min. Dimethylamine (250 μL, 2 M solution in THF) is then added and allowed to react at RT overnight. The solvent is then removed under reduced pressure, dissolved in NMP, filtered and purified using RP-LC/MS (ACN:H₂O-ammonium hydrogen carbonate pH 9.3). Yield: 124 mg.

E-52) N-[1-[3-(Methoxyimino-methyl)-phenyl]-3-(6-methyl-pyridin-3-yl)-4,5-dihydro-1H-pyrazolo[4,3-g]benzothiazol-7-yl]-acetamide Intermediate D-26 (106 mg) and methoxylamine hydrochloride (128 mg) is dissolved in DCM/MeOH (50:50, 20 mL). Raney nickel (220 mg) and sodium hypophosphite hydrate (220 mg) are then added at RT and the reaction mixture is stirred for 2 h. The resulting mixture is filtered and the filtrate is reduced under reduced pressure. The resulting oil is filtered and the filtrate dissolved in NMP and purified using RP-LC/MS (ACN:H₂O-formic acid pH 2-3). Yield: 10 mg.

E-53) 4-[7-Acetylamino-3-(6-methyl-pyridin-3-yl)-4,5-dihydro-pyrazolo[4,3-g]benzothiazol-1-yl]-3-chloro-benzoic acid ethyl ester Intermediate D-28 (73 mg) and HATU (0.67 g) are dissolved in NMP (1 mL) and stirred for 20 min at RT. Diisopropylethylamine (30 μL) and EtOH (63 μL) are then added and stirred at RT for 4 h. The reaction mixture is then filtered and purified using RP-LC/MS (ACN:H₂O-ammonium hydrogen carbonate pH 9.3). Yield: 34 mg.

E-54) N-[1-[2-Chloro-4-(4-fluoro-piperidine-1-carbonyl)-phenyl]-3-(6-methyl-pyridin-3-yl)-4,5-dihydro-1H-pyrazolo[4,3-g]benzothiazol-7-yl]-acetamide Intermediate D-28 (100 mg), TBTU (100 mg), diisopropylethyl amine (106 μl) are dissolved in DMF (1 mL) and stirred at 35° C. overnight. The reaction mixture is then filtered and purified using RP-LC/MS (ACN:H₂O-TFA pH 1). Yield: 15 mg.

E-55) N-[1-(4-Acetyl-2-methoxy-phenyl)-3-(6-methyl-pyridin-3-yl)-4,5-dihydro-1H-pyrazolo[4,3-g]benzothiazol-7-yl]-acetamide E-50 (250 mg) is dissolved in THF (15 mL) and placed under an atmosphere of argon. A methyllithium solution (1.5 M, 2.6 mL) is then added over 1 min and the reaction mixture stirred at RT for a further 1 h. Saturated ammonium chloride solution (1 mL) is added and the THF is removed under reduced pressure. The resulting material is dissolved in DMSO (1.8 mL) and water (0.2 mL) and purified using RP-LC/MS (ACN:H₂O-TFA pH 1). Yield: 12 mg.

TABLE 2

Examples E-01-E-55

| No. | MOLSTRUCTURE | Intermediate | [M + H]⁺ | rt |
|---|---|---|---|---|
| E-01 |  | D-01 | 586 | 1.29 |
| E-02 |  | D-01 | 576 | 1.15 |

TABLE 2-continued

Examples E-01-E-55

| No. | MOLSTRUCTURE | Intermediate | [M + H]+ | rt |
|---|---|---|---|---|
| E-03 | | D-01 | 546 | 1.16 |
| E-04 | | D-02 | 516 | 1.09 |
| E-05 | | D-04 | 513 | 1.17 |

TABLE 2-continued

Examples E-01-E-55

| No. | MOLSTRUCTURE | Intermediate | [M + H]+ | rt |
|---|---|---|---|---|
| E-06 | | D-04 | 484 | 2.14 |
| E-07 | | D-04 | 508 | 1.27 |
| E-08 | | D-04 | 493 | 1.14 |

TABLE 2-continued
Examples E-01-E-55
| No. | MOLSTRUCTURE | Intermediate | [M + H]⁺ | rt |
|---|---|---|---|---|
| E-09 | 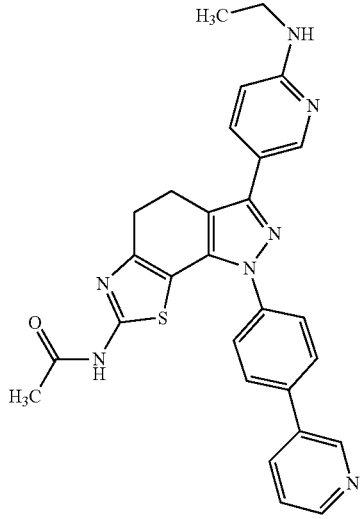 | D-05 | 508 | 1.1 |
| E-10 | 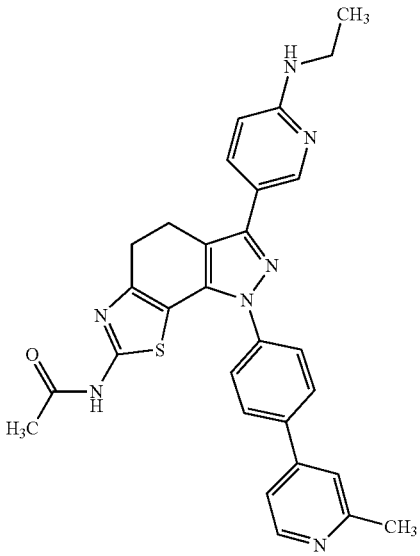 | D-05 | 522 | 1.16 |

TABLE 2-continued

Examples E-01-E-55

| No. | MOLSTRUCTURE | Intermediate | [M + H]+ | rt |
|-----|--------------|--------------|----------|-----|
| E-11 | | D-06 | 508 | 1.1 |
| E-12 | | D-07 | 562 | 1.05 |
| E-13 | | D-08 | 562 | 1.11 |

TABLE 2-continued

Examples E-01-E-55

| No. | MOLSTRUCTURE | Intermediate | [M + H]+ | rt |
|---|---|---|---|---|
| E-14 | | D-08 | 507 | 1.22 |
| E-15 | | D-10 | 473 | 1.16 |
| E-16 | | D-10 | 501 | 1.28 |
| E-17 | | D-13 | 483 | 1.15 |

TABLE 2-continued

Examples E-01-E-55

| No. | MOLSTRUCTURE | Intermediate | [M + H]+ | rt |
|---|---|---|---|---|
| E-18 | | D-13 | 497 | 1.19 |
| E-19 | | D-14 | 480 | t0 |
| E-20 | | D-14 | 516 | 1.51 |
| E-21 | | D-14 | 490 | 1.03 |

TABLE 2-continued

Examples E-01-E-55

| No. | MOLSTRUCTURE | Intermediate | [M + H]⁺ | rt |
|---|---|---|---|---|
| E-22 | | D-14 | 491 | 2.05 |
| E-23 | | D-14 | 500 | 1.05 |
| E-24 | | D-30 | 501 | 1.09 |
| E-25 | | D-14 | 494 | 0.99 |

TABLE 2-continued

Examples E-01-E-55

| No. | MOLSTRUCTURE | Intermediate | [M + H]+ | rt |
|---|---|---|---|---|
| E-26 | | D-14 | 491 | 1.06 |
| E-27 | | D-14 | 524 | 1.07 |
| E-28 | | D-14 | 505 | 1.09 |
| E-29 | | D-14 | 506 | 1.83 |

TABLE 2-continued

Examples E-01-E-55

| No. | MOLSTRUCTURE | Intermediate | [M + H]+ | rt |
|---|---|---|---|---|
| E-30 | | D-14 | 514 | 1.87 |
| E-31 | | D-14 | 503 | 2.01 |
| E-32 | | D-15 | 460 | 1.11 |

TABLE 2-continued

Examples E-01-E-55

| No. | MOLSTRUCTURE | Intermediate | [M + H]+ | rt |
|---|---|---|---|---|
| E-33 | | D-16 | 473 | 1.21 |
| E-34 | | D-16 | 489 | 1.06 |
| E-35 | | D-16 | 475 | 1.01 |
| E-36 | | D-17 | 408 | 2.13 |

TABLE 2-continued

Examples E-01-E-55

| No. | MOLSTRUCTURE | Intermediate | [M + H]⁺ | rt |
|---|---|---|---|---|
| E-37 | | D-17 | 396 | 2.1 |
| E-38 | | D-17 | 394 | 2.01 |
| E-39 | | D-17 | 354 | 1.77 |
| E-40 | | D-18 | 516 | t0 |
| E-41 | | D-18 | 599 | t0 |

TABLE 2-continued

Examples E-01-E-55

| No. | MOLSTRUCTURE | Intermediate | [M + H]+ | rt |
|---|---|---|---|---|
| E-42 | | D-19 | 574 | 1.08 |
| E-43 | | D-19 | 561 | 1.05 |
| E-44 | | D-19 | 557 | 1.13 |
| E-45 | | D-19 | 547 | 0.99 |

TABLE 2-continued

Examples E-01-E-55

| No. | MOLSTRUCTURE | Intermediate | [M + H]+ | rt |
|---|---|---|---|---|
| E-46 | | D-19 | 593 | 1.24 |
| E-47 | | D-20 | 474 | 1.15 |
| E-48 | | D-20 | 488 | 1.25 |
| E-49 | | D-21 | | |
| E-50 | | D-23 | 519 | 1.03 |

TABLE 2-continued

Examples E-01-E-55

| No. | MOLSTRUCTURE | Intermediate | [M + H]+ | rt |
|---|---|---|---|---|
| E-51 | | D-25 | 517 | 1.03 |
| E-52 | | D-26 | 459 | 1.44 |
| E-53 | | D-28 | 508 | 1.17 |
| E-54 | | D-28 | 565 | 1.1 |

TABLE 2-continued

Examples E-01-E-55

| No. | MOLSTRUCTURE | Intermediate | [M + H]⁺ | rt |
|---|---|---|---|---|
| E-55 | | E-50 | 474 | 1.05 |

Examples F

Examples F-01 to F-20 can be synthesized according to one of the following general procedures. The appropriate acid or acid chloride required for synthesis can be deduced from the table of examples. Boc-groups are removed with HCl (5-10 eq.) by stirring overnight in dioxane at 40° C.

General Procedure F1:

Example D-17 (1 eq.) is taken up in NMP and sonicated until all material is dissolved. DMAP (0.1 eq.), DIPEA (5 eq.) and acid chloride (5 eq.) are added and the reaction mixture is stirred for 1 h at RT. The reaction mixture is poured in water and extracted with DCM. The organic phases are concentrated under reduced pressure and the product is purified by flash column chromatography (silica gel, 0-20% MeOH in DCM).

General Procedure F2:

The acid (1 eq.) is taken up in DCE, CDI (1 eq.) is added and the reaction mixture is stirred for 2 h at RT. Then 50% saturated brine is added and the reaction mixture is stirred vigorously for 1 min. The organic phase is separated, concentrated under reduced pressure, taken up in acetonitrile and added to a mixture of example D-17 (0.25 eq.) and DBU (0.5 eq.). The resulting reaction mixture is then stirred at 100° C. for 2 h. The reaction mixture is concentrated under reduced pressure, poured in water, brought to pH 8 by the addition of an aqueous saturated ammonium chloride solution and extracted with ethyl acetate containing 5% MeOH. The combined organic phase are washed with an aqueous 1% citric acid solution and brine, dried on magnesium sulfate and concentrated under reduced pressure. The product is purified by flash column chromatography (silica gel, 0-20% MeOH in DCM).

General Procedure F3:

The acid (2 eq.) and 2,4,6-trichloro-1,3,5-triazine (1 eq.) are taken up in NMP and stirred for 15 min at RT. Example D-17 (1 eq.), DBU (4 eq.) and DMAP (0.1 eq.) are taken up in NMP and stirred at RT for 10 min. Both reaction mixtures are combined and stirred overnight at 70° C. The reaction mixture is poured in water and extracted with DCM. The organic phases are concentrated under reduced pressure and the product is purified by flash column chromatography (silica gel, 0-20% MeOH in DCM).

TABLE 3

Examples F-01-F-20

| No. | MOLSTRUCTURE | Acid or acid chloride | [M + H]⁺ | rt |
|---|---|---|---|---|
| F-01 | | propionyl chloride | 382 | 3.36 |
| F-02 | | butyryl chloride | 396 | 1.62 |

TABLE 3-continued
Examples F-01-F-20
| No. | MOLSTRUCTURE | Acid or acid chloride | [M + H]+ | rt |
|---|---|---|---|---|
| F-03 | 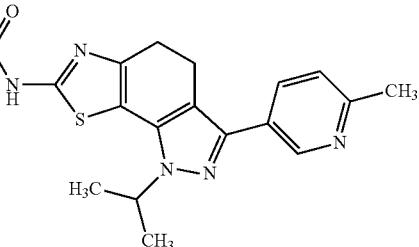 | methoxy-acetyl chloride | 398 | 1.18 |
| F-04 | 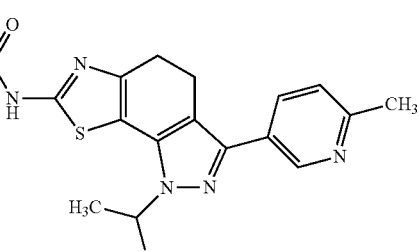 | 3-methyl-butyryl chloride | 410 | 1.73 |
| F-05 | 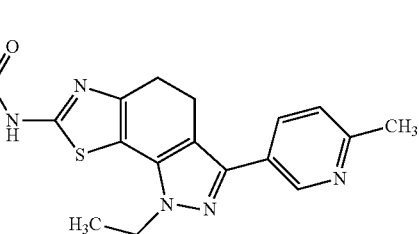 | 3-methyl-but-2-enoyl chloride | 408 | 1.73 |
| F-06 | 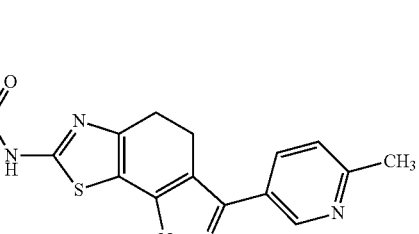 | pyridin-3-yl-acetic acid | 445 | 1.28 |
| F-07 | 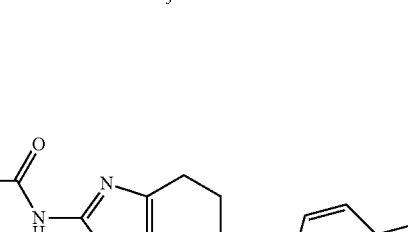 | 4-1,2,4-triazol-1-yl-butyric acid | 463 | 1.27 |

TABLE 3-continued

Examples F-01-F-20

| No. | MOLSTRUCTURE | Acid or acid chloride | [M + H]⁺ | rt |
|---|---|---|---|---|
| F-08 | | 3-pyridin-2-yl-propionic acid | 459 | 1.53 |
| F-09 | | imidazol-1-yl-acetic acid | 434 | 0.95 |
| F-10 | | 1,2,4-triazol-1-yl-acetic acid | 435 | 2.45 |
| F-11 | | 3-methoxy-propionic acid | 412 | 1.66 |
| F-12 | | N,N-dimethyl-succinamic acid | 453 | 1.58 |

TABLE 3-continued

Examples F-01-F-20

| No. | MOLSTRUCTURE | Acid or acid chloride | [M + H]+ | rt |
|---|---|---|---|---|
| F-13 | Chiral | (S)-pyrrolidine-1,2-dicarboxylic acid 1-tert-butyl ester | 423 | 1.41 |
| F-14 | Chiral | (R)-pyrrolidine-1,2-dicarboxylic acid 1-tert-butyl ester | 423 | 1.33 |
| F-15 | | (tert-butoxycarbonyl-methyl-amino)-acetic acid | 397 | 1.24 |
| F-16 | | 4-dimethylamino-butyric acid | 439 | 1.76 |
| F-17 | | (1,4-dimethyl-piperazin-2-yl)-acetic acid | 480 | 1.52 |
| F-18 | | 3-(3H-imidazol-4-yl)-propionic acid | 448 | 1.53 |

TABLE 3-continued

Examples F-01-F-20

| No. | MOLSTRUCTURE | Acid or acid chloride | [M + H]+ | rt |
|---|---|---|---|---|
| F-19 | | 3-(1-methyl-1H-imidazol-2-yl)-propionic acid | 462 | 1.56 |
| F-20 | | chloro-acetyl chloride | 402/404 | |

Examples G

Examples G-01 to G-05 can be synthesized according to the following general procedure. The appropriate amine required for synthesis can be deduced from the table of examples.

General Procedure G:

Example F-20 (1 eq.) is taken up in NMP, DIPEA (2 eq.) and amine (3 eq.) are added and the reaction mixture is stirred overnight at RT. The reaction mixture is poured in water, extracted with DCM and the organic phase is loaded on a SCX column. The column is washed with DCM and methanol and the product is eluted with a mixture of DCM and 7N ammonia in methanol. The product is further purified by flash column chromatography (silica gel, 0-20% methanol in DCM).

TABLE 4

Examples G-01-G-05

| No | MOLSTRUCTURE | Amine | [M + H]+ | rt |
|---|---|---|---|---|
| G-01 | | morpholine | 453 | 1.33 |

TABLE 4-continued

Examples G-01-G-05

| No | MOLSTRUCTURE | Amine | [M + H]⁺ | rt |
|----|--------------|-------|----------|-----|
| G-02 | | dimethylamine | 411 | 1.38 |
| G-03 | | piperidine | 451 | 1.77 |
| G-04 | | pyrrolidine | 437 | 1.51 |
| G-05 | | 1-methylpiperazine | 466 | 1.34 |

Examples H

Examples H-01 to H-14 can be synthesized according to the following general procedure. The appropriate amine or alcohol required for synthesis can be deduced from the table of examples.

General Procedure H:

Example D-17 (1 eq.), DBU (2 eq.) and CDI (2.5 eq.) are taken up in acetonitrile and stirred at 100° C. overnight. Amine or alcohol (5 eq.) is added and the reaction mixture is stirred again overnight at 100° C. The reaction mixture is concentrated under reduced pressure and the product is purified by HPLC (C-18, 2-98% acetonitrile in water).

TABLE 5

| | Examples H-01-H-14 | | | |
|---|---|---|---|---|
| No. | MOLSTRUCTURE | Amine | [M + H]+ | rt |
| H-01 | | O-methyl-hydroxylamine | 400 | 1.37 |
| H-02 | | methylamine | 383 | 1.72 |
| H-03 | | pyrrolidine | 423 | 1.90 |
| H-04 | | morpholine | 439 | 1.15 |
| H-05 | | 1-methyl-piperazine | 452 | 1.59 |
| H-06 | | ethylamine | 397 | 1.60 |

TABLE 5-continued
Examples H-01-H-14
| No. | MOLSTRUCTURE | Amine | [M + H]+ | rt |
|---|---|---|---|---|
| H-07 | 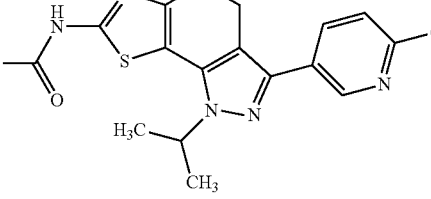 | ammonium chloride | 369 | 1.26 |
| H-08 | 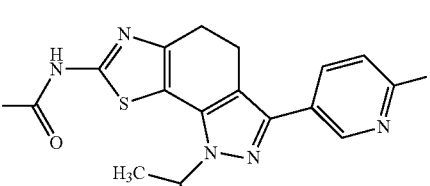 | dimethylamine | 397 | 1.58 |
| H-09 | 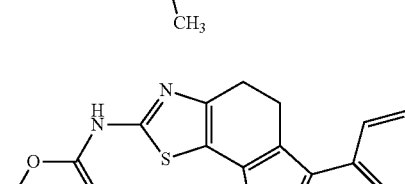 | 2-dimethyl-amino-ethanol | 441 | 1.47 |
| H-10 | 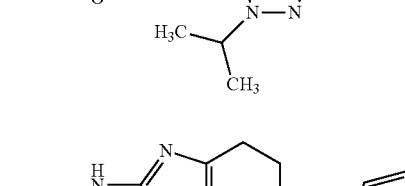 | N,N-dimethyl-ethylane-1,2-diamine | 440 | 1.63 |
| H-11 | 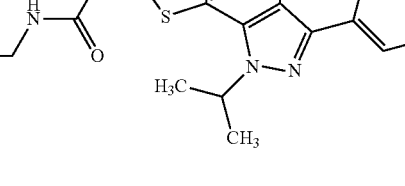 | 2-morpholin-4-yl-ethylamine | 482 | 1.59 |
| H-12 | 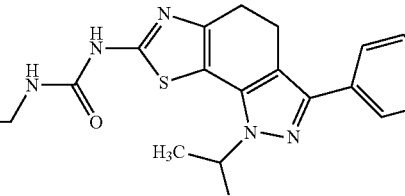 | 2-methoxy-ethanol | 428 | 1.50 |

TABLE 5-continued

Examples H-01–H-14

| No. | MOLSTRUCTURE | Amine | [M + H]⁺ | rt |
|---|---|---|---|---|
| H-13 | | 2-morpholin-4-yl-ethanol | 483 | 1.49 |
| H-14 | | 3-dimethylamino-propan-1-ol | 455 | 1.63 |

Examples J

Examples J-01 to J-02 can be synthesized according to the following general procedure. The appropriate example C can be deduced from the table of examples.

General Procedure J:

To a mixture of 400 mg (0.92 mmol) N-[1-(2-chloro-pyridin-3-yl)-3-(6-methylamino-pyridin-3-yl)-4,5-dihydro-1H-pyrazolo[4,3-g]benzothiazol-7-yl]-acetamide, 2.5 mL (18.3 mmol) Trimethylboroxide and 16 mg (0.022 mmol) bis(triphenylphosphine)palladium(II)-dichloride is added 10 mL DME, 2 mL ethanol and 1.37 mL of an aqueous 2 M $Cs_2CO_3$ solution. The reaction mixture is heated in the microwave for 2 h at 130° C. DCM (25 mL) and water (25 mL) are added and the phases are separated. The aqueous phase is washed twice with DCM (2×25 mL each). The combined organic layers are dried over sodium sulfate and the solvent is removed under reduced pressure. The crude material is dissolved in DMSO/TFA and purified using RP-LC/MS. The resulting product fractions are collected and the solvent is removed via freeze-drying to yield the desired product.

TABLE 6

Examples J-01–J-02

| No. | MOLSTRUCTURE | Heteroaryl chloride | [M + H]⁺ | rt |
|---|---|---|---|---|
| J-01 | | C-117 | 417 | 1.29 |
| J-02 | | C-118 | 432 | 1.21 |

Analytical Method
HPLC: Agilent 1100 Series
MS: Agilent LC/MSD SL
column: Phenomenex, Mercury Gemini C18, 3 µm, 2.0×20 mm,
　　Part. No. 00M-4439-B0-CE
solvent A: 5 mM $NH_4HCO_3$/20 mM $NH_3$
　　B: acetonitrile HPLC grade
detection: MS: Positive and negative
　　mass range: 120-700 m/z
　　fragmentor: 70
　　gain EMV: 1
　　threshold: 150
　　stepsize: 0.25
　　UV: 315 nm
　　bandwidth: 170 nm
　　reference: off
　　range: 210-400 nm
　　range step: 2.00 nm
　　peakwidth: <0.01 min
　　slit: 2 nm
injection: 5 µL
flow: 1.00 mL/min
column temperature: 40° C.

| gradient: | 0.00 min | 5% B |
|---|---|---|
| | 0.00-2.50 min | 5% –> 95% B |
| | 2.50-2.80 min | 95% B |
| | 2.81-3.10 min | 95% –> 5% B |

Instrument: Agilent 1100-SL: incl. DAD/MSD
Chromatography:
　　Column: Waters X-Bridge™ C18, 50×2.1 mm, 3.5
Method "Acid"
　　Eluent A: 0.1% formic acid in acetonitrile
　　Eluent B: 0.1% formic acid in water
　　Linear Gradient program: $t_0$=2% A, $t_{4\ min}$=98% A, $t_{6min}$=98% A
　　Flow: 0.8 mL/min
　　Column oven temperature: 35° C.
Method "Base"
　　Eluent A: 10 mM ammonia in acetonitrile
　　Eluent B: 10 mM ammonia in water
　　Linear Gradient program: $t_0$=2% A, $t_{4min}$=98% A, $t_{6min}$=98% A
　　Flow: 0.8 mL/min
　　Column oven temperature: 25° C.
Diode Array Detector (DAD):
　　Instrument: Agilent G1316A
　　Sample wavelength: 220-320 nm
　　Reference wavelength: Off
Mass Spectroscopy (MSD):
　　Instrument: Agilent LC/MSD-SL
　　Ionisation: ESI (Positive & Negative)
　　Mass range: 100-800
Abbreviations Used

| bu | butyl |
|---|---|
| d | day(s) |
| DC | thin layer chromatography |
| DCM | dichloromethan |
| DMF | N,N-dimethylformamide |
| DMSO | dimethylsulphoxide |
| et | ethyl |
| h | hour(s) |
| HPLC | high performance liquid chromatography |
| M | molar |
| min | minute(s) |
| mL | milliliter |
| MS | mass spectrometry |
| N | normal |
| NMR | nuclear resonance spectroscopy |
| ppm | part per million |
| Rf | retention factor |
| RP | reversed phase |
| RT | room temperature |
| Rt | retention time |
| DMAP | dimethyl-pyridin-4-yl-amine |
| tert | tertiary |
| THF | tetrahydrofuran |
| LiHMDS | Lithium hexamethyl disilazide |
| iPr | isopropyl |
| TBME | tertiary butylmethylether |
| NP | normal phase |
| CDI | carbonyl diimidazole |
| ACN | acetonitrile |
| BINAP | 2R,3S,2,2'-bis-(diphenyl-phosphino)-1,1'-binapthyl |
| DIPEA | diisopropylethyl amine |
| DCE | 1,2-dichloroethane |
| NMP | N-methylpyrrolindinone |
| prep | preparative |
| conc. | concentrated |
| TFA | trifluoroacetic acid |
| HATU | N-[(dimethylamino)-(1H-1,2,3-triazolo[4,5-b]pyridin-1-yl)-methylene]-N-methylmethan-aminium hexafluorophosphate N-oxide |
| TBAF | Tetrabutylammonium fluoride |
| TBTU | O-(Benzotriazol-1-yl)-N,N,N',N'-tetramethyluronium tetrafluoro-borate |
| PEPPSI | [1,3-Bis(2,6-Diisopropylphenyl)-imidazol-2-ylidene](3-chloro-pyridyl)palladium(II) dichloride |
| m.p | melting point |
| DBU | 1,8-diazabicyclo[5.4.0]undec-7-ene |

The Examples that follow describe the biological activity of the compounds according to the invention without restricting the invention to these Examples.

PC3 Proliferation Test

The test is based on measurement of cellular DNA content via fluorescent dye binding. Because cellular DNA content is highly regulated, it is closely proportional to cell number. The extent of proliferation is determined by comparing cell counts for samples treated with drugs with untreated controls.

PC3 (human prostate carcinoma cell line) cells are sown in microtitre plates and incubated overnight in culture medium at 37° C. and 5% $CO_2$. The test substances are diluted stepwise and added to the cells such that the total volume is 200 µL/well. Cells to which diluent, but not substance, is added serve as controls. After an incubation time of 3 days, the medium is replaced by 100 µL/well dye-binding solution and the cells are incubated at 37° C. in the dark for a further 60 min. For measuring the fluorescence, excitation takes place at a wavelength of 485 nm and the emission is measured at 530 nm.

$EC_{50}$ values are calculated using the GraphPad Prism program.

Most compounds of the Examples cited have an $EC_{50}$ (Proliferation PC3) of less than 0.5 µM.

P-AKT Measurement in PC3 Cells

P-AKT levels in PC3 cells are detected by cell-based ELISA. Cells are cultured in 96-well plates and treated with serial dilutions of test substances for 2 h. Cells to which diluent, but not substance, is added serve as controls. Subsequently, the cells are fixed rapidly to preserve protein modifications. Each well is then incubated with a primary antibody specific for Ser473-phosphorylated AKT. Subsequent incubation with secondary HRP-conjugated antibody and developing solution provides a colorimetric readout at 450 nm. $EC_{50}$ values are calculated using the GraphPad Prism program.

Most compounds of the Examples cited have an $EC_{50}$ (P-AKT PC3) of less than 0.5 µM.

The substances of the present invention are PI3 kinase inhibitors. On account of their biological properties, the novel compounds of the general formula (1) and their isomers and their physiologically tolerated salts are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancers may be treated with compounds according to the invention, without being restricted thereto:
brain tumours such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumour such as prolactinoma, hypophyseal incidentaloma, HGH (human growth hormone) producing adenoma and corticotrophic adenoma, craniopharyngiomas, medulloblastoma, meningeoma and oligodendroglioma; nerve tumours such as for example tumours of the vegetative nervous system such as neuroblastoma, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus and duodenum; eyelid tumours (basalioma or adenocarcinoma of the eyelid apparatus); retinoblastoma; carcinoma of the pancreas; carcinoma of the bladder; lung tumours (bronchial carcinoma—small-cell lung cancer (SCLC), non-small-cell lung cancer (NSCLC) such as for example spindle-cell plate epithelial carcinomas, adenocarcinomas (acinary, paillary, bronchioloalveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukaemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma—mucinous or serous cystoma, endometriodal tumours, clear cell tumour, Brenner's tumour); gall bladder cancer; bile duct cancer such as for example Klatskin tumour; testicular cancer (germinal or non-germinal germ cell tumours); laryngeal cancer such as for example supra-glottal, glottal and subglottal tumours of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumour, Ewing's sarcoma, and plasmocytoma, head and neck tumours (HNO tumours) such as for example tumours of the lips, and oral cavity (carcinoma of the lips, tongue, oral cavity), nasopharyngeal carcinoma (tumours of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumours of the paranasal sinuses and nasal cavity, tumours of the salivary glands and ears; liver cell carcinoma (hepatocellular carcinoma (HCC); leukaemias, such as for example acute leukaemias such as acute lymphatic/lymphoblastic leukaemia (ALL), acute myeloid leukaemia (AML); chronic lymphatic leukaemia (CLL), chronic myeloid leukaemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumour); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, mechlorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllo-toxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities.

In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or poly-functional alcohols (e.g. EtOH or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinyl-pyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the above-mentioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
|---|---|
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
|---|---|
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, micro-crystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 ml |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

The invention claimed is:

1. A compound of the formula (1),

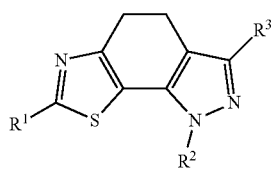

(1)

wherein $R^1$ is selected from among —$NHR^c$, —$NHC(O)R^c$, —$NHC(O)OR^c$, —$NHC(O)NR^cR^c$, —$NHC(O)N(R^g)OR^c$ and —$NHC(O)SR^c$, and $R^2$ denotes hydrogen or a group selected from among $C_{1-6}$alkyl, $C_{3-8}$cycloalkyl, 3-8 membered heterocycloalkyl, $C_{6-10}$-aryl, $C_{7-16}$arylalkyl and 5-10 membered heteroaryl, optionally substituted by one or more identical or different $R^4$ and $R^3$ denotes a pyridyl, substituted by —$CH_3$, and each $R^4$ denotes a group selected from among $R^a$, $R^b$ and $R^a$ substituted by one or more identical or different $R^b$ and/or $R^c$; and each $R^a$ independently of one another denotes a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is selected independently of one another from among —$OR^c$, $C_{1-3}$haloalkyloxy, —$OCF_3$, —$SR^c$, —$NR^cR^c$, —$ONR^cR^c$, —$N(OR^c)R^c$, —$N(R^g)NR^cR^c$, halogen, —$CF_3$, —$CN$, —$NC$, —$OCN$, —$SCN$, —$NO$, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$, —$N(R^g)C(NR^g)NR^cR^c$, —$N$=$R^cR^c$ and —$N$=$C(R^g)NR^cR^c$ and each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each $R^d$ denotes a suitable group and is selected independently of one another from among =$O$, —$OR^e$, $C_{1-3}$haloalkyloxy, —$OCF_3$, =$S$, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —$CN$, —$NC$, —$OCN$, —$SCN$, —$NO$, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$—$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —N($R^g$)C(N$R^g$)O$R^e$, —N($R^g$)C(NOH)$R^e$, —N($R^g$)C(N$R^g$)S$R^e$, —N($R^g$)C(N$R^g$)N$R^e R^e$, —N=$R^e R^e$ and —N=C($R^g$)N$R^e R^e$ each $R^e$ independently of one another denotes hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each $R^f$ denotes a suitable group and in each case is selected independently of one another from among =O, —O$R^g$, $C_{1-3}$haloalkyloxy, —OCF$_3$, =S, —S$R^g$, =N$R^g$, =NO$R^g$, =NN$R^g R^g$, =NN($R^h$)C(O)N$R^g R^g$, —N$R^g R^g$, —ON$R^g R^g$, —N($R^h$)N$R^g R^g$, halogen, —CF$_3$, —CN, —NC, —OCN, —SCN, —NO, —NO$_2$, =N$_2$, —N$_3$, —S(O)$R^g$, —S(O)O$R^g$, —S(O)$_2 R^g$, —S(O)$_2$O$R^g$, —S(O)N$R^g R^g$, —S(O)$_2$N$R^g R^g$, —OS(O)$R^g$, —OS(O)$_2 R^g$, —OS(O)$_2$O$R^g$, —OS(O)N$R^g R^g$, —OS(O)$_2$N$R^g R^g$, —C(O)$R^g$, —C(O)O$R^g$, —C(O)S$R^g$, —C(O)N$R^g R^g$, —C(O)N($R^h$)N$R^g R^g$, —C(O)N($R^h$)O$R^g$, —C(N$R^h$)N$R^g R^g$, —C(NOH)$R^g$, —C(NOH)N$R^g R^g$, —OC(O)$R^g$, —OC(O)O$R^g$, —OC(O)S$R^g$, —OC(O)N$R^g R^g$, —OC(N$R^h$)N$R^g R^g$, —SC(O)$R^g$, —SC(O)O$R^g$, —SC(O)N$R^g R^g$, —SC(N$R^h$)N$R^g R^g$, —N($R^h$)C(O)$R^g$, —N[C(O)$R^g$]$_2$, —N(O$R^h$)C(O)$R^g$, —N($R^h$)C(N$R^h$)$R^g$, —N($R^h$)N($R^h$)C(O)$R^g$, —N[C(O)$R^g$]N$R^g R^g$, —N($R^h$)C(S)$R^g$, —N($R^h$)S(O)$R^g$, —N($R^h$)S(O)O$R^g$, —N($R^h$)S(O)$_2 R^g$, —N[S(O)$_2 R^g$]$_2$, —N($R^h$)S(O)$_2$O$R^g$, —N($R^h$)S(O)$_2$N$R^g R^g$, —N($R^h$)[S(O)$_2$]$_2 R^g$, —N($R^h$)C(O)O$R^g$, —N($R^h$)C(O)S$R^g$, —N($R^h$)C(O)N$R^g R^g$, —N($R^h$)C(O)N$R^h$N$R^g R^g$, —N($R^h$)N($R^h$)C(O)N$R^g R^g$, —N($R^h$)C(S)N$R^g R^g$, —[N($R^h$)C(O)]$_2 R^g$, —N($R^h$)[C(O)]$_2 R^g$, —N{[C(O)]$_2 R^g$}$_2$, —N($R^h$)[C(O)]$_2$O$R^g$, —N($R^h$)[C(O)]$_2$N$R^g R^g$, —N{[C(O)]$_2$O$R^g$}$_2$, —N{[C(O)]$_2$N$R^g R^g$}$_2$, —[N($R^h$)C(O)]$_2$O$R^g$, —N($R^h$)C(N$R^h$)O$R^g$, —N($R^h$)C(NOH)$R^g$, —N($R^h$)C(N$R^h$)S$R^g$, —N($R^h$)C(N$R^h$)N$R^g R^g$, —N=$R^h R^h$ and —N=C($R^h$)N$R^h R^h$; and each $R^g$ independently of one another denotes hydrogen or a group optionally substituted by one or more identical or different $R^h$, selected from among $C_{1-6}$alkyl, 2-6 membered heteroalkyl, $C_{1-6}$haloalkyl, $C_{3-10}$-cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl; and each $R^h$ is selected independently of one another from among hydrogen, $C_{1-6}$alkyl, 2-6 membered heteroalkyl, $C_{1-6}$haloalkyl, $C_{3-10}$-cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, or a tautomer or pharmacologically acceptable salt thereof.

2. A compound according to claim 1, wherein $R^1$ is —NHC(O)$R^c$.

3. A compound according to claim 1, wherein $R^1$ is —NHC(O)CH$_3$.

4. A pharmaceutical preparation comprising a compound of formula (1) according to one of claim 1, 2 or 3, or a pharmaceutically effective salt thereof, in combination with conventional excipients and/or carriers.

5. A method for treating prostate cancer, which comprises administering to a host suffering from prostate cancer a therapeutically effective amount of a compound of the formula (1) according to one of claim 1 2 or 3, or a pharmacologically acceptable salt thereof.

* * * * *